US011922628B2

(12) United States Patent
Zhou et al.

(10) Patent No.: US 11,922,628 B2
(45) Date of Patent: Mar. 5, 2024

(54) SYSTEMS, METHODS, AND APPARATUSES FOR THE GENERATION OF SELF-TAUGHT MODELS GENESIS ABSENT MANUAL LABELING FOR THE PROCESSING OF MEDICAL IMAGING

(71) Applicant: Arizona Board of Regents on Behalf of Arizona State University, Scottsdale, AZ (US)

(72) Inventors: Zongwei Zhou, Tempe, AZ (US); Vatsal Sodha, San Jose, CA (US); Jiaxuan Pang, Tempe, AZ (US); Jianming Liang, Scottsdale, AZ (US)

(73) Assignee: Arizona Board of Regents on behalf of Arizona State University, Scottsdale, AZ (US)

( * ) Notice: Subject to any disclaimer, the term of this patent is extended or adjusted under 35 U.S.C. 154(b) by 409 days.

(21) Appl. No.: 17/224,886

(22) Filed: Apr. 7, 2021

(65) Prior Publication Data
US 2021/0326653 A1 Oct. 21, 2021

Related U.S. Application Data

(60) Provisional application No. 63/109,588, filed on Nov. 4, 2020, provisional application No. 63/007,176, filed on Apr. 8, 2020.

(51) Int. Cl.
*G06V 10/00* (2022.01)
*G06F 18/21* (2023.01)
(Continued)

(52) U.S. Cl.
CPC ............ *G06T 7/11* (2017.01); *G06F 18/2155* (2023.01); *G06F 18/2163* (2023.01);
(Continued)

(58) Field of Classification Search
CPC .......... G06N 3/08; G06N 3/088; G06N 3/045; G06N 3/0454; G06V 10/26;
(Continued)

(56) References Cited

U.S. PATENT DOCUMENTS 9,536,177 B2 * 1/2017 Chalasani .............. G06V 10/82
10,484,532 B1 * 11/2019 Newman ............... H04W 12/12
(Continued)

OTHER PUBLICATIONS

Noroozi, M. et al., "Boosting self-supervised learning via knowledge transfer," Proceedings of the IEEE conference on computer vision and pattern recognition, 2018, pp. 9359-9367.
(Continued)

*Primary Examiner* — Amir Alavi
(74) *Attorney, Agent, or Firm* — Elliott, Ostrander & Preston, P.C.

(57) ABSTRACT

Described herein are means for generation of self-taught generic models, named Models Genesis, without requiring any manual labeling, in which the Models Genesis are then utilized for the processing of medical imaging. For instance, an exemplary system is specially configured for learning general-purpose image representations by recovering original sub-volumes of 3D input images from transformed 3D images. Such a system operates by cropping a sub-volume from each 3D input image; performing image transformations upon each of the sub-volumes cropped from the 3D input images to generate transformed sub-volumes; and training an encoder-decoder architecture with skip connections to learn a common image representation by restoring the original sub-volumes cropped from the 3D input images from the transformed sub-volumes generated via the image transformations. A pre-trained 3D generic model is thus provided, based on the trained encoder-decoder architecture having learned the common image representation which is capable of identifying anatomical patterns in never before
(Continued)

seen 3D medical images having no labeling and no annotation. More importantly, the pre-trained generic models lead to improved performance in multiple target tasks, effective across diseases, organs, datasets, and modalities.

20 Claims, 34 Drawing Sheets

(51) Int. Cl.
| | |
|---|---|
| *G06F 18/214* | (2023.01) |
| *G06N 3/045* | (2023.01) |
| *G06N 3/088* | (2023.01) |
| *G06T 3/00* | (2006.01) |
| *G06T 7/11* | (2017.01) |
| *G06V 10/26* | (2022.01) |
| *G06V 10/77* | (2022.01) |
| *G16H 30/40* | (2018.01) |

(52) U.S. Cl.
CPC ............. *G06N 3/045* (2023.01); *G06N 3/088* (2013.01); *G06T 3/00* (2013.01); *G06V 10/26* (2022.01); *G06V 10/7715* (2022.01); *G16H 30/40* (2018.01); *G06V 2201/03* (2022.01)

(58) Field of Classification Search
CPC ............ G06V 10/7715; G06F 18/2155; G06F 18/2163; G06F 18/213; G06T 2207/10081; G06T 2207/10116; G06T 2207/20081; G06T 2207/20084; G06T 2207/20132; G06T 7/01; G06T 3/00; G16H 50/20; G16H 50/70; G16H 30/40
See application file for complete search history.

(56) References Cited

U.S. PATENT DOCUMENTS

| | | | | |
|---|---|---|---|---|
| 10,496,729 | B2 * | 12/2019 | Neumann | G16H 50/50 |
| 10,573,304 | B2 * | 2/2020 | Gemmeke | G10L 15/065 |
| 11,138,479 | B2 * | 10/2021 | Zhou | G06V 10/761 |
| 11,501,042 | B2 * | 11/2022 | Steingrimsson | G06N 3/04 |
| 11,515,030 | B2 * | 11/2022 | Mansi | G16H 20/40 |
| 11,557,036 | B2 * | 1/2023 | Liao | G06T 7/0012 |
| 11,586,930 | B2 * | 2/2023 | Meng | G10L 15/16 |
| 11,605,447 | B2 * | 3/2023 | Passerini | G16H 10/60 |
| 2019/0385021 | A1 | 12/2019 | Sasaki et al. | |
| 2021/0241468 | A1 * | 8/2021 | Zhang | G06T 7/246 |

OTHER PUBLICATIONS

Noroozi, M. et al., "Unsupervised learning of visual representations by solving jigsaw puzzles," Computer Vision—ECCV 2016: 14th European Conference, Amsterdam, The Netherlands, Oct. 11-14, 2016, Proceedings, Part VI. Cham: Springer International Publishing, 2016, pp. 69-84, Springer.
Pan, S.J. et al., "A survey on transfer learning." IEEE Transactions on knowledge and data engineering 22(10), 2010, pp. 1345-1359.
Pathak, D. et al., "Context encoders: Feature learning by inpainting," Proceedings of the IEEE Conference on Computer Vision and Pattern Recognition, 2016, pp. 2536-2544.
Rawat, W. et al., "Deep convolutional neural networks for image classification: A comprehensive review," Neural computation 29(9), 2017, pp. 2352-2449.
Ross, T. et al., "Exploiting the potential of unlabeled endoscopic video data with self-supervised learning." International journal of computer assisted radiology and surgery, 13, 2018, pp. 925-933.
Roth, H.R. et al., "A new 2.5 D representation for lymph node detection using random sets of deep convolutional neural network observations," Medical Image Computing and Computer-Assisted Intervention—MICCAI 2014: 17th International Conference, Boston, MA, USA, Sep. 14-18, 2014, Proceedings, Part I 17, 2014, pp. 520-527, Springer International Publishing.
Roth, H.R. et al., "Improving computer-aided detection using convolutional neural networks and random view aggregation," IEEE transactions on medical imaging 35(5), 2016, pp. 1170-1181.
Sayed, N. et al., "Cross and learn: Cross-modal self-supervision," Pattern Recognition: 40th German Conference, GCPR 2018, Stuttgart, Germany, Oct. 9-12, 2018, Proceedings 40, 2019, pp. 228-243, Springer International Publishing.
Setio, A.A.A. et al., "Pulmonary nodule detection in CT images: false positive reduction using multi-view convolutional networks," IEEE transactions on medical imaging 35(5), 2016, pp. 1160-1169.
Setio, A.A.A. et al., "Validation, comparison, and combination of algorithms for automatic detection of pulmonary nodules in computed tomography images: the LUNA16 challenge," Medical image analysis 42, 2017, pp. 1-13.
Shen, D. et al., "Deep learning in medical image analysis," Annual review of biomedical engineering, 19, 2017, pp. 221-248.
Shin, H.C. et al., "Deep convolutional neural networks for computer-aided detection: CNN architectures, dataset characteristics and transfer learning," IEEE transactions on medical imaging, 35(5), 2016, pp. 1285-1298.
SIIM-ACR Pneumothorax Segmentation, homepage of competition to detect pneumothorax using AI algorithm, URL: www.kaggle.com/c/siim-acr-pneumothorax-segmentation/; obtained Aug. 21, 2023.
Spitzer, H. et al., "Improving cytoarchitectonic segmentation of human brain areas with self-supervised siamese networks," Medical Image Computing and Computer Assisted Intervention—MICCAI 2018: 21st International Conference, Granada, Spain, Sep. 16-20, 2018, Proceedings, Part III 11, 2018, pp. 663-671, Springer International Publishing.
Sun, C. et al., "Revisiting unreasonable effectiveness of data in deep learning era," Proceedings of the IEEE international conference on computer vision, 2017, pp. 843-852.
Sun, W. et al., "Automatic feature learning using multichannel ROI based on deep structured algorithms for computerized lung cancer diagnosis," Computers in biology and medicine 89, 2017, pp. 530-539.
Tajbakhsh, N. et al., "Computer-aided detection and visualization of pulmonary embolism using a novel, compact, and discriminative image representation," Medical image analysis 58, 2019, p. 101541.
Tajbakhsh, N. et al., "Computer-aided pulmonary embolism detection using a novel vessel-aligned multi-planar image representation and convolutional neural networks," Medical Image Computing and Computer-Assisted Intervention—MICCAI 2015: 18th International Conference, Munich, Germany, Oct. 5-9, 2015, Proceedings, Part II 18, 2015, pp. 62-69, Springer International Publishing.
Tajbakhsh, N. et al., "Convolutional neural networks for medical image analysis: Full training or fine tuning?," IEEE transactions on medical imaging, 35(5), 2016, pp. 1299-1312.
Tajbakhsh, N. et al., "Surrogate supervision for medical image analysis: Effective deep learning from limited quantities of labeled data," 2019 IEEE 16th international symposium on biomedical imaging (ISBI 2019), IEEE, 2019.
Tang, H. et al., "Nodulenet: Decoupled false positive reduction for pulmonary nodule detection and segmentation," Medical Image Computing and Computer Assisted Intervention—MICCAI 2019: 22nd International Conference, Shenzhen, China, Oct. 13-17, 2019, Proceedings, Part VI 22. 2019, pp. 266-274 Springer International Publishing.
Tang, Y. et al., "Attention-guided curriculum learning for weakly supervised classification and localization of thoracic diseases on chest radiographs," Machine Learning in Medical Imaging: 9th International Workshop, MLMI 2018, Held in Conjunction with MICCAI 2018, Granada, Spain, Sep. 16, 2018, Proceedings 9, 2018, pp. 249-258, Springer International Publishing.
Vincent, P. et al., "Stacked denoising autoencoders: Learning useful representations in a deep network with a local denoising criterion," Journal of machine learning research, 11(12), 2010, pp. 3371-3408.
Vouldodimos, A. et al., "Deep learning for computer vision: A brief review," Computational intelligence and neuroscience, 2018, 13 pages.

(56) References Cited

OTHER PUBLICATIONS

Wang, H. et al., "Comparison of machine learning methods for classifying mediastinal lymph node metastasis of non-small cell lung cancer from 18 F-FFG PET/CT images," EJNMMI research 7, 2017, pp. 1-11.

Wang, X. et al., "Chestx-ray8: Hospital-scale chest x-ray database and benchmarks on weakly-supervised classification and localization of common thorax diseases," Proceedings of the IEEE Conference on Computer Vision and Pattern Recognition, 2017, pp. 2097-2106.

Weiss, K. et al., "A survey of transfer learning," Journal of Big Data 3(1), 2016, pp. 1-40.

Wu, B. et al., "Joint learning for pulmonary nodule segmentation, attributes and malignancy prediction," 2018 IEEI 15th International Symposium on Biomedical Imaging (ISBI 2018), IEEE, 2018, pp. 1109-1113.

Yosinski, J. et al., "How transferable are features in deep neural networks?," Advances in neural information processing systems, 27, 2014, pp. 3320-3328.

Zhang, L. et al., "Aet vs. aed: Unsupervised representation learning by auto-encoding transformations rather than data," Proceedings of the IEEE/CVF Conference on Computer Vision and Pattern Recognition, 2019, pp. 2547-2555.

Zhang, R. et al., "Colorful image colorization," Computer Vision—ECCV 2016: 14th European Conference, Amsterdam, The Netherlands, Oct. 11-14, 2016, Proceedings, Part III 14, 2016, pp. 649-666, Springer International Publishing.

Zhang, R. et al., "Split-brain autoencoders: Unsupervised learning by cross-channel prediction," Proceedings of the IEEE Conference on Computer Vision and Pattern Recognition, 2017, pp. 1058-1067.

Zhang, T. et al., "Solving large scale linear prediction problems using stochastic gradient descent algorithms," Proceedings of the twenty-first international conference on Machine learning, 2004, p. 116.

Zhou, Z. et al., "Models Genesis," Medical Image Analysis, vol. 67, 2021. 101840.

Zhou, Z. et al., "Fine-tuning convolutional neural networks for biomedical image analysis: actively and incrementally," Proceedings of the IEEE Conference on Computer Vision and Pattern Recognition, 2017, pp. 7340-7351.

Zhou, Z. et al., "Integrating active learning and transfer learning for carotid intima-media thickness video interpretation," Journal of digital imaging 32, 2019, pp. 290-299.

Zhou, Z. et al., "Models genesis: Generic autodidactic models for 3d medical image analysis," Medical Image Computing and Computer Assisted Intervention—MICCAI 2019: 22nd International Conference, Shenzhen, China, Oct. 13-17, 2019, Proceedings, Part IV 22, 2019, pp. 384-393, Springer International Publishing.

Zhou, Z. et al., "Unet++: A nested u-net architecture for medical image segmentation," Deep Learning in Medical Image Analysis and Multimodal Learning for Clinical Decision Support: 4th International Workshop, DLMIA 2018, and 8th International Workshop, ML-CDS 2018, Held in Conjunction with MICCAI 2018, Granada, Spain, Sep. 20, 2018, Proceedings 4, 2018, pp. 3-11, Springer International Publishing.

Zhuang, X. et al., "Self-supervised feature learning for 3d medical images by playing a rubik's cube," Medical Image Computing and Computer Assisted Intervention—MICCAI 2019: 22nd International Conference, Shenzhen, China, Oct. 13-17, 2019, Proceedings, Part IV 22, 2019, pp. 420-428, Springer International Publishing.

Alex, V. et al., Semisupervised learning using denoising autoencoders for brain lesion detection and segmentation, Journal of Medical Imaging 4(4), 2017, p. 041311.

Ardila, D. et al., "End-to-end lung cancer screening with three-dimensional deep learning on low-dose chest computed tomography," Nature medicine 25(6), 2019, pp. 954-961.

Aresta, G. et al., "iW-Net: an automatic and minimalistic interactive lung nodule segmentation deep network," Scientific reports 9(1), 2019, pp. 1-9.

Armato III, S.G. et al., "The lung image database consortium (LIDC) and image database resource initiative (IDRI): a completed reference database of lung nodules on CT scans," Medical physics 38(2), 2011, pp. 915-931.

Bakas, S. et al., "Identifying the best machine learning algorithms for brain tumor segmentation, progression assessment, and overall survival prediction in the BRATS challenge," arXiv preprint arXiv:1811.02629, 2019.

Bilic, P. et al., "The liver tumor segmentation benchmark (lits)," arXiv preprint arXiv:1901.04056, 2023.

Buzug, T.M., "Computed tomography," 2011, pp. 311-342, Springer Berlin Heidelberg.

Caron, M. et al., "Deep clustering for unsupervised learning of visual features," Proceedings of the European Conference on Computer Vision (ECCV), 2018, pp. 132-149.

Caron, M. et al., "Unsupervised pretraining of image features on non-curated data," Proceedings of the IEEE/CVF International Conference on Computer Vision, 2019, pp. 2959-2968.

Carreira, J. et al., "Quo vadis, action recognition? a new model and the kinetics dataset," Proceedings of the IEEE Conference on Computer Vision and Pattern Recognition, 2017, pp. 6299-6308.

Chen, L. et al., "Self-supervised learning for medical image analysis using image context restoration," Medical image analysis 58, 2019, p. 101539.

Chen, S. et al., "Med3d: Transfer learning for 3d medical image analysis," arXiv preprint arXiv:1904.00625, 2019.

Chen, T. et al., "Self-supervised gans via auxiliary rotation loss," Proceedings of the IEEE/CVF Conference on Computer Vision and Pattern Recognition, 2019, pp. 12154-12163.

Deng, J. et al., "Imagenet: A large-scale hierarchical image database," Proceedings of the IEEE Conference on Computer Vision and Pattern Recognition, 2009, pp. 248-255.

Ding, Y. et al., "A deep learning model to predict a diagnosis of Alzheimer disease by using 18F-FDG PET of the brain," Radiology, 290, 2019, pp. 456-464.

Doersch, C. et al., "Multi-task self-supervised visual learning," Proceedings of the IEEE International Conference on Computer Vision, 2017, pp. 2051-2060.

Doersch, C. et al., "Unsupervised visual representation learning by context prediction," Proceedings of the IEEE International Conference on Computer Vision, 2015, pp. 1422-1430.

Esteva, A. et al., "Dermatologist-level classification of skin cancer with deep neural networks," Nature, 542, 2017, pp. 115-118.

Forbes, G.B., "Human body composition: growth, aging, nutrition, and activity," 2012, Springer Science & Business Media.

Gibson, E. et al., "Automatic multiorgan segmentation on abdominal CT with dense V-networks," IEEE transactions on medical imaging, 37(8), 2018, pp. 1822-1834.

Gibson, E. et al., "Niftynet: a deep-learning platform for medical imaging," Computer methods and programs in biomedicine, 158, 2018, pp. 113-122.

Glorot, X. et al., "Understanding the difficulty of training deep feedforward neural networks," Proceedings of the Thirteenth International Conference on Artificial Intelligence and Statistics, 2010, pp. 249-256.

Goyal, P. et al., "Scaling and benchmarking self-supervised visual representation learning," arXiv preprint arXiv:1905.01235, 2019.

Greenspan, H. et al., "Guest editorial deep learning in medical imaging: Overview and future promise of an exciting new technique," IEEE Transactions on Medical Imaging, 35(5), 2016, pp. 1153-1159.

Guan, Q. "Multi-label chest x-ray image classification via category-wise residual attention learning," Pattern Recognition Letters, 130, 2020, pp. 259-266.

Gundel, S. et al., "Learning to recognize abnormalities in chest x-rays with location-aware dense networks," Progress In Pattern Recognition, Image Analysis, Computer Vision, and Applications: 23rd Iberoamerican Congress, CIARP 2018, Madrid, Spain, Nov. 19-22, 2018, Proceedings 23, pp. 757-765, Springer International Publishing.

He, K. et al., "Deep residual learning for image recognition," Proceedings of the IEEE Conference on Computer Vision and Pattern Recognition, 2016, pp. 770-778.

(56) References Cited

OTHER PUBLICATIONS

He, K. et al., "Delving deep into rectifiers: Surpassing human-level performance on imagenet classification," Proceedings of the IEEE Conference on Computer Vision and Pattern Recognition, 2015, pp. 1026-1034.

Hendrycks, D. et al., "Using self-supervised learning can improve model robustness and uncertainty," Advances in Neural Information Processing Systems, 32, 2019, pp. 15637-15648.

Huang, G. et al., "Densely connected convolutional networks," Proceedings of the IEEE Conference on Computer Vision and Pattern Recognition, 2017, pp. 4700-4708.

Hurst, R.T. et al., "Incidence of subclinical atherosclerosis as a marker of cardiovascular risk in retired professional football players," The American journal of cardiology, 105.8, 2010, pp. 1107-1111.

Iizuka, S. et al., "Globally and locally consistent image completion," ACM Transactions on Graphics (ToG), 36(4), 2017, pp. 1-14.

Ioffe, S. et al., "Batch normalization: Accelerating deep network training by reducing internal covariate shift," Conference on Machine Learning, 2015, pp. 448-456, PMLR.

Irvin, J. et al., "Chexpert: A large chest radiograph dataset with uncertainty labels and expert comparison," Proceedings of the AAAI conference on artificial intelligence, vol. 33., No. 01., 2019, pp. 590-597.

Jamaludin, A. et al., "Self-supervised learning for spinal MRIs," Deep Learning in Medical Image Analysis and Multimodal Learning for Clinical Decision Support: Third International Workshop, DLMIA 2017, and 7th International Workshop, ML-CDS 2017, Held in Conjunction with MICCAI 2017, Québec City, QC, Canada, Sep. 14, Proceedings 3, 2017 pp. 294-302, Springer International Publishing.

Jing, L. et al., "Self-supervised visual feature learning with deep neural networks: A survey," IEEE transactions on pattern analysis and machine intelligence, 43.11, 2021, pp. 4037-4058.

Kang, G. et al., "Patchshuffle regularization," arXiv preprint arXiv:1707.07103, 2017.

Kingma, D. et al., "Adam: A method for stochastic optimization," arXiv:1412.6980, 2015.

Kolesnikov, A. et al., "Revisiting self-supervised visual representation learning," Proceedings of the IEEE/CVF conference on computer vision and pattern recognition, 2019, pp. 1920-1929.

Krizhevsky, A., et al. "Imagenet classification with deep convolutional neural networks," Advances in neural information processing systems 25, 2012, 9 pages.

Litjens, G. et al., "A survey on deep learning in medical image analysis," Medical image analysis 42, 2017, pp. 60-88.

LiTS, 2017. Results of all submissions for liver segmentation. URL: https://competitions.codalab.org/competitions/17094#results; obtained Aug. 21, 2023.

Lu, L. et al., "Deep learning and convolutional neural networks for medical image computing: precision medicine, high performance and large-scale datasets," Deep Learning and Convolutional Neural Networks for Medical Image Computing, 2017, pp. 978-3, Springer.

Luna, 2016. Results of all submissions for nodule false positive reduction. URL: https://luna16.grand-challenge.org/results/; obtained Aug. 21, 2023.

Ma, Y. et al., "Multi-attention network for thoracic disease classification and localization," ICASSP 2019-2019 IEEE International Conference on Acoustics, Speech and Signal Processing (ICASSP), 2019, pp. 1378-1382.

Mahendran, A. et al., "Cross pixel optical-flow similarity for self-supervised learning," Computer Vision—ACCV 2018: 14th Asian Conference on Computer Vision, Perth, Australia, Dec. 2-6, 2018, Revised Selected Papers, Part V 14, 2019, pp. 99-116, Springer International Publishing.

Menze, B.H. et al., "The multimodal brain tumor image segmentation benchmark (Brats)," IEEE transactions on medical imaging, 34(10), 2014, pp. 1993-2024.

Mortenson, M.E., 1999. Mathematics for computer graphics applications. Industrial Press Inc.

Mundhenk, T.N. et al., "Improvements to context based self-supervised learning," Proceedings of the IEEE Conference on Computer Vision and Pattern Recognition, 2018, pp. 9339-9348.

National Lung Screening Trial Research Team, "Reduced lung-cancer mortality with low-dose computed tomographic screening," New England Journal of Medicine, 365.5, 2011, pp. 395-409.

\* cited by examiner

Table 1 - 175

| Pre-trained Model 176 | Modality 177 | Source Dataset 178 | Supervisor / Annotation 179 | Proxy Task 180 |
|---|---|---|---|---|
| Genesis Chest CT 2D | CT | LUNA 2016 | Self / 0 | Image restoration on 2D Chest CT slices |
| Genesis CT (3D) | CT | LUNA 2016 | Self / 0 | Image restoration on 3D Chest CT volumes |
| Genesis Chest X-ray (2D) | X-ray | ChestX-ray8 | Self / 0 | Image classification on 2D ImageNet |
| Models ImageNet | Natural | ImageNet | Full / 14M images | |
| Inflated 3D (I3D) | Natural | Kinetics | Full / 240K videos | Action recognition on human action videos |
| NiftyNet | CT | Pancreas-CT & BTCV | Full / 90 cases | Organ segmentation on abdominal CT |
| MedicalNet | CT, MRI | 3DSeg-8 | Full / 1,638 cases | Disease/organ segmentation on 8 datasets |

| Code 181 | Object 182 | Modality 183 | Target Dataset 184 | | Target Task 185 |
|---|---|---|---|---|---|
| NCC | Lung Nodule | CT | LUNA 2016 | | Lung nodule false positive reduction |
| NCS | Lung Nodule | CT | LIDC-IDRI | | Lung nodule segmentation |
| ECC | Pulmonary Emboli | CT | PE-CAD | | Pulmonary embolism false positive reduction |
| LCS | Liver | CT | LITS 2017 | | Liver segmentation |
| BMS | Brain Tumor | MRI | BraTS 2018 | | Brain tumor segmentation |

FIG. 1A

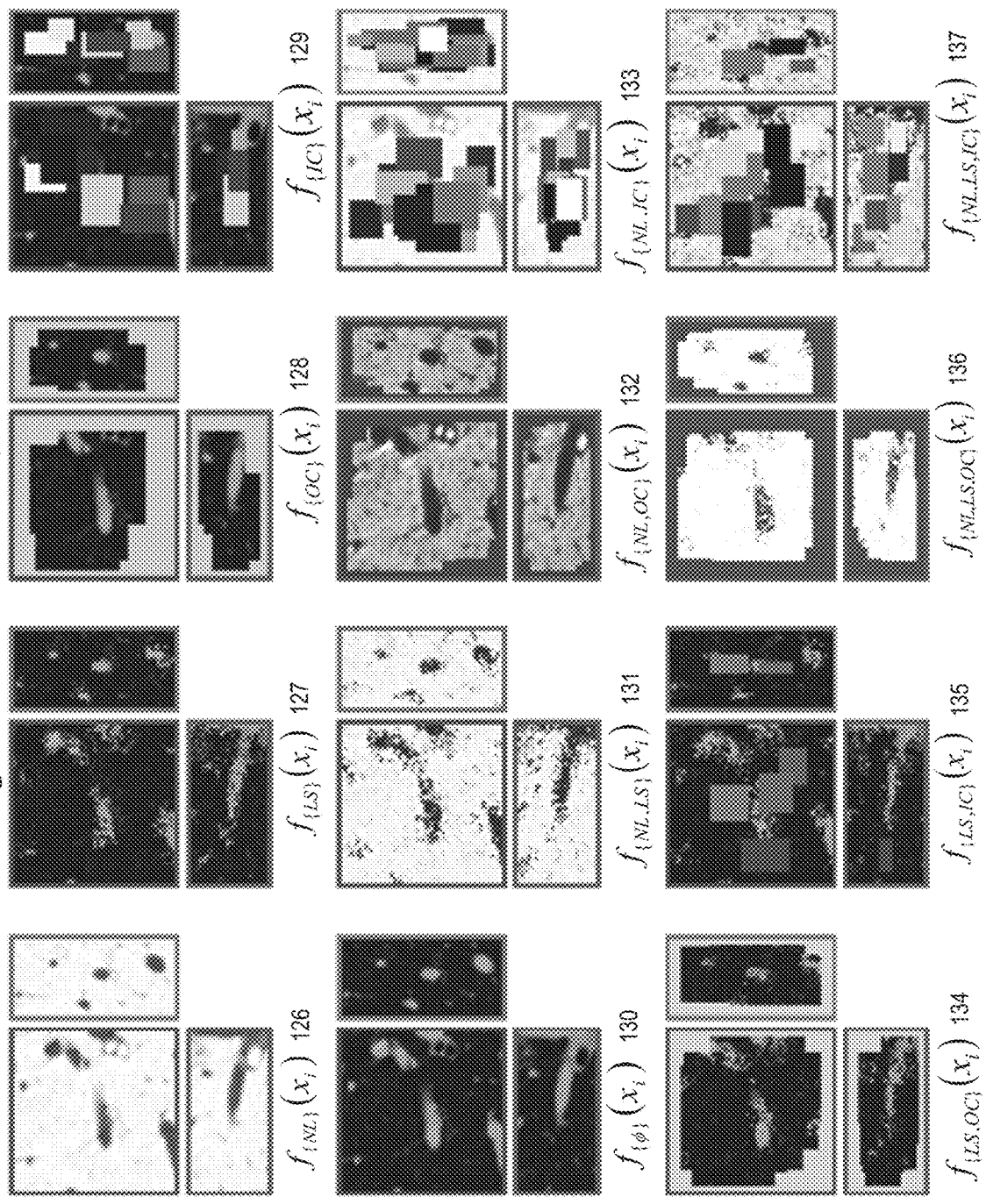

| Task 251 | Disease 252 | Organ 253 | Dataset 254 | Modality 255 |
|---|---|---|---|---|
| NCC 256 | X | | | |
| NCS 257 | X | | | |
| ECC 258 | X | | X | |
| LCS 259 | X | X | X | |
| BMS 260 | | X | X | X |

261 — X denotes properties are different between the source and target datasets.

FIG. 2E

Table 2 - 250

299(a) - Non-Linear Transformation

299(b) – Local pixel Shuffling Transformation

299(d) – Image Inner-Cutout Transformation

Table 3 - 600

| Pre-training | Approach | Target tasks 603 | | | | | |
|---|---|---|---|---|---|---|---|
| | | NCC (%) 604 | NCS (%) 605 | ECC (%) 606 | LCS (%) 607 | BMS (%) 608 |
| None 609 | Random with Uniform Init | 94.74±1.97 | 75.48±0.43 | 80.36±3.58 | 78.68±4.23 | 60.79±1.60 |
| | Random with Xavier Init | 94.25±5.07 | 74.05±1.97 | 79.99±8.06 | 77.82±3.87 | 58.52±2.61 |
| | Random with MSRA Init | 96.03±1.82 | 76.44±0.45 | 78.24±3.60 | 79.76±5.43 | 63.00±1.73 |
| (Fully) supervised 610 | 13D 615 | 98.26±0.27 | 71.58±0.55 | 80.55±1.11 | 70.65±4.26 | 67.83±0.75 |
| | NiftyNet 616 | 94.14±4.57 | 52.98±2.05 | 77.33±8.05 | 83.23±1.05 | 60.78±1.60 |
| | MedicalNet 617 | 95.80±0.49 | 75.68±0.32 | 80.43±1.44 | 85.52±0.58 | 66.09±1.35 |
| Self-supervised 641 | De-noising (revised in 3D) | 95.92±1.83 | 73.99±0.62 | 85.11±3.02 | 84.36±0.96 | 57.83±1.57 |
| | In-Painting | 91.46±2.97 | 76.02±1.55 | 79.79±3.55 | 81.36±4.83 | 61.38±3.84 |
| | Jigsaw | 95.47±1.24 | 70.90±1.55 | 81.79±1.04 | 82.04±1.26 | 63.33±1.11 |
| | DeepCluster | 97.22±0.55 | 74.95±0.46 | 84.82±0.62 | 82.66±1.00 | 65.96±0.85 |
| | Patch shuffling (revised in 3D) | 91.93±2.32 | 75.74±0.51 | 82.15±3.30 | 82.82±2.35 | 52.95±6.92 |
| | Rubik's Cube (revised) | 96.34±1.27 | 72.87±0.16 | 80.49±4.64 | 75.59±0.30 | 62.75±1.93 |
| | Genesis Chest CT (as disclosed) 621 | 98.34±0.44 | 77.62±0.64 | 87.20±2.87 | 85.10±2.15 | 67.96±1.29 |

FIG. 6

Table 4 - 875

| Task: NCC 881 | Random | ImageNet | Genesis |
|---|---|---|---|
| 2D slice-based input | 96.03±0.86 | 97.79±0.71 | 97.45±0.61 |
| 2.5D orthogonal input | 95.76±1.05 | 97.24±1.01 | 97.07±0.92 |
| 3D volume-based input | 96.03±1.82 | n/a | 98.34±0.44 |
| Task: ECC | Random | ImageNet | Genesis |
| 2D slice-based input | 60.33±8.61 | 62.57±8.04 | 62.84±8.78 |
| 2.5D orthogonal input | 71.27±4.64 | 78.61±3.73 | 78.58±3.67 |
| 3D volume-based input | 80.36±3.58 | n/a | 88.04±1.40 |

FIG. 8B

SYSTEMS, METHODS, AND APPARATUSES FOR THE GENERATION OF SELF-TAUGHT MODELS GENESIS ABSENT MANUAL LABELING FOR THE PROCESSING OF MEDICAL IMAGING

CLAIM OF PRIORITY

This U.S. Utility non-provisional patent application is related to, and claims priority to, the U.S. provisional patent application No. 63/007,176, filed Apr. 8, 2020, entitled "SYSTEMS, METHODS, AND APPARATUSES FOR THE GENERATION OF SELF-TAUGHT MODELS GENESIS ABSENT MANUAL LABELING FOR THE PROCESSING OF MEDICAL IMAGING," and is further related to, and claims priority to, the U.S. provisional patent application No. 63/109,588 filed Nov. 4, 2020, entitled "SYSTEMS, METHODS, AND APPARATUSES FOR THE GENERATION OF SELF-TAUGHT MODELS GENESIS ABSENT MANUAL LABELING FOR THE PROCESSING OF MEDICAL IMAGING," the entire contents of each being incorporated herein by reference as though set forth in full.

GOVERNMENT RIGHTS AND GOVERNMENT AGENCY SUPPORT NOTICE

This invention was made with government support under R01 HL 128785 awarded by the National Institutes of Health. The government has certain rights in the invention.

COPYRIGHT NOTICE

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

TECHNICAL FIELD

Embodiments of the invention relate generally to the field of medical imaging and analysis using convolutional neural networks for the classification and annotation of medical images, and more particularly, to systems, methods, and apparatuses for the generation of self-taught generic models without requiring any manual labeling, in which the generic models are then utilized for the processing of medical imaging.

BACKGROUND

The subject matter discussed in the background section should not be assumed to be prior art merely as a result of its mention in the background section. Similarly, a problem mentioned in the background section or associated with the subject matter of the background section should not be assumed to have been previously recognized in the prior art. The subject matter in the background section merely represents different approaches, which in and of themselves may also correspond to embodiments of the claimed inventions.

Machine learning models have various applications to automatically process inputs and produce outputs considering situational factors and learned information to improve output quality. One area where machine learning models, and neural networks in particular, provide high utility is in the field of processing medical images.

Within the context of machine learning and with regard to deep learning specifically, a Convolutional Neural Network (CNN, or ConvNet) is a class of deep neural networks, very often applied to analyzing visual imagery. Convolutional Neural Networks are regularized versions of multilayer perceptrons. Multilayer perceptrons are fully connected networks, such that each neuron in one layer is connected to all neurons in the next layer, a characteristic which often leads to a problem of overfitting of the data and the need for model regularization. Convolutional Neural Networks also seek to apply model regularization, but with a distinct approach. Specifically, CNNs take advantage of the hierarchical pattern in data and assemble more complex patterns using smaller and simpler patterns. Consequently, on the scale of connectedness and complexity, CNNs are on the lower extreme.

Heretofore, self-supervised learning has been sparsely applied in the field of medical imaging. Nevertheless, there is a massive need to provide automated analysis to medical imaging with a high degree of accuracy so as to improve diagnosis capabilities, control medical costs, and to reduce workload burdens placed upon medical professionals.

Not only is annotating medical images tedious and time-consuming, but it also demands costly, specialty-oriented expertise, which is not easily accessible. To address this challenge, a new framework is newly introduced herein and described in greater detail below, which is configured to generate models, called Generic Autodidactic Models or "Models Genesis," which are created ex nihilo (e.g., without any manual labeling or annotation required), and self-taught (e.g., learnt by self-supervision), and provide a generic foundation (e.g., serving as source models for generating application-specific target models). In such a way, generic models are provided which subsequent users may further configure for their specific implementation needs, such as performing an application-specific target-task.

Problematically, annotating medical imaging is tedious and time-consuming, and demands costly, specialty-oriented knowledge and skills, which are not easily accessible. Furthermore, any misdiagnosis from failure to recognize or correctly identify anatomical structures and abnormalities may result in potentially devastating impacts on patient morbidity and mortality.

Embodiments described herein therefore provide enhanced solutions to improve upon conventionally known image representation and learning techniques by leveraging machine learning to generate the Generic Autodidactic Models ("Models Genesis") without the previously required manual medical imaging annotation through the self-supervision techniques described herein, resulting in the generic or base model which may then be further customized for use as an application-specific target model.

The present state of the art may therefore benefit from the systems, methods, and apparatuses for the generation of self-taught generic models without requiring any manual labeling, as is described herein.

BRIEF DESCRIPTION OF THE DRAWINGS

Embodiments are illustrated by way of example, and not by way of limitation, and can be more fully understood with reference to the following detailed description when considered in connection with the figures in which:

FIG. 1A depicts Table 1 which summarizes pre-trained models with proxy tasks and target tasks, in accordance with described embodiments;

FIGS. 1B, 1C, and 1D depict the crop of a sub-volume ($X_i$) from the original CT scan, the election of image transformations f(•) to the sub-volume ($X_i$), and the training of a model to restore the original sub-volume ($X_i$), respectively;

FIG. 2E depicts Table 2 which shows that the Genesis CT model is pre-trained on only LUNA 2016 dataset (e.g., the source) and then fine-tuned for five distinct medical image applications (e.g., the targets), in accordance with described embodiments;

FIG. 6 depicts Table 3 which shows that the Models Genesis leads the best or comparable performance on five distinct medical target tasks over six self-supervised learning approaches (revised in 3D) and three competing publicly available (fully) supervised pre-trained 3D models, in accordance with described embodiments;

FIG. 8B depicts Table 4 at which shows the described 3D approach, initialized by Models Genesis, significantly elevates the classification performance compared with 2.5D and 2D approaches in reducing lung nodule and pulmonary embolism false positives, in accordance with described embodiments;

DETAILED DESCRIPTION

Figure 1B:
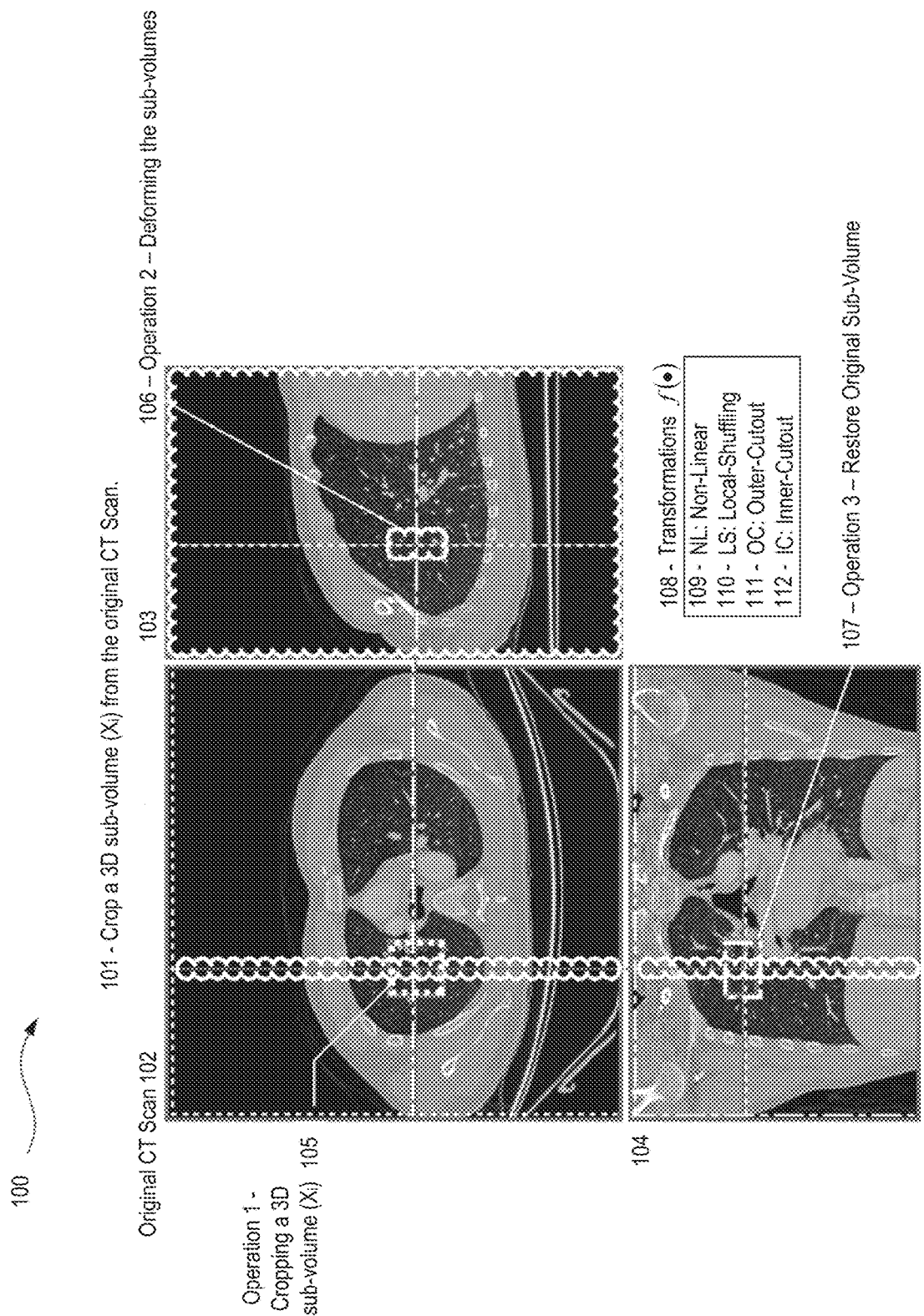

Described herein are systems, methods, and apparatuses for the generation of self-taught generic models without requiring any manual labeling, in the context of medical imaging.

Transfer learning from natural image to medical image has been established as one of the most practical paradigms in deep learning for medical image analysis. However, conventional approaches utilizing 3D imaging tasks in the most prominent imaging modalities (e.g., CT and MRI) have been reformulated and solved in 2D, losing the rich 3D anatomical information, thereby inevitably compromising performance of such prior known techniques.

Described herein are solutions which overcome this limitation by building a set of models, called Generic Autodidactic Models (also referred to herein as "Models Genesis" because they are created without the need for manual labeling or annotation), resulting in a self-taught (learnt by self-supervision) and generic foundational model which thus serves as a source model for generating application-specific target models.

Experimental results demonstrate that the Models Genesis significantly outperforms learning from scratch and existing pretrained 3D models in all five target 3D applications covering both segmentation and classification.

Moreover, it is known that learning a model from scratch simply in 3D does not yield performance better than transfer learning from ImageNet in 2D. Conversely, the generation of Models Genesis utilizing the techniques described herein consistently out-perform any prior known 2D/2.5D approaches, including techniques for fine-tuning the models pre-trained from ImageNet or fine-tuning the 2D versions of the Models Genesis described herein, thus confirming the importance of 3D anatomical information and significance of the described Models Genesis for 3D medical imaging.

This improved performance is attributed to the unified self-supervised learning framework which is described in greater detail below, which is built upon the simple yet powerful observation that sophisticated and recurrent anatomy in medical images can serve as strong yet free supervision signals for deep models to learn common anatomical representation automatically via self-supervision type machine learning techniques.

FIG. 1A depicts Table 1 at element 175 which summarizes pre-trained models with proxy tasks and target tasks.

More particularly, the first letter of the "Code †" 181 denotes the object 182 of interest (e.g., "N" for lung nodule, "E" for pulmonary embolism, "L" for liver, etc.) and the second letter denotes the modality 183 (e.g., "C" for CT, "M" for MRI, etc), while the last letter denotes the target task 185 (e.g., "C" for classification, and "S" for segmentation) for the indicated target dataset 184.

As depicted, there are multiple pre-trained models 176 listed, each having a corresponding modality 177, a source dataset 178, type of supervisor/annotation 179 utilized, and a proxy task 180 to which the pre-trained model 176 was applied.

The techniques described herein utilize transfer learning in a broader sense, where a source model is first trained to learn image presentation via full supervision or self-supervision by solving a problem, called proxy task 180 (general or application-specific), on a source dataset 178 with either expert-provided or automatically-generated labels (e.g., refer to the supervisor/annotation column at element 179), and then this pre-trained source model 176 is fine-tuned (e.g., transferred) through full supervision to yield a target model to solve application-specific problems (e.g., target tasks 185) in the same or different datasets (e.g., target datasets 184). Transfer learning is referred to as "same-domain" transfer learning when the models are pre-trained and fine-tuned within the same domain (e.g., modality, organ, disease, or dataset) and referred to as "cross-domain" transfer learning when the models are pre-trained in one domain and fine-tuned for a different domain.

Transfer learning from natural image to medical image has become the de facto standard in deep learning for medical image analysis, but given the marked differences between natural images and medical images, transfer learning is shown through experimental results to yield more powerful (e.g., application-specific) target models from the source models built directly using medical images.

Experiments utilizing chest imaging were utilized because the chest contains several critical organs, which are prone to a number of diseases that result in substantial morbidity and mortality, hence associated with significant health-care costs.

More particularly, Chest CT medical images are utilized due to their prominent role in diagnosing lung diseases, which the research community has accumulated into various Chest CT image databases, such as the LIDCIDRI database (Armato III et al., 2011) and NLST database (NLST, 2011), each containing a large number of Chest CT images.

Notwithstanding the availability of the accumulated Chest CT medical images, the fact remains that systematically annotating or labeling Chest CT scans is not only tedious, laborious, and time-consuming, but it also demands very costly, specialty-oriented skills, which are not easily accessible.

Experimental results derived from the methodologies described herein demonstrate that use of a large number of available Chest CT images without systematic annotation to train source models successfully yield high-performance target models via transfer learning.

According to certain embodiments, a framework is utilized to train generic source models for application to 3D medical imaging. As described herein, the framework is autodidactic, thus eliminating the need for labeled data by self-supervision learning techniques, the framework is highly robust, capable of learning comprehensive image representation from a mixture of self-supervised tasks, the framework is scalable, consolidating a variety of self-supervised tasks into a single image restoration task with the same encoder-decoder architecture, and the framework is and generic, benefiting a range of 3D medical imaging tasks through transfer learning.

The resulting models trained or generated utilizing the described framework are Generic Autodidactic Models (referred to herein as "Models Genesis) and the specific model trained via the framework using the Chest CT images is referred to herein as a "Genesis Chest CT" model.

Through ablation studies, a downgraded 2D version was also trained utilizing 2D Chest CT slices, which is referred to herein as a "Genesis Chest CT 2D" model. For thorough performance comparisons, a 2D model was trained using Chest X-ray images, referred to herein as a "Genesis Chest X-ray" model, each of which are detailed above in Table 1 at element 175.

Figure 7:
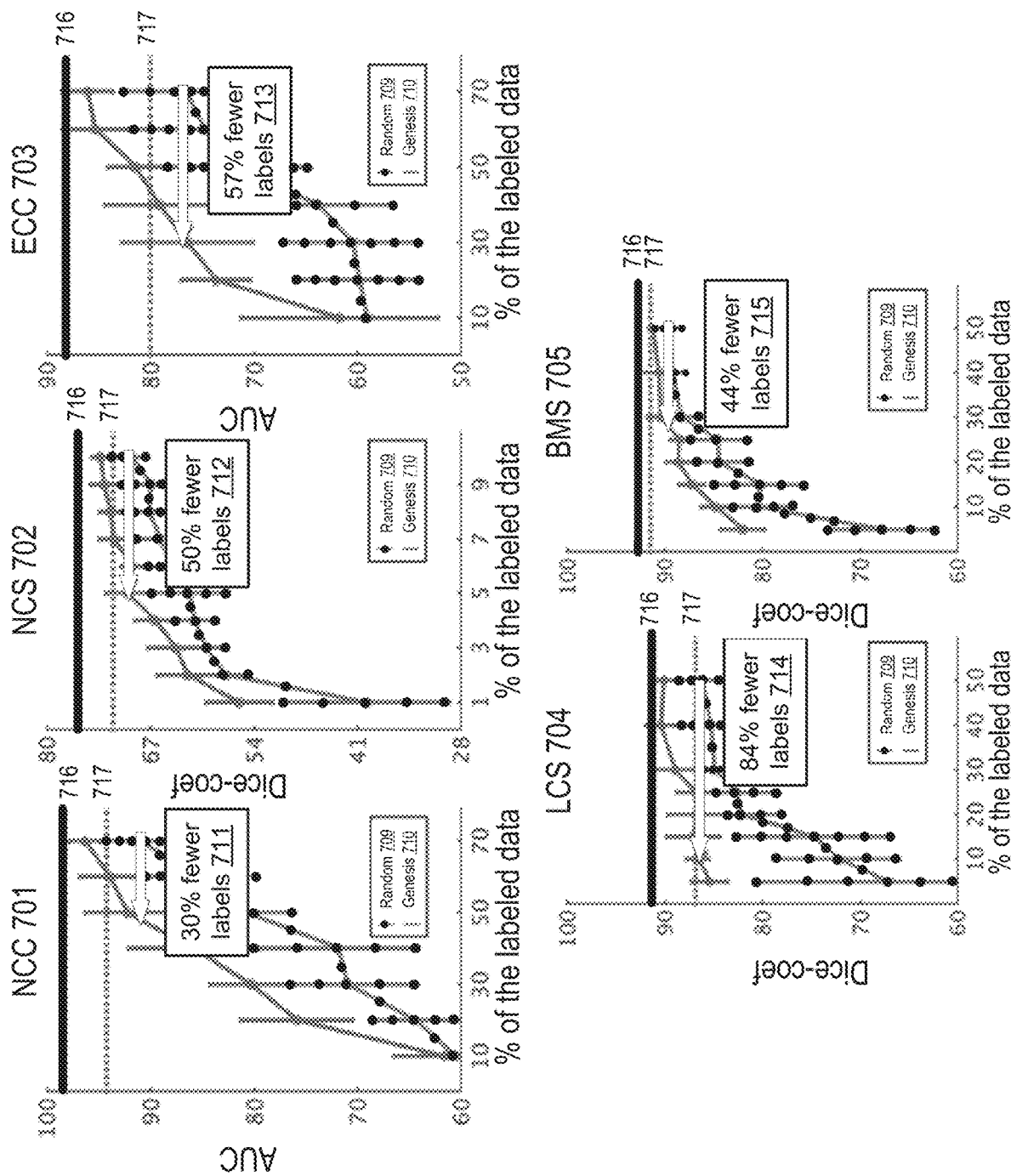
FIG. 7 illustrates that by initializing with the described Models Genesis, the annotation cost can be reduced by 30%, 50%, 57%, 84%, and 44% for the target tasks NCC, NCS, ECC, LCS, and BMS, respectively.

Preferably, 3D imaging tasks in the most prominent medical imaging modalities (e.g., CT and MRI) are solved directly in 3D. However, 3D models have significantly more parameters than their 2D counterparts, and therefore conventional approaches utilizing direct 3D solving require more labeled data for training. As a result, learning from scratch directly in 3D will not necessarily yield performance better than fine-tuning Models ImageNet (e.g., pre-trained models on ImageNet), as illustrated at FIG. 7, below.

However, experimental results utilizing the described methodologies demonstrate that the Genesis Chest CT model described herein not only significantly outperforms learning 3D models from scratch (refer to FIG. 4), but the described Genesis Chest CT model also consistently outperforms any previously known 2D/2.5D approaches, including fine-tuning Models ImageNet or fine-tuning the described Genesis Chest X-ray and Genesis Chest CT 2D (see FIG. 7 and Table 4 below). Furthermore, the described Genesis Chest CT model surpasses publicly available, pre-trained, (fully) supervised 3D models, as detailed below at Table 3.

Experimental results confirm the importance of 3D anatomical information and demonstrate the significance of Models Genesis for 3D medical imaging. This performance is attributable to the following key observation: medical imaging protocols typically focus on particular parts of the body for specific clinical purposes, resulting in images of similar anatomy.

The sophisticated yet recurrent anatomy offers consistent patterns for self-supervised learning to discover a common representation of a particular body part, such as the lungs as described herein with reference to the experimental results.

Figure 1D:
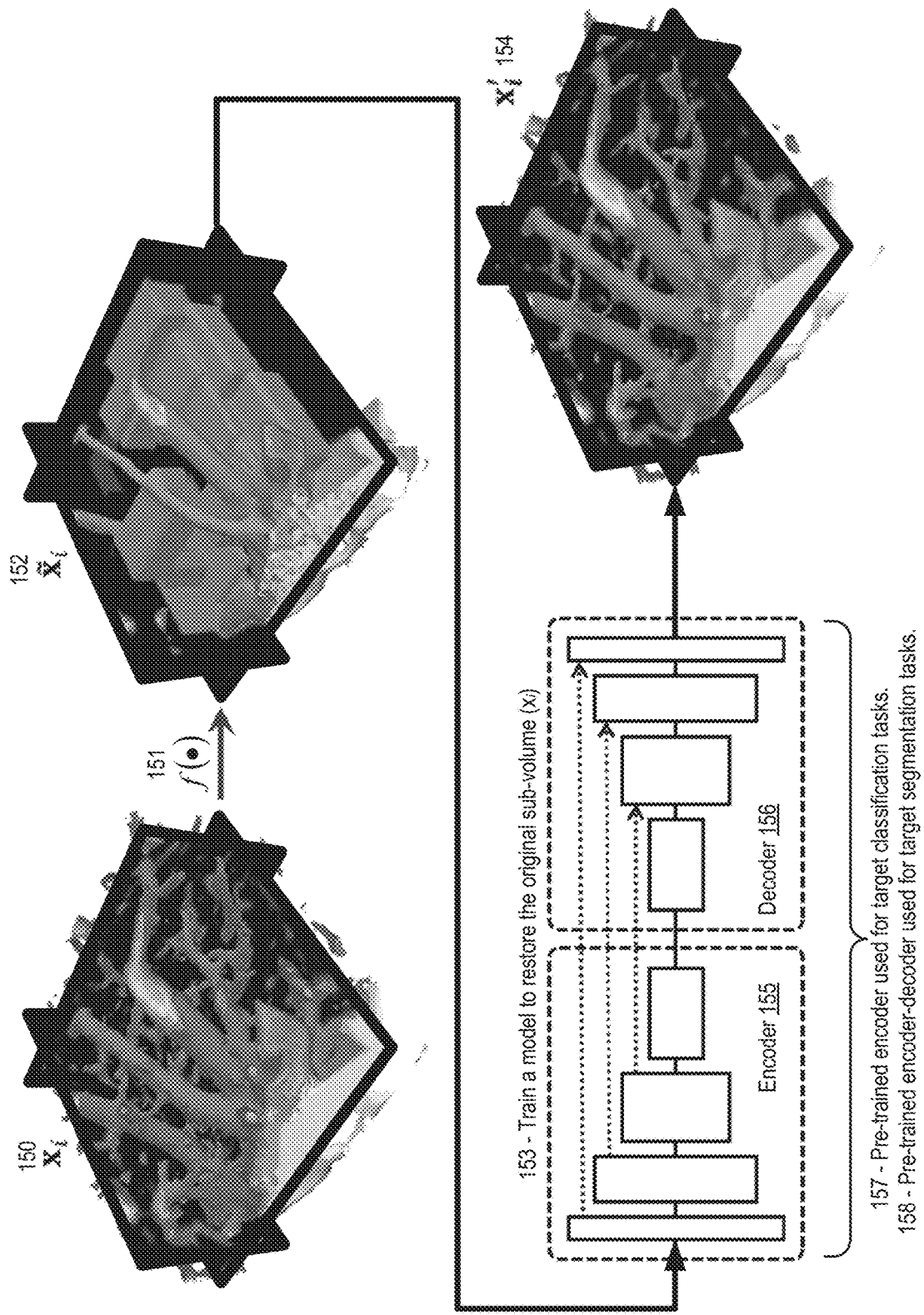

FIGS. 1B, 1C, and 1D depict the crop of a sub-volume ($X_i$) from the original CT scan (at FIG. 1B), the election of image transformations f(•) to the sub-volume ($X_i$) (at FIG. 1C), and the training of a model to restore the original sub-volume ($X_i$) (at FIG. 1D), respectively.

The self-supervised learning framework aims to learn general-purpose image representation by recovering the original sub-volumes of images from their transformed ones.

Processing first crops arbitrarily-sized sub-volume $x_i$ at a random location from an unlabeled CT image, as depicted at FIG. 1B.

As depicted at FIG. 1B, each 3D sub-volume $x_i$ (element 105) will undergo at most three out of four transformations f(•) 108, as indicated by the key, including: Non-Linear (NL) transformation 109, Local-Shuffling (LS) transformation 110, Outer-Cutout (OC) transformation 111, and Inner-Cutout (IC) transformation 112, resulting in a transformed 3D sub-volume $\tilde{x}_i$ (element 105). The outer-cutout and inner-cutout transformations (111 and 112) are considered mutually exclusive, therefore, in addition to the four original individual transformations, processing further yields eight more transformations, including one identity mapping ($\phi$ meaning none of the four individual transformations is selected) and seven combined transformations.

As depicted at FIG. 1C, a Model Genesis, an encoder-decoder architecture with skip connections in between, is trained to learn a common image representation by restoring the original sub-volume $x_i$ (as ground truth) from the transformed one $\tilde{x}_i$ (as input), in which the reconstruction loss (MSE) is computed between the model prediction $x_i'$ and ground truth $x_i$. Once trained, the encoder alone can be fine-tuned for target classification tasks; while the encoder and decoder together can be fine-tuned for target segmentation tasks.

In such a way, the self-supervised learning method described herein recovers anatomical patterns from images transformed via various ways utilizing a unified framework, thus resulting in each of (i) a collection of generic pre-trained 3D models, performing effectively across diseases, organs, and modalities, (ii) a scalable self-supervised learning framework, offering encoder for classification and encoder-decoder for segmentation, and (iii) a set of self-supervised training schemes, learning robust representation from multiple perspectives.

The Models Genesis techniques described herein provide the ability to learn a common image representation that is transferable and generalizable across diseases, organs, and modalities.

The self-supervised learning framework depicted at FIGS. 1B-1D, enable training 3D models from scratch using unlabeled images, consisting of the three steps shown, namely, operation 1 (element 105) which includes cropping 3D sub-volumes $\tilde{x}_i$ from patient CT images (e.g., original CT scan 102), followed by deforming the sub-volumes at operation 2 (element 106), and lastly, training a model to restore the original sub-volume at operation 3 (element 107).

Below, the denotations of a self-supervised learning framework are described in greater detail, followed by each of the training schemes with its learning objectives and perspectives, and a summary of the four unique properties of the described Models Genesis.

Image restoration proxy task: Given a raw dataset consisting of N patient volumes, theoretically an infinite number of sub-volumes may be cropped from the dataset. In practice, a subset $X=\{x_1, x_2, \ldots, x_n\}$ is randomly generated, which includes n number of sub-volumes and then an image transformation function is applied to these sub-volumes, yielding $\tilde{x}=f(X)$, where $\tilde{X}=\{\tilde{x}_1, \tilde{x}_2, \ldots, \tilde{x}_n\}$ and where f(•) denotes a transformation function.

Subsequently, a Model Genesis, being an encoder-decoder network with skip connections in between, will learn to approximate the function g(•) which aims to map the transformed sub-volumes $\tilde{x}$ back to their original ones X, that is, $g(\tilde{x})=x=f^{-1}(\tilde{x})$.

To avoid heavy weight dedicated towers for each proxy task and to maximize parameter sharing in Models Genesis, four self-supervised schemes are consolidated into a single image restoration task, enabling models to learn robust image representation by restoring from various sets of image transformations. The disclosed framework includes four transformations f(•) 108, namely (1) a Non-Linear (NL) transformation at element 109, (2) a Local-Shuffling (LS) transformation at element 110, (3) an Outer-Cutout (OC) transformation at element 111, and (4) an Inner-Cutout (IC) transformation at element 112. Each transformation f(•) 108 is independently applied to a sub-volume 105 with a pre-defined probability, while outer-cutout and inner-cutout transformations are considered mutually exclusive. Consequently, each sub-volume 105 will undergo at most three of the above transformations, resulting in twelve possible transformed sub-volumes (see operation 2 at FIG. 1B).

Thus, as is depicted by FIG. 1C, processing may elect the image transformation f(•) 108 which is to be applied to the original sub-volume $x_i$ (as the ground truth), selecting from any of the twelve (12) depicted transformations 126, 127, 128, 129, 130, 131, 132, 133, 134, 135, 136, and 137.

As depicted at FIG. 1D, and so as to improve clarity, a training scheme is further defined as the process that (1) transforms sub-volumes using any of the aforementioned transformations, thus transforming the original sub-volume $x_i$ (as the ground truth at element 150) via transformation f(•) at element 151 and resulting in transformed sub-volumes $\tilde{x}_i$, and then followed by further processing (2) which then trains a model to restore the original sub-volumes $x_i$ (as shown at element 153) from the transformed ones (at element 152). Each individual training scheme is referred to as the scheme using one particular individual transformation. As depicted here, the pre-trained encoder 155 is used for target classification tasks (e.g., element 157) while the decoder 156 is utilized as part of the pre-trained encoder-decoder for target segmentation tasks (e.g., element 158).

Notably, the task of image restoration is not always the ultimate goal, per se. Rather, while restoring images is advocated and investigated as a training scheme for models to learn image representation, the usefulness of the learned representation is assessed objectively based on its generalizability and transferability to various target tasks, beyond those which are expressly defined herein.

FIGS. 2A, 2B, 2C, and 2D illustrate the proposed image transformations and their learning perspectives.

For the sake of simplicity and clarity, FIGS. 2A, 2B, 2C, and 2D, illustrate the transformation on a 2D CT slice, however, the Genesis Chest CT model from which the experimental results are derived is actually is trained directly using 3D sub-volumes, which are transformed in a 3D manner. The various 3D image transformations, as depicted at elements 209, 210, 211, 202, 213, and 214 and corresponding to columns 203 through 208 are thus applied, with the exception of a non-linear transformation, which cannot be approximated in 2D. Column 202 on the top row is blank because the original image has not yet been transformed.

Figure 2A:
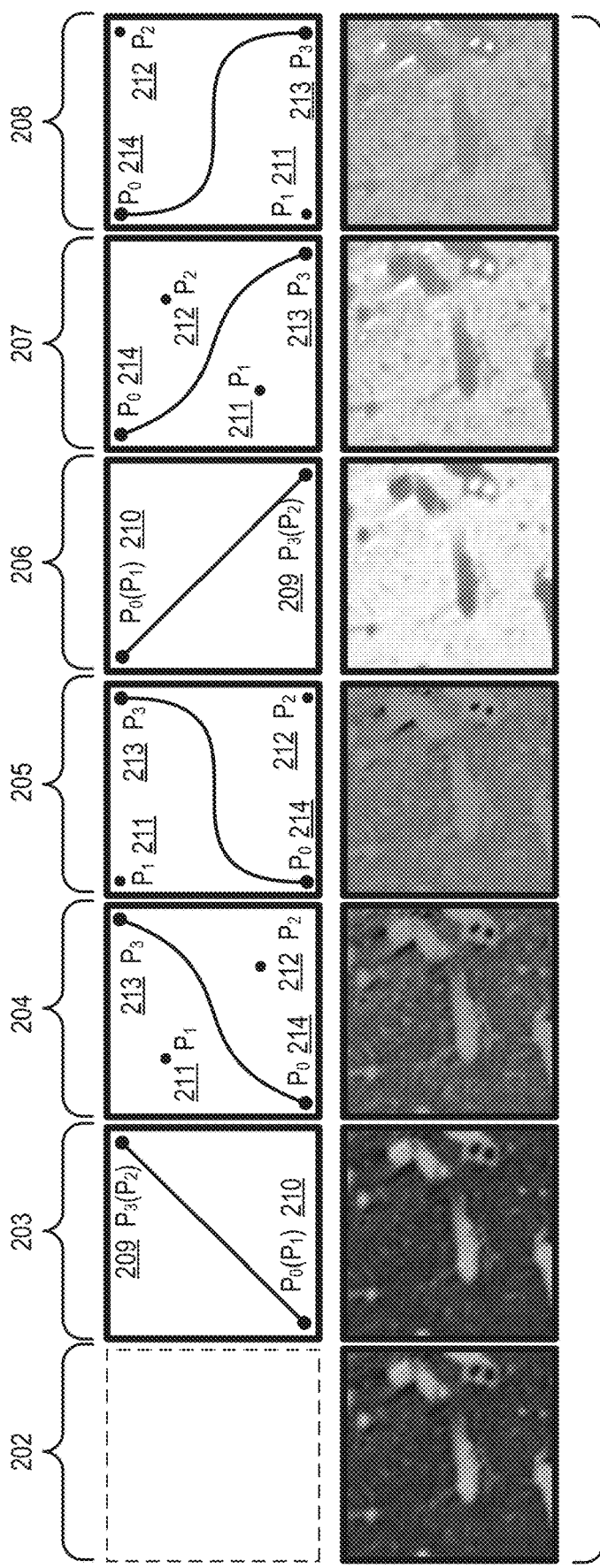
FIGS. 2A, 2B, 2C, and 2D illustrate the proposed image transformations and their learning perspectives.

For ease of understanding, FIG. 2A depicts non-linear transformations, as an image undergoing different translating functions in Columns 2 through 7 corresponding to columns 203, 204, 205, 206, 207, and 208, which results in the learning of an organ's appearance via non-linear transformation (e.g., element 201).

Figure 2B:
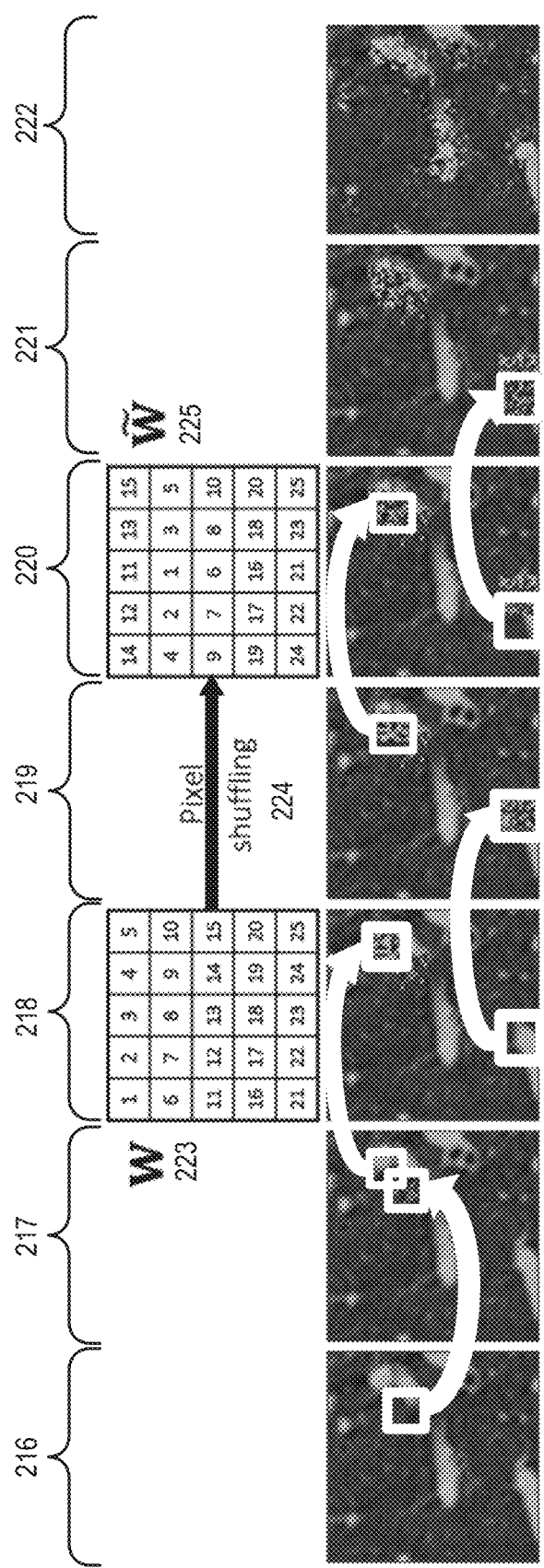

At FIG. 2B local-shuffling is depicted via columns 216, 216, 218, 219, 220, 221, and 222. The depicted non-linear transformation includes subjecting the cropped sub-volume to various deformations via the pixel shuffling operation 224 between W at element 223 and transformed $\tilde{W}$ at element 225, resulting in the learning of organ texture and local boundaries via the local pixel shuffling operation 215.

Figure 2C:
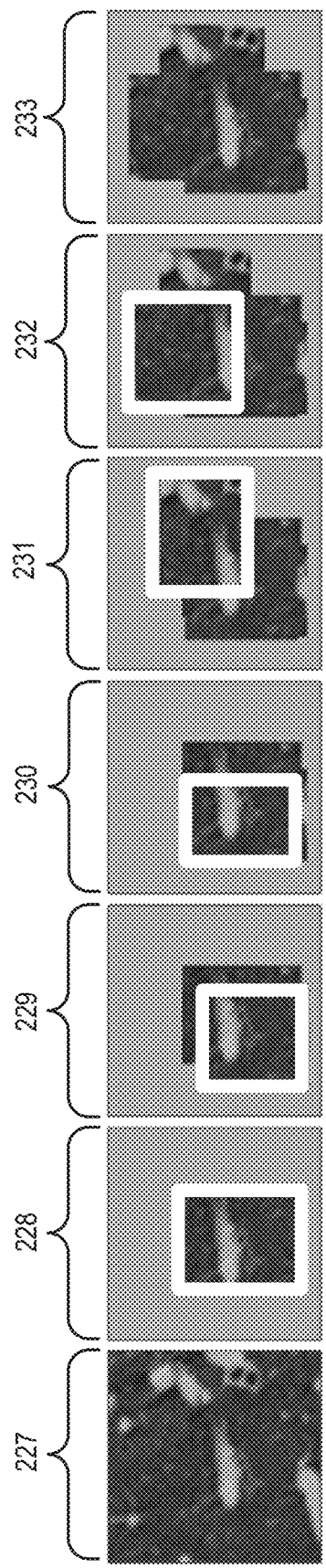

At FIG. 2C an outer-cutout operation is depicted, via the operations depicted at columns 227, 228, 229, 230, 231, 232, and 233, resulting in the learning of organ spatial layout and global geometry via the outer-cutout operation 226.

Figure 2D:
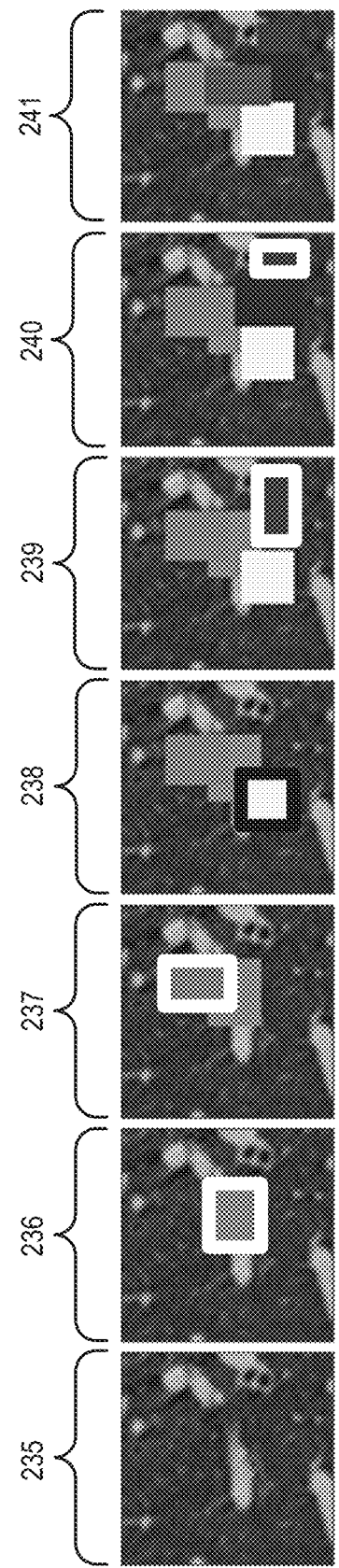
Figure 2F:
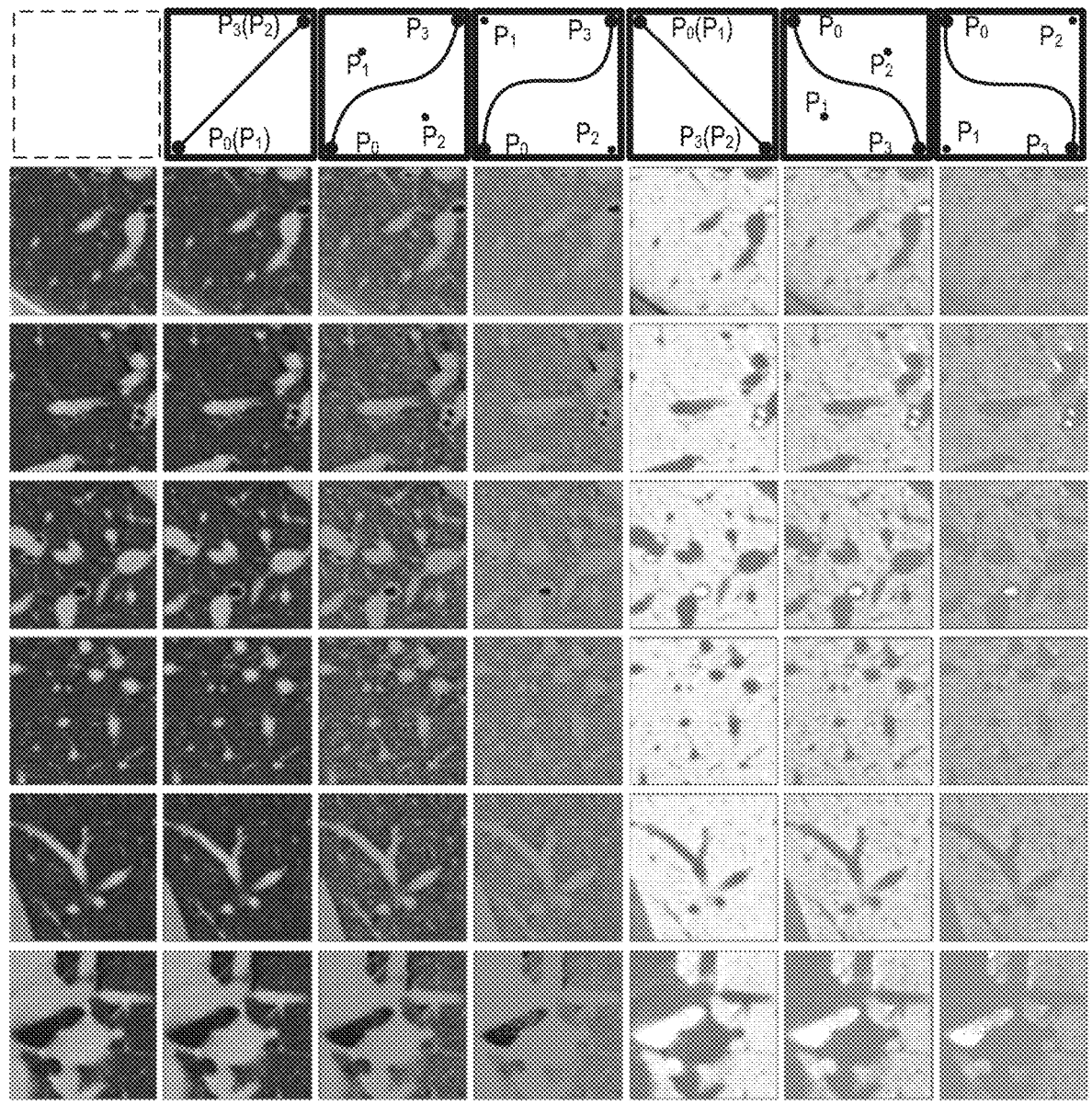
FIGS. 2F, 2G, 2H, and 2I depict four image transformations, non-linear transformation, local pixel shuffling transformation, image outer-cutout transformation, and image inner-cutout transformation, in accordance with the described embodiments.
Figure 2G:
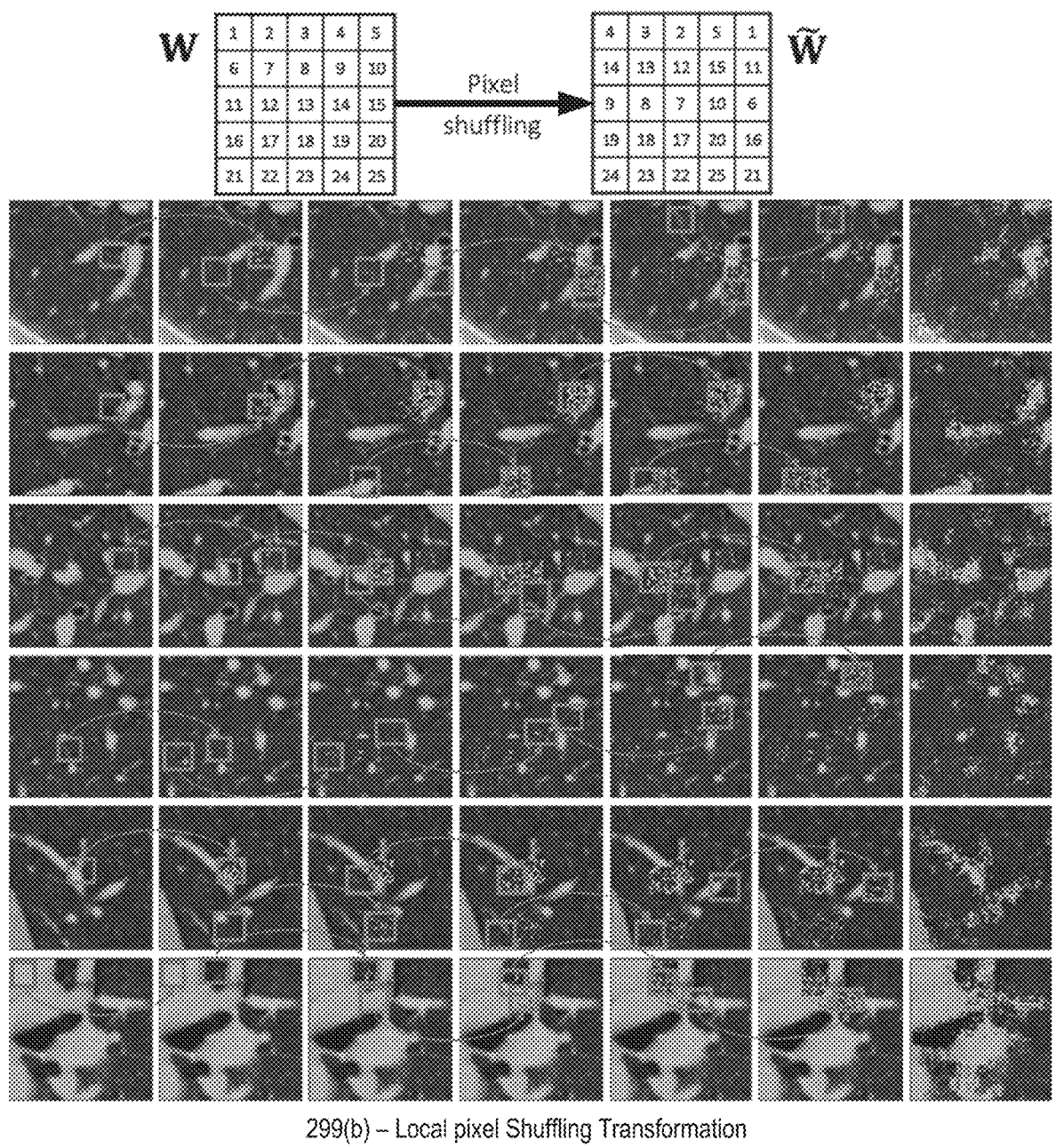
Figure 2H:
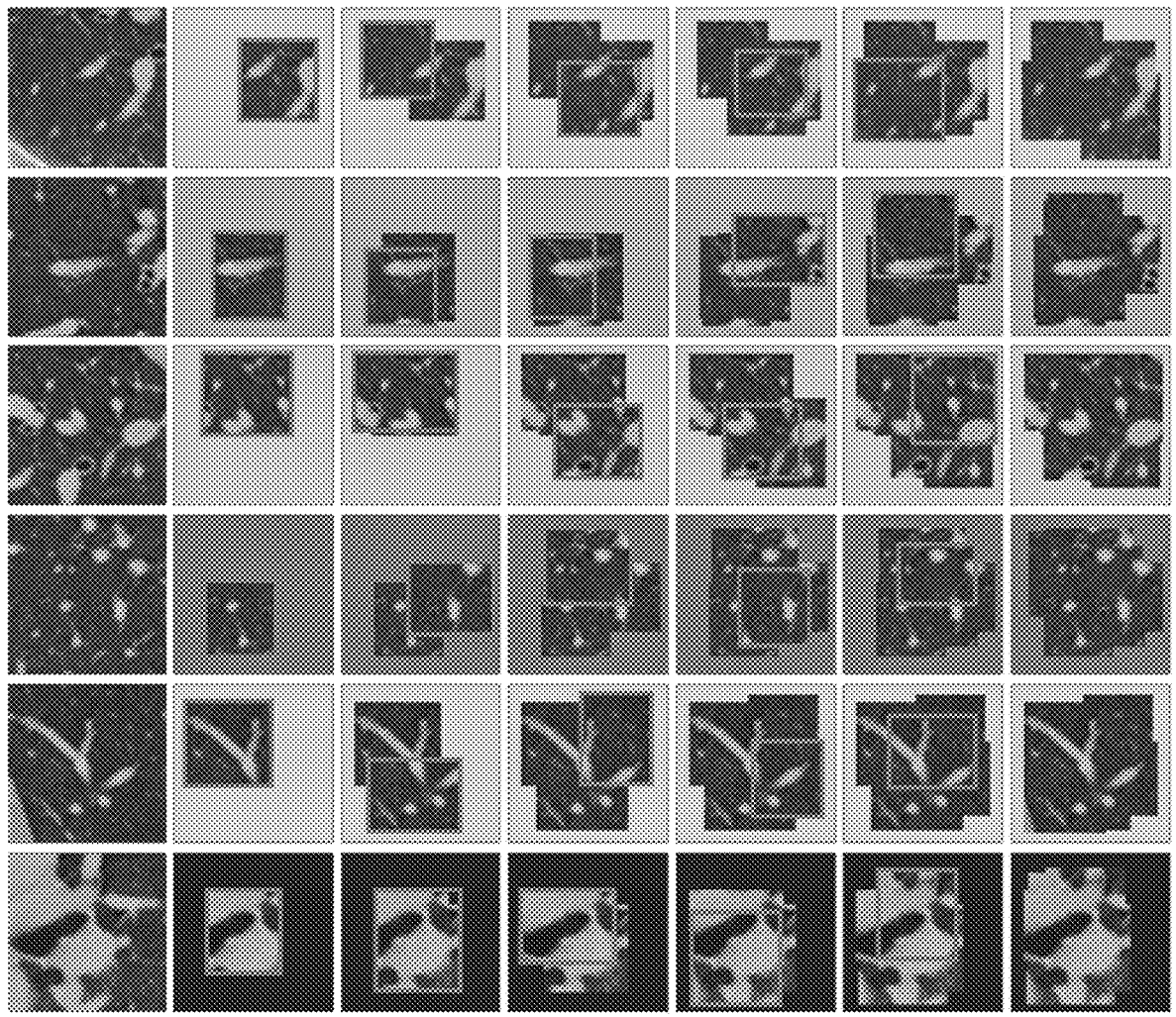
Figure 2I:
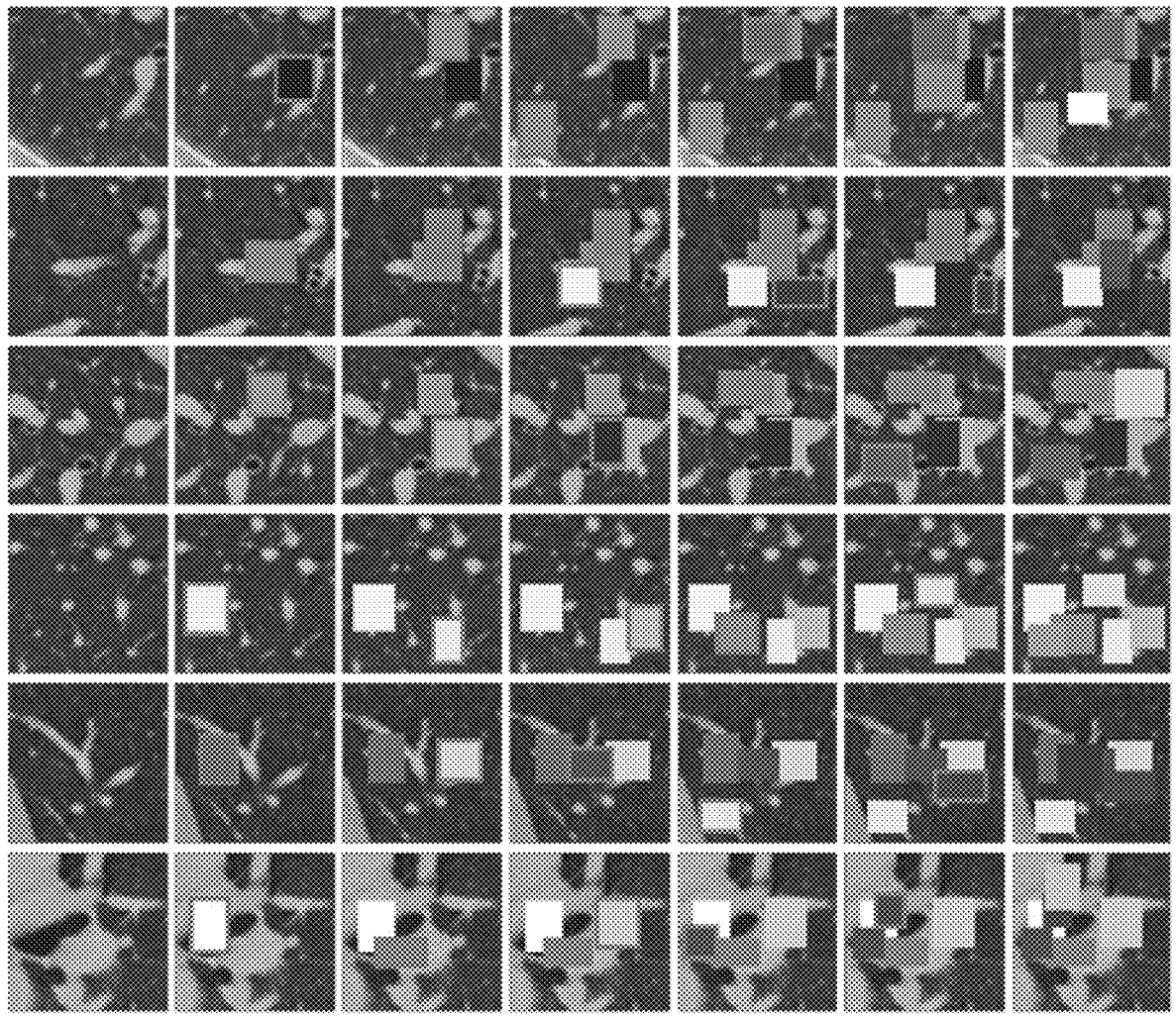

At FIG. 2D an inner-cutout transformation is depicted, via the operations depicted at columns 235, 236, 237, 238, 239, 240, and 241, resulting in the learning of local continuities of organs via the inner-cutout operation 234.

Each of the processes are illustrated step by step via the columns of the respective FIGS. 2A, 2B, 2C, and 2D, where the first and last columns of each figure denote the original images and the final transformed images, respectively. In local shuffling, a different window (see FIG. 2B) is automatically generated and utilized in each step. The implementation details are described in greater detail below with reference to the Appendix Figures A8, A9, and A10, which provide additional visualizations and detail regarding proposed implementations.

According to the described embodiments, image transformations and learning perspectives are described utilizing the following exemplary operations: First, (1) learning appearance via non-linear transformation, secondly, (2) learning texture via local pixel shuffling, and thirdly, (3) learning context via outer and inner cutouts, each of which are described in greater detail below.

(1) Learning appearance via non-linear transformation: A novel self-supervised training scheme based on nonlinear translation is described, in which the model learns to restore the intensity values of an input image transformed with a set of non-linear functions. The rationale is that the absolute intensity values (e.g., so-called Hounsfield units) in CT scans or relative intensity values in other imaging modalities convey important information about the underlying structures and organs.

The described training scheme thus enables the model to learn the appearance of the anatomic structures present in the images. In order to keep the appearance of the anatomic structures perceivable, the non-linear intensity transformation function is intentionally retained as monotonic, allowing pixels of different values to be assigned with new distinct values.

A smooth and monotonic transformation function is utilized, which is generated from two end points ($P_0$ and $P_3$) and two control points ($P_1$ and $P_2$), defined as follows.

$$B(t)=(1-t)^3P_0+3(1-t)^2tP_1+3(1-t)t^2P_2+t^3P_3, t\in[0,1],$$

where t is a fractional value along the length of the line.

At FIG. 2A, the original CT sub-volume is illustrated at the leftmost column 202 and its transformed variants based on different transformation functions at the columns 203 through 208. The corresponding transformation functions are shown in the top row. Notice that, when $P_0=P_1$ and $P_2=P_3$ the Bezier curve is a linear function (as shown via the second through last Columns 203-208).

Values $P_0=(0, 0)$ and $P_3=(1, 1)$ are set to obtain the increasing function (shown in Columns 2 through 4 at elements 203-205) and the opposite is set to get a decreasing function (shown in Columns 5 through 7 at elements 206-208).

Control points are randomly generated for more variances (shown in Columns 3, 4, 6, 7 at columns 204 through 208). Before applying the transformation functions, in Genesis CT, the Hounsfield units values are clipped within the range of [−1000, 1000] and then each CT scan is normalized to [0, 1], whereas with the Genesis X-ray model, each X-ray is directly normalized to [0, 1] without intensity clipping.

(2) Learning texture via local pixel shuffling: local pixel shuffling is utilized to enrich local variations of a sub-volume without dramatically compromising its global structures, which encourages the model to learn the local boundaries and textures of objects. To be specific, for each input sub-volume, 1,000 windows are randomly selected and then the pixels inside each window are shuffled sequentially.

Mathematically, consider a small window W with a size of m×n. The local-shuffling acts on each window and can be formulated as $\tilde{W}=P\times W\times P'$, where W is the transformed window. Variables P and P' denote permutation metrics with the size of m×m and n×n, respectively. Pre-multiplying W with P permutes the rows of the window W, whereas post-multiplying W with P' results in the permutation of the columns of the window W. The size of the local window determines the difficulty of the proxy task.

In practice, to preserve the global content of the image, the window sizes are kept smaller than the receptive field of the network, so that the network can learn much more robust image representation by "resetting" the original pixels positions. Note that the described is distinguished from prior known techniques which apply patch shuffling as a regularization technique to avoid over-fitting. Further still, local-shuffling within an extent keeps the objects perceivable, benefiting the deep neural network in learning invariant image representations by restoring the original sub-volumes.

As is further depicted at FIG. 2B, local shuffling within an extent keeps the objects perceivable, benefiting the deep neural network in learning invariant image representations by restoring the original sub-volumes. Unlike de-noising and in-painting techniques, the local shuffling transformation shown here does not intend to replace the pixel values with noise, which therefore preserves the identical global distributions to the original sub-volume. Moreover, local-shuffling, beyond benefiting the deep neural network in learning local invariant image representations, further serves as a complementary perspective with global patch shuffling.

(3) Learning context via outer and inner cutouts: Outer-cutout was further devised as a new training scheme for self-supervised learning in which an arbitrary number (≤10) of windows are generated, with various sizes and aspect ratios. The generated windows are then superimposed on top of each other, resulting in a single window of a complex shape.

When applying this merged window to a sub-volume, the sub-volume region inside the window is left exposed and its surrounding (e.g., the outer-cutout) is masked with a random number. Moreover, to prevent the task from being too difficult or even unsolvable, the application of the merged window may further include extensively searching for the optimal size of cutout regions spanning from 0% to 90%, incremented by 10%. Ultimately, the outer-cutout region is limited to be less than ¼ of the whole sub-volume. By restoring the outer-cutouts, the model learns the global geometry and spatial layout of organs in medical images via extrapolating within each sub-volume.

This process is illustrated step by step at FIG. 2C, in which the first and last columns (227 and 233) denote the original sub-volumes and the final transformed sub-volumes, respectively.

The self-supervised learning framework described herein also utilizes the inner-cutout as a training scheme, in which the inner window regions (e.g., inner-cutouts) are masked to leave their surroundings exposed. By restoring the inner-cutouts, the model learns local continuities of organs in medical images via interpolating within each sub-volume. Unlike prior techniques which utilize in-painting as a proxy task by restoring only the central region of the image, the framework as described herein restores the entire sub-volume as the model output.

Examples of inner-cutout are illustrated in FIG. 2D. Similar to outer-cutout, the inner-cutout areas are also limited to be less than ¼ of the whole sub-volume, in order to keep the task reasonably difficult.

The unique properties of Models Genesis are described in detail below, as follows:

(1) Autodidactic-requiring no manual labeling—As described herein, Models Genesis are trained in a self-supervised manner with abundant unlabeled image datasets, demanding zero expert annotation effort. Consequently, Models Genesis are fundamentally different from previously known techniques in which fully supervised transfer learning from ImageNet is used, which offers modest benefits to 3D medical imaging applications as well as that from the existing pre-trained, full-supervised models including I3D, NiftyNet, and MedicalNet approaches, each of which demand a volume of annotation effort to obtain the source models (refer again to the statistics given in Table 1 of FIG. 1A at element 175).

(2) Robust-learning from multiple perspectives—The combined approach as described herein trains Models Genesis from multiple perspectives (appearance, texture, context, etc.), leading to more robust models across all target tasks, as evidenced in FIG. 3 (discussed below), where the combined approach is compared with various individual schemes. This eclectic approach, which incorporates multiple tasks into a single image restoration task, empowers Models Genesis to learn more comprehensive representation.

While most self-supervised methods devise isolated training schemes to learn from specific perspectives (e.g., learning intensity value via colorization, context information via Jigsaw, orientation via rotation, etc.), these methods are reported with mixed results on different tasks. Therefore, using compositions of more than one transformations per image is sometimes utilized in accordance with described embodiments, which has also been experimentally confirmed via the image restoration task.

(3) Scalable-accommodating many training schemes—Consolidated into a single image restoration task, the novel self-supervised schemes described herein share the same encoder and decoder during training. Conversely, had each task required its own decoder, then due to limited memory on GPUs, the framework would have failed to accommodate such a large number of self-supervised tasks. By unifying all tasks as a single image restoration task, any favorable transformation can be easily amended into the described framework, overcoming the scalability issue associated with prior known multi-task learning techniques, such as those where the network heads are subject to the specific proxy tasks.

FIG. 2E depicts Table 2 at element 250 shows that the Genesis CT model is pre-trained on only LUNA 2016 dataset (e.g., the source) and then fine-tuned for five distinct medical image applications (e.g., the targets). These target tasks 251 are selected such that they show varying levels of semantic distance from the source, in terms of organs, diseases, and modalities, which permits for the investigation into the transferability of the pre-trained weights of Genesis CT with respect to the domain distance. The cells checked by "X" 261 denote the properties that are different between the source and target datasets.

(4) Generic-yielding diverse applications: Models Genesis, which is trained via a diverse set of self-supervised schemes, learns a general-purpose image representation that can be leveraged for a wide range of target tasks. Specifically, Models Genesis can be utilized to initialize the encoder for the target classification tasks and to initialize the encoder-decoder for the target segmentation tasks, while the previously known self-supervised approaches are largely focused on providing encoder models only.

As shown below at Table 3 (refer to FIG. 6, element 600), Models Genesis can be generalized across diseases (e.g., nodule, embolism, tumor), organs (e.g., lung, liver, brain), and modalities (e.g., CT and MRI), a generic behavior that use of the described methodologies apart from all previous known techniques where the representation is learned via a specific self-supervised task, and thus lack generality.

Experimental methods—Pre-training Models Genesis: The Models Genesis, as described herein, are pre-trained from 623 Chest CT scans in LUNA 2016 in a self-supervised manner. The reason for not using all 888 scans provided by this dataset was to avoid test-image leaks between proxy and target tasks, allowing the rest of the images to confidently be allowed solely for testing Models Genesis as well as the target models, although Models Genesis are trained from only unlabeled images, involving no annotation shipped with the dataset.

Sub-volumes were first randomly cropped, sized 64×64×32 pixels, from different locations. To extract more informative sub-volumes for training, those which were empty (air) or contain full tissues were intentionally excluded. The Models Genesis 2D are self-supervised pre-trained from LUNA 2016 and ChestX-ray14 using 2D CT slices in an axial view and X-ray images, respectively. For all proxy tasks and target tasks, the raw image intensities were normalized to the [0, 1] range before training. Mean square error (MSE) was utilized between input and output images as an objective function for the proxy task of image restoration. The MSE loss is sufficient for representation learning, although the restored images may be blurry.

When pre-training Models Genesis, each of the transformations are applied on sub-volumes with a pre-defined probability. That being said, the model will encounter not only the transformed sub-volumes as input, but also the original sub-volumes. This design offers two distinct advantages.

Firstly, the model must distinguish original versus transformed images, discriminate transformation type(s), and restore images if transformed. The disclosed self-supervised learning framework, therefore, results in pre-trained models that are capable of handling versatile tasks.

Secondly, since original images are presented in the proxy task, the semantic difference of input images between the proxy and target task becomes smaller. As a result, the pre-trained model can be transferable to process regular/normal images in a broad variety of target tasks.

Experimental methods—Fine-tuning Models Genesis: The pre-trained Models Genesis are adaptable to new imaging tasks through transfer learning or fine-tuning. There are three major transfer learning scenarios: (1) employing the encoder as a fixed feature extractor for a new dataset and following up with a linear classifier (e.g., Linear SVM or Softmax classifier), (2) taking the pre-trained encoder and appending a sequence of fully-connected (fc) layers for target classification tasks, and (3) taking the pre-trained encoder and decoder and replacing the last layer with a 1×1×1 convolutional layer for target segmentation tasks.

For scenarios (2) and (3), it is possible to fine-tune all the layers of the model or to keep some of the earlier layers fixed, only fine-tuning some higher-level portion of the model. The performance of the self-supervised representation was evaluated for transfer learning by fine-tuning all layers in the network. In the following, Models Genesis are examined on five distinct medical applications, covering classification and segmentation tasks in CT and MRI images with varying levels of semantic distance from the source (Chest CT) to the targets in terms of organs 253, diseases 252, and modalities 255 (see Table 2 above) for investigating the transferability of Models Genesis.

(1) Lung nodule false positive reduction (NCC): The dataset for NCC (element 256) is provided by LUNA 2016 and consists of 888 low-dose lung CTs with slice thickness less than 2.5 mm. Patients are randomly assigned into a training set (445 cases), a validation set (178 cases), and a test set (265 cases). The dataset offers the annotations for a set of 5,510,166 candidate locations for the false positive reduction task, wherein true positives are labeled as "1" and false positives are labeled as "0". Performance was evaluated via Area Under the Curve (AUC) score on classifying true positives and false positives.

(2) Lung nodule segmentation (NCS): The dataset for NCS (element 257) is provided by the Lung Image Database Consortium image collection (LIDC-IDRI) and consists of 1,018 cases collected by seven academic centers and eight medical imaging companies. The cases were split into training (510), validation (100), and test (408) sets. Each case is a 3D CT scan and the nodules have been marked as volumetric binary masks. The volumes were re-sampled to 1-1-1 spacing and then extracted a 64×64×32 crop around each nodule. These 3D crops were then used for model training and evaluation. Intersection over Union (IoU) and Dice coefficient scores were adopted to evaluate performance.

(3) Pulmonary embolism false positive reduction (ECC): A database for ECC (element 258) consisting of 121 computed tomography pulmonary angiography (CTPA) scans with a total of 326 emboli was utilized. The dataset was pre-processed and divided at the patient-level into a training set with 434 true positive PE candidates and 3,406 false positive PE candidates, and a test set with 253 true positive PE candidates and 2,162 false positive PE candidates. To conduct a fair comparison with the prior works, candidate-level AUC was computed on classifying true positives and false positives.

(4) Liver segmentation (LCS): The dataset for LCS (element 259) was provided by MICCAI 2017 LiTS Challenge and consists of 130 labeled CT scans, which were split into training (100 patients), validation (15 patients), and test (15 patients) subsets. The ground truth segmentation provides two different labels: liver and lesion. For the experiments, only liver was considered as positive class and others as negative class and the experiment then evaluated segmentation performance using Intersection over Union (IoU) and Dice coefficient scores.

(5) Brain tumor segmentation (BMS): The dataset for BMS (element 260) was provided by BraTS 2018 challenge and consists of 285 patients (210 HGG and 75 LGG), each with four 3D MRI modalities (T1, T1c, T2, and Flair) rigidly aligned. The experiment adopted 3-fold cross validation, in which two folds (consisting of 190 patients) were used for training and one fold (consisting of 95 patients) were used for test. Annotations include background (label 0) and three tumor sub-regions: GD-enhancing tumor (label 4), the peritumoral edema (label 2), and the necrotic and non-enhancing tumor core (label 1). Those with label 0 were considered as negatives and others as positives for the experiment and segmentation performance was evaluated using Intersection over Union (IoU) and Dice coefficient scores.

Experimental methods—Baselines and implementation: For a thorough comparison, three different techniques were utilized to randomly initialize the weights of models: (1) a basic random initialization method based on Gaussian distributions, (2) the Xavier method which initializes weights in a network by drawing them from a distribution with zero mean and a specific variance, and (3) a revised version of the Xavier method called MSRA. Each technique was implemented as uniform, glorot_uniform, and he_uniform, respectively, following the initializers in Keras. Because most of the self-supervised learning methods were initially proposed and implemented in 2D, the two most representative methods were extended into their 3D versions for a fair comparison. In addition, publicly available pre-trained models for 3D transfer learning in medical imaging were examined, including NiftyNet, MedicalNet, and the most influential 2D weights initialization, Models ImageNet. The 13D method was also fine-tuned for the five target tasks because it has been shown to successfully initialize 3D models for lung nodule detection with prior techniques. A 3D U-Net architecture was used in 3D applications and a U-Net architecture was used in 2D applications. Batch normalization was utilized in all 3D/2D deep models.

For proxy tasks, the SGD method with an initial learning rate of 1e0 was used for optimization and ReduceLROnPlateau was utilized to schedule the learning rate, in which, if no improvement was seen in the validation set for a certain number of epochs, the learning rate was then reduced. For target tasks, the "Adam method" was used with a learning rate of 1e-3 was used for optimization, where $\beta_1$=0.9, $\beta_2$=0.999, $\in$=1e-8.

An early-stop mechanism was used on the validation set to avoid over-fitting. Simple yet heavy 3D data augmentation techniques were employed in all five target tasks, including random flipping, transposing, rotating, and adding Gaussian noise. Each method was run ten times on all of the target tasks and then reported were the average, standard deviation, and further present statistical analysis based on an independent two-sample t-test.

In the proxy task, the model is pre-trained using 3D sub-volumes sized 64×64×32, whereas in target tasks, the input is not limited to sub-volumes with certain size. That being said, the pre-trained models can be fine-tuned in the tasks with CT sub-volumes, entire CT volumes, or even MRI volumes as input upon user's need. The flexibility of input size is attributed to two reasons. Firstly, the pre-trained models learn generic image representation such as appearance, texture, and context feature. And secondly, the encoder-decoder architecture is able to process images with arbitrary sizes FIGS. 2F, 2G, 2H, and 2I depict four image transformations, non-linear transformation 299(a), local pixel shuffling transformation 299(b), image outer-cutout transformation 299(c), and image inner-cutout transformation 299(d), in accordance with the described embodiments.

For simplicity and clarity, the transformations are illustrated upon on a 2D CT slice, however, the Genesis Chest CT is trained using 3D sub-volumes directly, transformed in a 3D manner. As depicted, the 3D image transformations, with an exception of non-linear transformation 299(a), cannot be approximated in 2D. For ease of understanding, with respect to the non-linear transformation at 299(a), the image is displayed undergoing different translating functions in Columns 2 through 7 at FIG. 2F. For each of the transformations depicted at 299(b) local-shuffling, 299(c) outer-cutout transformation, and 299(d) inner-cutout transformation, each of the processes are illustrated step by step in columns 2 through 6 of those corresponding transformations, where the first and last columns denote the original images and the final transformed images, respectively. For the local-shuffling transformation 299(b), a different window is automatically generated and used in each step of the transformation, as shown.

Figure 2J:
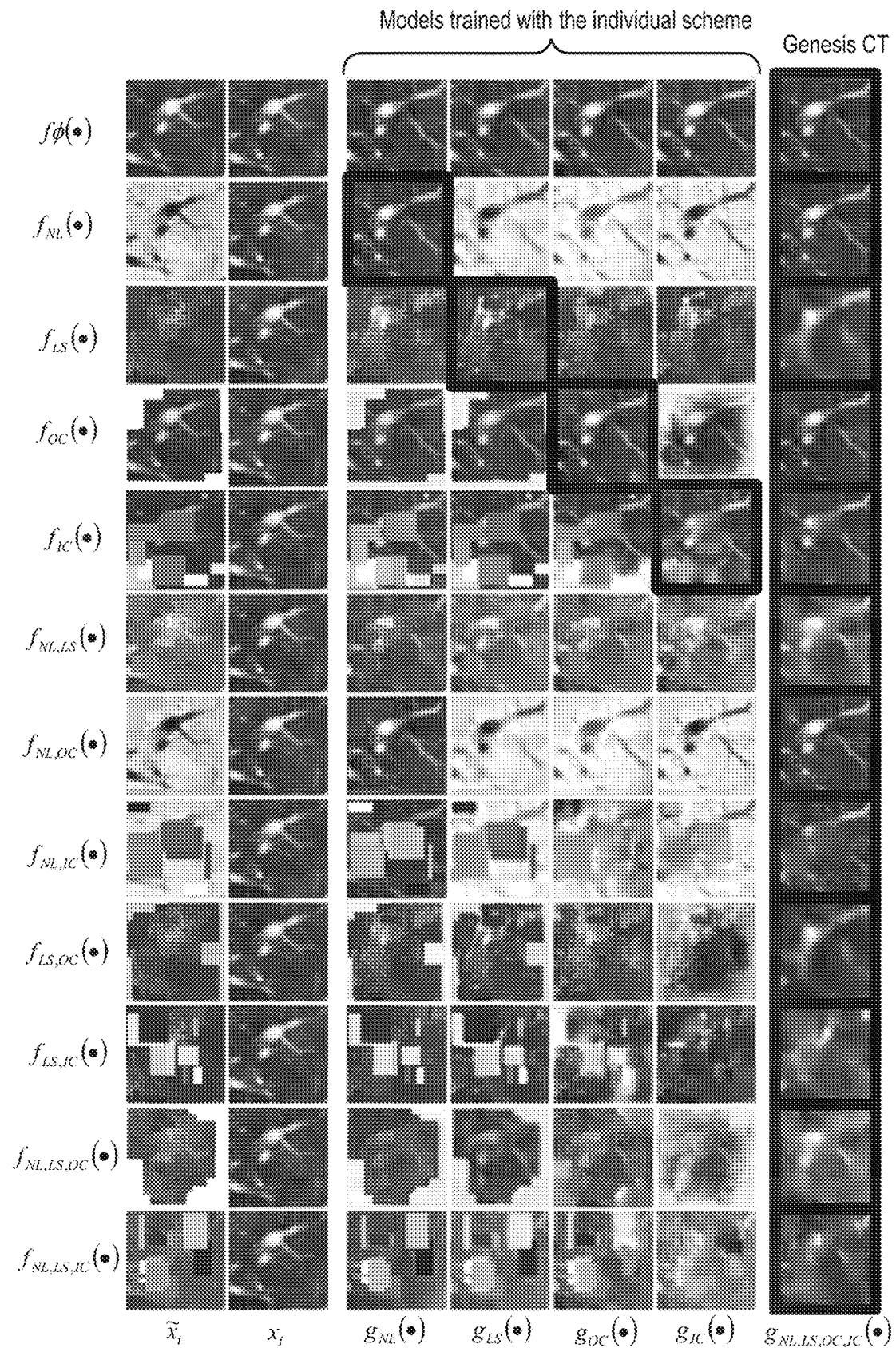
FIGS. 2J and 2K show the qualitative assessment of image restoration quality using Genesis CT and Genesis X-ray, respectively.
Figure 2K:
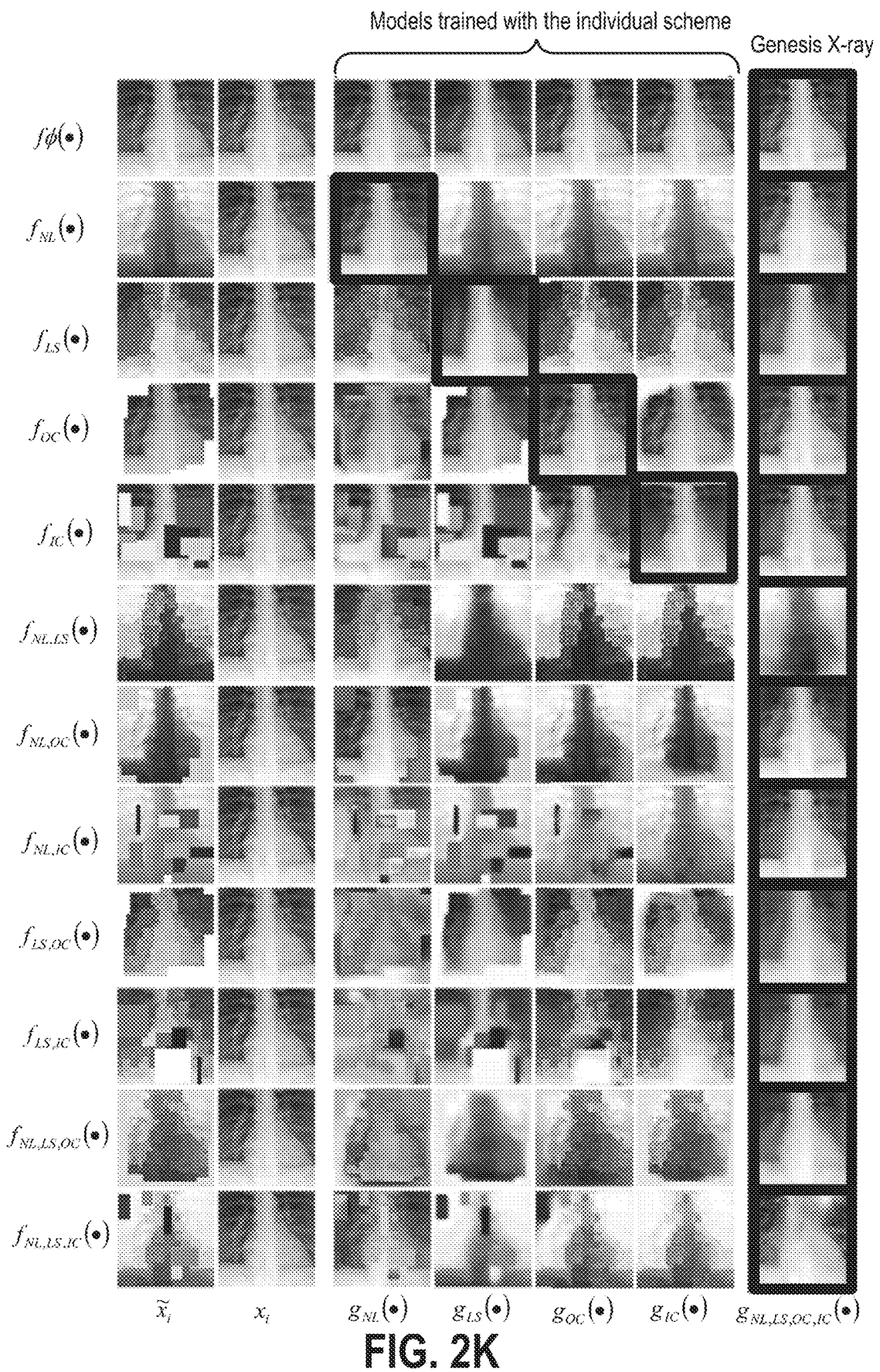

FIGS. 2J and 2K show the qualitative assessment of image restoration quality using Genesis CT and Genesis X-ray, respectively. These models are trained with different training schemes, including four individual schemes (Columns 3 through 6) and a combined scheme (Column 7). As discussed above with respect to FIGS. 1A, 1B, and 1C, each original image $x_i$ can possibly undergo twelve different transformations. The models were tested with all possible twelve transformed images $\tilde{x}_i$. The types of the image transformation $f(\bullet)$ were specified for each row and the training scheme $g(\bullet)$ for each column.

Firstly, it may therefore be observed here that the models trained with individual schemes can restore unseen images (e.g., never before encountered images) that have undergone the same transformation very well (refer to the inner-framed image samples), but fail to handle other transformations. Taking non-linear transformation $f_{NL}(\bullet)$ as an example, any individual training scheme besides non-linear transformation itself cannot invert the pixel intensity from transformed whitish to the original blackish. As expected, the model trained with the combined scheme successfully restores original images from various transformations (refer to the right most framed image samples in the right-hand column).

Secondly, the model trained with the combined scheme shows it is superior to other models even if they are trained with and tested on the same transformation. For example, in the local-shuffling case $f_{LS}(\bullet)$, the image recovered from the local-shuffling pre-trained model $g_{LS}(\bullet)$ is noisy and lacks texture. However, the model trained with the combined scheme $g_{NL,LS,OC,IC}(\bullet)$ generates an image with more underlying structures, which demonstrates that learning with augmented tasks can even improve the performance on each of the individual tasks.

Thirdly, the model trained with the combined scheme significantly outperforms models trained with individual training schemes when restoring images that have undergone seven different combined transformations (Rows 6 through 12). As an example, the model trained with non-linear transformation $g_{NL}(\bullet)$ can only recover the intensity distribution in the transformed image undergone $f_{NL,IC}(\bullet)$, but leaves the inner cutouts unchanged. These observations suggest that the model trained with the proposed unified self-supervised learning framework can successfully learn general anatomical structures and yield promising transferability on different target tasks. The quality assessment of image restoration further confirms the experimental observations described below with respect to FIG. 3, specifically indicating that the combined learning scheme exceeds each individual in transfer learning.

Figure 2L:
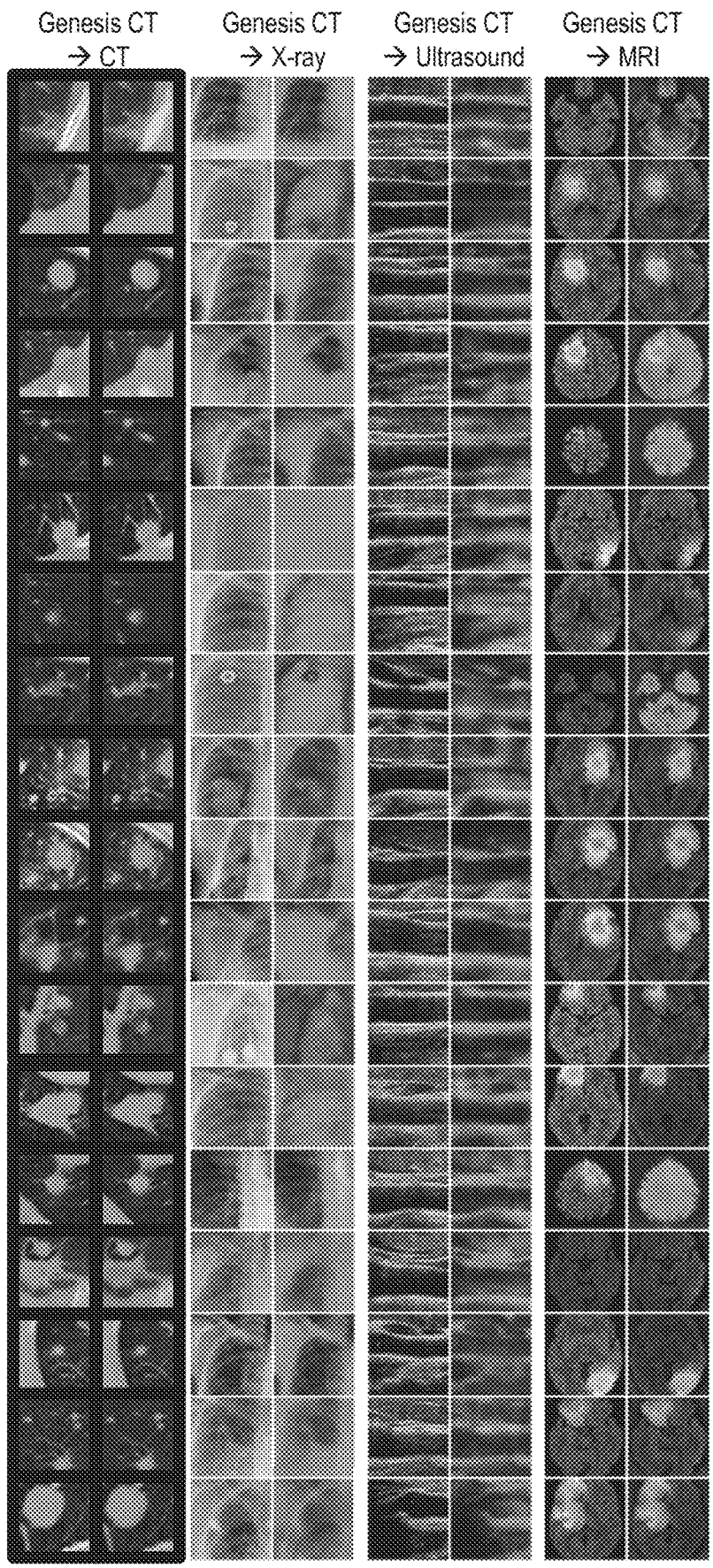
FIGS. 2L and 2M show a visualization of visualize the qualitative assessment of image restoration quality by Genesis CT and Genesis X-ray, respectively, across medical imaging modalities.
Figure 2M:
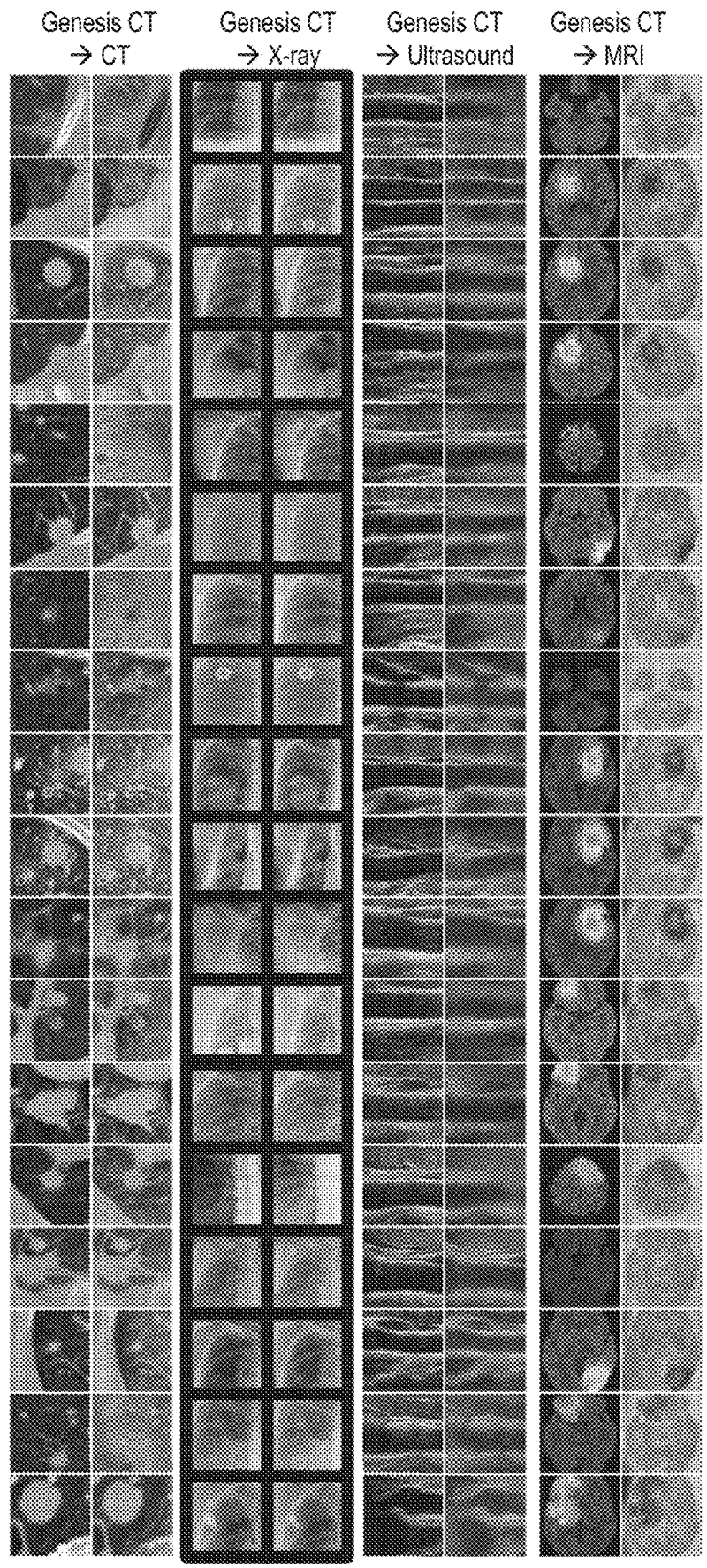

FIGS. 2L and 2M show a visualization of visualize the qualitative assessment of image restoration quality by Genesis CT and Genesis X-ray, respectively, across medical imaging modalities. For testing, the pre-trained model was utilized to directly restore images from LUNA 2016 (CT), ChestX-ray8 (X-ray), CIMT (Ultrasound), and BraTS (MRI). While the models were only trained on single image modality, they nevertheless largely maintain the texture and structures during restoration not only within the same modality (refer to the black frames in the left most side of FIG. 2L and left of center at FIG. 2M), but also across different modalities.

Qualitative assessment of image restoration: As described above, with reference to FIG. 2E, the Genesis CT and Genesis X-ray were pre-trained on LUNA 2016 and Chest Xray8, respectively, using a series of self-supervised learning schemes with different image transformations. FIGS. 2F, 2G, 2H, and 2I provide additional illustrative examples of the four individual transformations (e.g., non-linear transformation at FIG. 2F, local-shuffling transformation at FIG. 2G, outer-cutout transformation at FIG. 2H, and inner-cutout transformation at FIG. 2I). In order to obtain a generic image representation, Models Genesis are trained to restore the original images from their transformed counterparts, in accordance with the described embodiments.

So as to assess the image restoration quality at the time of inference, the transformed images are passed to the models that have been trained with different self-supervised learning schemes, including each of the four individual transformation schemes as well as the combined transformation schemes. In the provided visualizations at FIGS. 2J and 2K, the input images have undergone four individual transformations as well as eight different combined transformations, including the identity mapping (e.g., a direct or no-transformation mapping). Notably, FIGS. 2J and 2K illustrate how the combined scheme can restore the unseen image by handling a variety of transformation (refer to the dark framed boxes at the right-most column of each figure), whereas the models trained with the individual scheme can only restore unseen images that have undergone the same transformation as they were trained on (refer to the dark framed boxes interior to each figure in the top third center). This qualitative observation is consistent with experimental finding described below with reference to FIG. 4, indicating that the combined learning scheme achieves the most robust and superior results over the individual scheme in transfer learning.

Because there is no metric to directly determine the power of image representation, rather than constrain the representation, the disclosed techniques aim to design an image restoration task to let the model learn generic image representation from 3D medical images. In doing so, the definition of a good representation is thus modified. As presented described above, Genesis CT and Genesis X-ray are pre-trained on LUNA 2016 and ChestX-ray8, respectively, using a series of self-supervised learning schemes with different image transformations.

Use of the disclosed embodiments further elevates the power of the pre-trained model by assessing restoration quality on previously unseen patients' images not only from the LUNA 2016 dataset (represented by FIGS. 2F, 2G, 2H, and 2I), but also from different modalities, covering CT, X-ray, and MRI (represented by FIGS. 2L and 2M). The qualitative assessment shows that the described pre-trained model is not merely overfitting on anatomical patterns in specific patients, but indeed can be robustly used for restoring images, thus can be generalized to many target tasks.

FIGS. 2L and 2M illustrate that a qualitative assessment of image restoration quality is provided by Genesis CT and Genesis X-ray, across medical imaging modalities. For these visualizations, the input images are selected from four different medical modalities, covering X-ray, CT, Ultrasound, and MRI. Thus, it is clear from the visualizations at FIGS. 2L and 2M that even though the models are only trained on single image modality, they can largely maintain the texture and structures during restoration not only within the same modality but also across different modalities. These observations suggest that Models Genesis are of a great potential in transferring learned image presentation across diseases, organs, datasets, and modalities.

Figure 3:
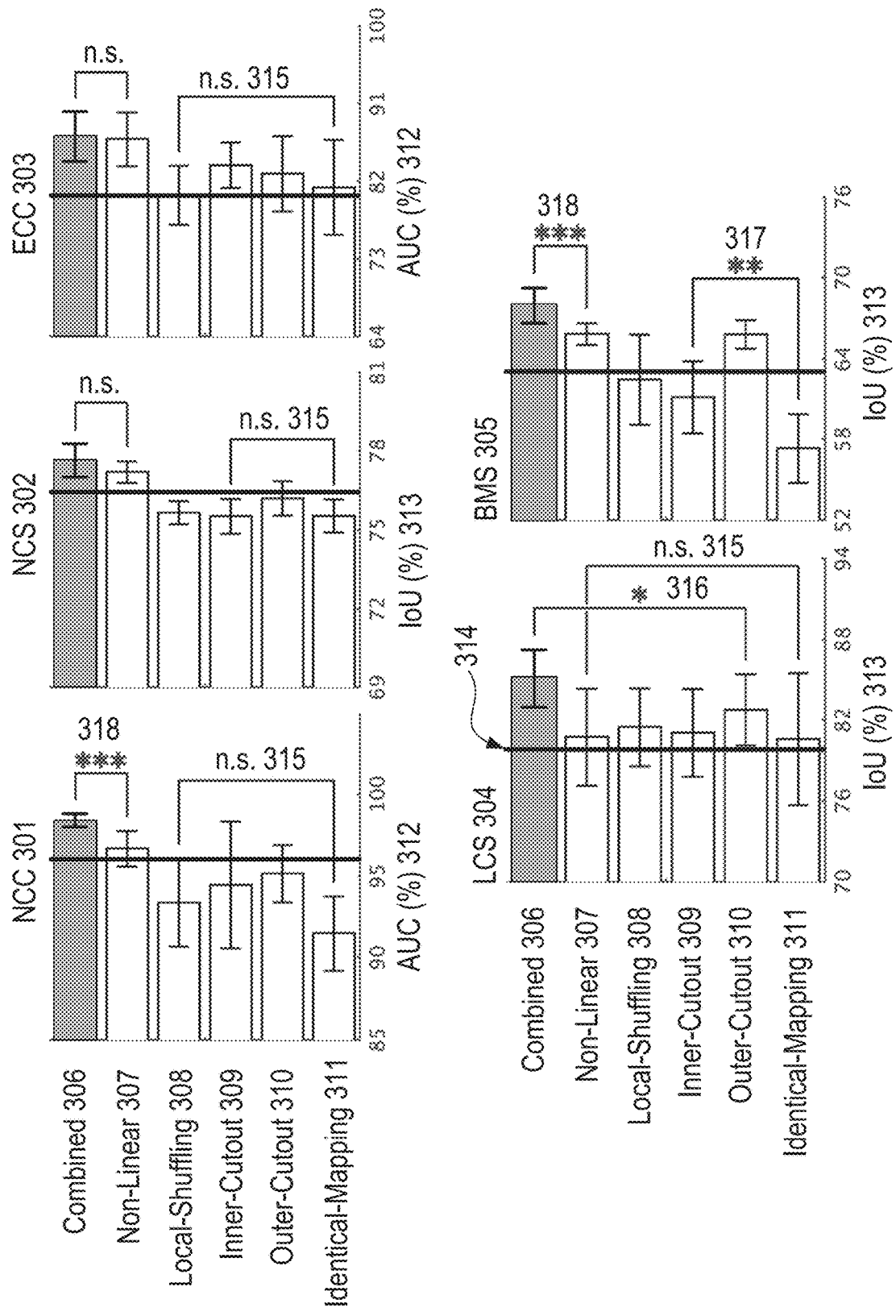
FIG. 3 shows a comparison of the combined training scheme with each of the proposed individual training schemes, in accordance with described embodiments.

FIG. 3 shows a comparison of the combined training scheme 306 with each of the proposed individual training schemes. For all five 3D target tasks, statistical analyses were conducted between the top two training schemes as well as between the bottom two. The error bars represent the 95% confidence interval and the number of stars (* at element 316,  at element 317, and * at element 318) on the bridge indicates how significant two schemes are different from each other measured by p-value (where "n.s." at element 315 stands for "not statistically significant").

As shown here, the training schemes are represented by the charts including combined 306 training schemes, the non-Linear 307 training scheme, the Local-Shuffling 308 training scheme, the Inner-Cutout 309 training scheme, the Inner-Cutout 310 training scheme, and the Identical-Mapping 311 training scheme, represented across the five distinct charts, presented here as NCC at element 301, NCS at element 302, ECC at element 303, LCS at element 304, and BMS at element 305. Each chart is evaluated using either AUC (%) 312 or IoU (%) 313.

The vertical bold line 314 in each task denotes the best performance achieved by random weight initialization. Identical-mapping 311 is considered as a reference because it represents the training scheme without any image transformation. All of the proposed individual training schemes yield either higher or equivalent performances compared with identical-mapping, thereby demonstrating the importance of our suggested image transformations in learning image representation. Although some of the individual training schemes could be favorable for certain target tasks and yield comparable performance with combined training scheme, there is no such clear clue to guarantee that an individual training scheme would consistently offer the best (or the second best) performance on every target task. On the contrary, among all the individual schemes, the combined training scheme consistently achieves the best results across all five of the target tasks.

This robust performance is attributable to the diverse and advanced image representations learned from multiple perspectives and realized by a collection of training schemes.

Figure 4:
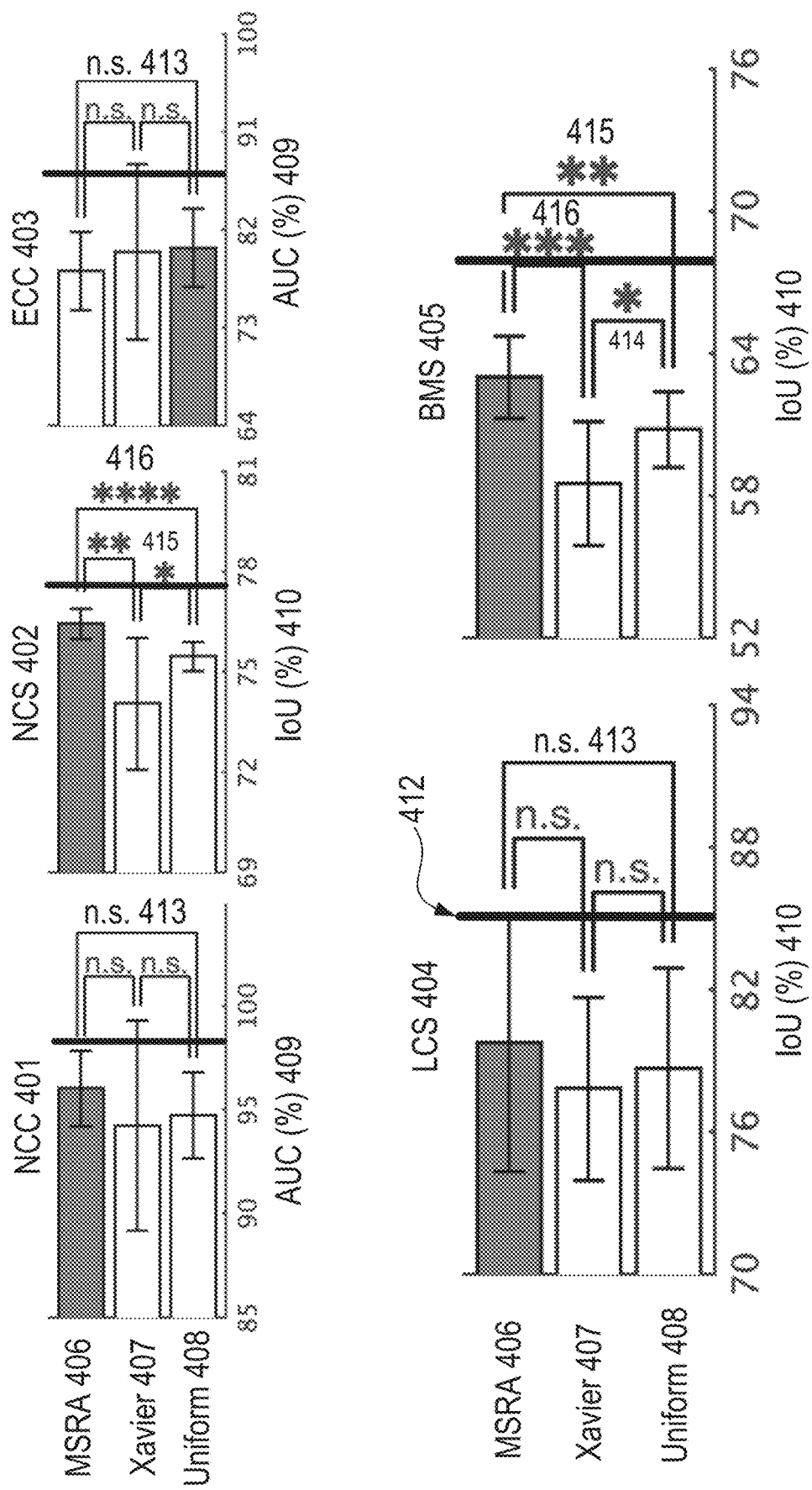
FIG. 4 depicts the Models Genesis with the bold vertical lines as significantly outperforming the initialization with three popular types of random initialization schemes, in accordance with described embodiments.

FIG. 4 depicts the Models Genesis with the bold vertical lines 412 as significantly outperforming the initialization with three popular types of random initialization schemes, including the MSRA method at element 406, Xavier method at element 407, and Uniform method at element 408. When comparing deep model initialization by transfer learning and by controlling mathematical distribution, the former learns more sophisticated image representation but suffers from a domain gap, whereas the latter is task independent yet provides relatively less benefit than the former. Among three out of the five applications, three different types of random distribution reveal no significant (n.s.) difference (element 413) with respect to each other, as evaluated using either AUC (%) 409 or IoU (%) 410.

The various methods, MSRA method at element 406, Xavier method at element 407, and Uniform method at element 408, are represented across the five distinct charts, presented here as NCC at element 401, NCS at element 402, ECC at element 403, LCS at element 404, and BMS at element 405.

Results—An ablation study was used to compare the combined approach with each individual scheme, concluding that the combined approach tends to achieve more robust results and consistently exceeds any other training schemes. The pre-trained model was then taken from the combined approach to present results on five 3D medical applications, comparing them against the state-of-the-art approaches found in recent supervised and self-supervised learning literature.

The combined learning scheme exceeds each individual: Four individual training schemes were devised by applying each of the transformations (i.e., non-linear, local-shuffling, outer-cutout, and inner-cutout) individually to a sub-volume and training the model to restore the original one. Each of these training schemes were compared with identical-mapping, which does not involve any image transformation.

In three out of the five target tasks, as described above at FIG. 3, the model pre-trained by identical-mapping scheme does not perform as well as random initialization. This undesired representation obtained via identical-mapping suggests that without any image transformation, the model would not benefit much from the proxy image restoration task. On the contrary, nearly all of the individual schemes offer higher target task performances than identical-mapping, demonstrating the significance of the four devised image transformations in learning image representation.

Although each of the individual schemes has established the capability in learning image representation, its empirical performance varies from task to task. That being said, given a target task, there is no clear winner among the four individual schemes that can always guarantee the highest performance. A combined scheme was therefore further devised, which applies transformations to a sub-volume with a predefined probability for each transformation and trains a model to restore the original one.

To demonstrate the importance of combining these image transformations together, the combined training schemes was examined against each of the individual ones.

As depicted by the charts set forth at FIG. 3, it is shown that the combined scheme consistently exceeds any other individual schemes in all five target tasks. The combination of different transformations is advantageous because relying on one single training scheme to will not achieve the most robust and compelling results across multiple target tasks.

Therefore, the novel representation learning framework is based on image restoration that allows integrating various training schemes into a single training scheme. A qualitative assessment of image restoration quality, provided in the Appendix, further indicates that the combined scheme is superior over each of the four individual schemes in restoring the images that have been undergone multiple transformations.

Therefore, practice of the disclosed embodiments which provide for a combined scheme that pre-trains a model from multiple perspectives (appearance, texture, context, etc.), empowers models to learn a more comprehensive representation, thereby leading to more robust target models.

Models Genesis outperform learning from scratch: Transfer learning accelerates training and boosts performance, only if the image representation learned from the original (proxy) task is general and transferable to target tasks. Fine-tuning models trained on ImageNet has worked very well in 2D, but for 3D representation learning, there is no availability of such a massive labeled dataset like ImageNet for 2D. As a result, it is still common practice to train 3D model from scratch in 3D medical imaging.

Therefore, to establish the 3D baselines, 3D models are trained with three representative random initialization methods, including naive uniform initialization. In three out of the five 3D medical applications, the results reveal no significant difference among these random initialization methods, as is depicted by the charts set forth at FIG. 4. Although randomly initializing weights can vary by the behaviors on different applications, use of the MSRA method 406, in which the weights are initialized with a specific ReLU-aware initialization, generally provides the most reliable results among all five of the target tasks.

On the other hand, initialization with the pre-trained Genesis Chest CT model achieves improvements over all three random initialization methods by a large margin.

Figure 5:
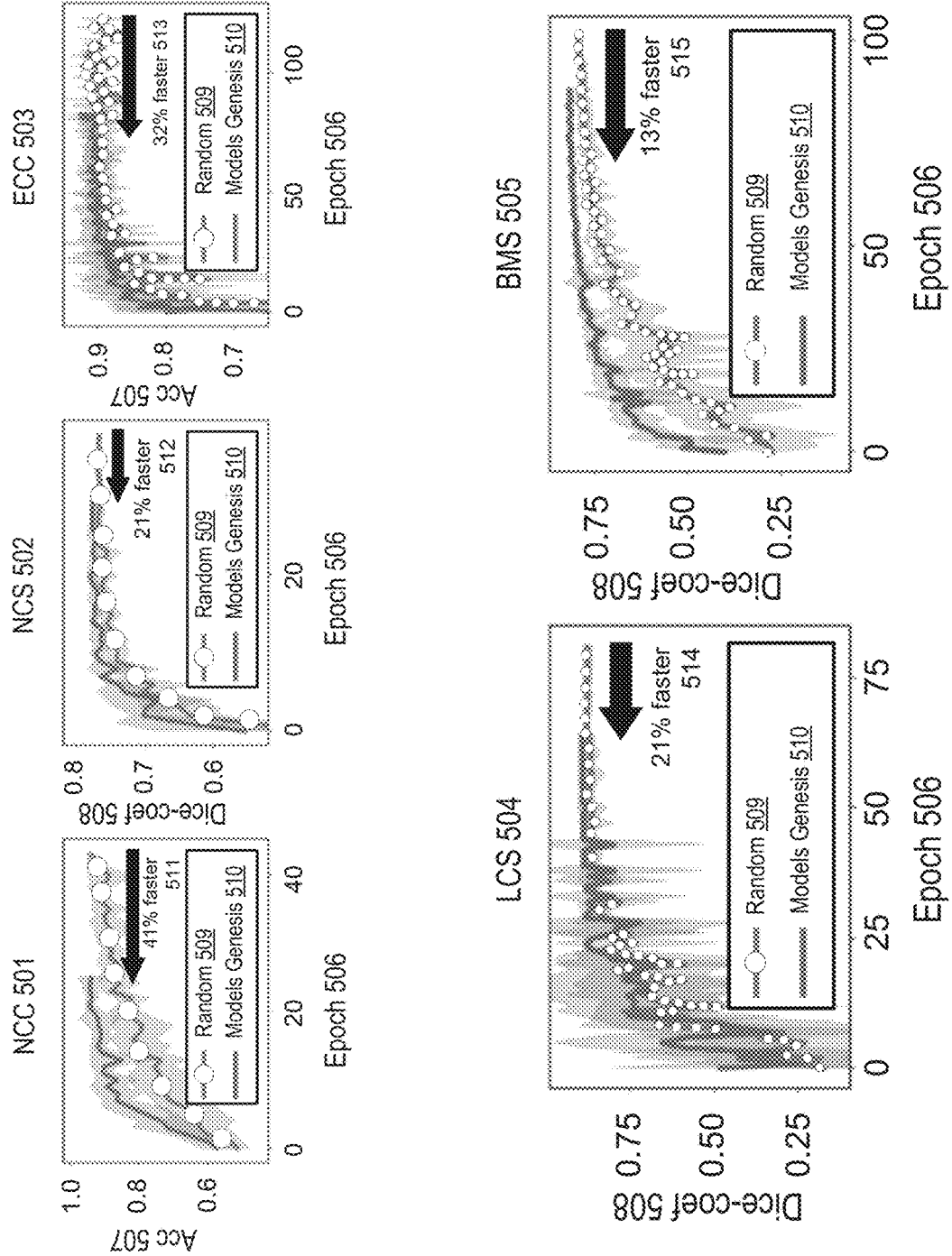
FIG. 5 illustrates the Models Genesis enabling better optimization than learning from scratch, evident by the learning curves for the target tasks of reducing false positives, in accordance with described embodiments.

FIG. 5 illustrates the Models Genesis enabling better optimization than learning from scratch, evident by the learning curves for the target tasks of reducing false positives in detecting lung nodules (NCC) at element 501 and pulmonary embolism (ECC) at element 503 as well as segmenting lung nodule (NCS) at element 503, liver (LCS) at element 504, and brain tumor (BMS) at element 505.

The validation performance is plotted across epochs 506 and averaged by ten trials for each application, in which accuracy and dice-coefficient scores are reported for classification and segmentation tasks, respectively. As seen, initializing with the described pre-trained Models Genesis demonstrates benefits in the convergence speed.

Statistical analysis shows that the performance gain is significant for all the target tasks under study. This suggests that, owing to the representation learning scheme, the initial weights utilized by the disclosed techniques provide a better starting point than the ones generated under particular statistical distributions, while being at least 13% faster as depicted at FIG. 5. More particularly, NCC 501 was observed to be 41% faster (element 511), NCS 502 was observed to be 21% faster (element 512), ECC 503 was observed to be 32% faster (element 513), LCS 504 was observed to be 21% faster (element 514), and BMS 505 was observed to be 13% faster (element 515). This observation has also been widely obtained in 2D model initialization.

Utilization of transfer learning thus facilitates the beneficial transferring of deep features across visual tasks to obtain a semantically more powerful representation, compared with simply initializing weights using different distributions. This is in large part due to the difficulty of adequately initializing these networks from scratch.

For example, a small mis-calibration of the initial weights can lead to vanishing or exploding gradients, as well as poor convergence properties. Comparing with 3D scratch models, the described Models Genesis technique as taught herein serves as a primary source of transfer learning for 3D medical imaging applications.

Further still, in addition to contrasting with the three random 509 initialization methods, the Models Genesis 510 method was further evaluated against existing pre-trained 3D models. In addition to automated data augmentation, Models Genesis provides capabilities for same and cross-domain transfer learning and their impact on the creation of a medical ImageNet, and their capabilities for same-domain and cross-domain transfer learning are further evaluated in the context of existing supervised and self-supervised representation learning approaches in medical imaging.

FIG. 6 depicts Table 3 at element 600 which shows that the Models Genesis leads the best or comparable performance on five distinct medical target tasks over two self-supervised learning approaches (revised in 3D) and three competing publicly available (fully) supervised pre-trained 3D models. For ease of comparison, an AUC score was evaluated for the two classification tasks (e.g., NCC at element 604 and ECC at element 606) and IoU score for the three segmentation tasks (i.e., NCS element 605, LCS element 607, and BMS element 608). All of the results, including the mean and standard deviation (mean±s.d.) across ten trials, reported in the table are evaluated using dataset splitting. For every target task, independent two sample t-tests were performed between the best (bolded at element 629) vs. others, with the gray highlighted boxes (at element 628) depicting those that are not statistically significantly different at p=0:05 level. The footnotes compare experimental results with the state-of-the-art performance for each target task, using the official test set and evaluation metric for the data acquired from competitions.

As shown in Table 3, Models Genesis can be generalized across diseases (e.g., nodule, embolism, tumor), organs (e.g., lung, liver, brain), and modalities (e.g., CT and MRI), a generic behavior that sets us apart from all previous works in the literature where the representation is learned via a specific self-supervised task, and thus lack generality.

Models Genesis surpass existing pre-trained 3D models: The described Models Genesis technique was evaluated with existing publicly available pre-trained 3D models on five distinct medical target tasks.

For instance, as shown in Table 3, the Genesis Chest CT model noticeably contrasts with any other existing 3D models, which have been pre-trained by full supervision 610. Note that, in the liver segmentation task (LCS), Genesis Chest CT is slightly outperformed by MedicalNet because of the benefit that MedicalNet gained from its (fully) supervised pre-training on the LiTS dataset directly. Further statistical tests reveal that the Genesis Chest CT model still yields comparable performance with MedicalNet at p=0.05 level.

For the remaining four target tasks, the Genesis Chest CT model achieves superior performance against all its counterparts by a large margin, demonstrating the effectiveness and transferability of the learned features of Models Genesis, which are beneficial for both classification and segmentation tasks.

More importantly, although the Genesis Chest CT model is pre-trained on Chest CT only, it can generalize to different organs, diseases, datasets, and even modalities. As an example, the target task of pulmonary embolism false positive reduction is performed in Contrast-Enhanced CT scans that can appear differently from the proxy tasks in normal CT scans, and yet, the Genesis Chest CT model achieves a remarkable improvement over training from scratch, increasing the AUC by 7 points.

Further still, the Genesis Chest CT model continues to yield a significant IoU gain in liver segmentation even though the proxy task and target task are significantly different in both, diseases affecting the organs (lung vs. liver) and the dataset itself (LUNA 2016 vs. LiTS 2017).

The Genesis Chest CT model and other existing pre-trained models were further examined using MRI Flair images, which represent the widest domain distance between the proxy and target tasks.

As reported in Table 3 (BMS), Genesis Chest CT 621 yields nearly a 5-point improvement in comparison with random initialization. The increased performance on the MRI imaging task is a particularly strong demonstration of the transfer learning capabilities of the Genesis Chest CT model. To further investigate the behavior of Genesis Chest CT when encountering medical images from different modalities, extensive visualizations are provided in the appendix, including example images from CT, X-ray, Ultrasound, and MRI modalities.

Considering the model footprint, the Models Genesis technique takes the basic 3D U-Net as the backbone, carrying much fewer parameters than the existing open-source pre-trained 3D models.

For example, use of MedicalNet (element 617) with resnet-101 as the backbone for conventional approaches offers the highest performance but comprises 85.75M parameters. The pre-trained I3D (element 615) contains 25.35M parameters in the encoder. The pre-trained NiftyNet (element 616) uses Dense V-Networks as a backbone, consists of only 2.60M parameters, and yet, still does not perform as well as its counterparts in all five target tasks. Taken together, these results indicate that the Models Genesis technique as described herein, with only 16.32M parameters, surpasses all existing pre-trained 3D models in terms of generalizability, transferability, and parameter efficiency.

FIG. 7 illustrates that by initializing with the described Models Genesis, the annotation cost can be reduced by 30%, 50%, 57%, 84%, and 44% for the target tasks NCC, NCS, ECC, LCS, and BMS, respectively. With decreasing amounts of labeled data, Models Genesis (shown here via the upper gray line) retains a much higher performance on all five target tasks (e.g., NCC at element 701, NCS at element 702, ECC at element 703, LCS at element 704, and BMS at element 705), whereas learning from scratch (as depicted via the lower dotted line) fails to generalize. Note that the horizontal lines refer to the performances that can eventually be achieved by Models Genesis and learning from scratch, respectively, when using the entire dataset.

Models Genesis reduce annotation efforts by at least 30%: While critics often stress the need for sufficiently large amounts of labeled data to train a deep model, transfer learning leverages the knowledge about medical images already learned by pre-trained models and therefore requires considerably fewer annotated data and training iterations than learning from scratch. Simulated scenarios using a handful of labeled data were conducted, which allows investigating the power of the Models Genesis techniques described herein for use with transfer learning.

As depicted across the five distinct charts at FIG. 7, the results of training with a partial dataset, demonstrates that fine-tuning the Models Genesis saturates quickly on the target tasks since it can achieve similar performance compared with the full dataset training. Specifically, with only 50%, 5%, 30%, 5%, and 30% of the labeled images, fine-tuning Models Genesis can approximate the performance achieved by learning from scratch using the entire dataset of NCC, NCS, ECC, LCS, and BMS, respectively. These results show that practice of the Models Genesis techniques as described herein can mitigate the lack of labeled images, resulting in a more annotation efficient deep learning in the end.

Furthermore, the performance gap between fine-tuning and learning from scratch is significant and steady over training models with each partial data point. For the lung nodule false positive reduction target task (NCC at element 701 in FIG. 7), using only 49% training data, Models Genesis equal the performance of 70% training data learning from scratch. Therefore, about 30% of the annotation cost associated with learning from scratch in NCC is recovered by initializing with Models Genesis 710 versus random initialization 709, in which Models Genesis recovers the annotation equivalent of 30% fewer labels 711. For the lung nodule segmentation target task (NCS at element 702 in FIG. 7), with 5% training data, Models Genesis 710 can achieve the performance equivalent to learning from scratch using 10% training data when compared with random initialization 709, in which Models Genesis recovers the annotation equivalent of 50% fewer labels 712. Based on this analysis, the cost of annotation in NCS can be reduced by half using Models Genesis compared with learning from scratch. For the pulmonary embolism false positive reduction target task (ECC at element 703 in FIG. 7) suggests that with only 30% training samples, Models Genesis achieves performance equivalent to learning from scratch using 70% training samples, in which Models Genesis recovers the annotation equivalent of 57% fewer labels 713. Therefore, nearly 57% of the labeling cost associated with the use of learning from scratch for ECC could be recovered with our Models Genesis. For the liver segmentation target task (LCS at element 704 in FIG. 7), using 8% training data, Models Genesis equal the performance of learning from scratch using 50% training samples, in which Models Genesis recovers the annotation equivalent of 84% fewer labels 714. Therefore, about 84% of the annotation cost associated with learning from scratch in LCS is recovered by initializing with Models Genesis. For the brain tumor segmentation target task (BMS at element 705 in FIG. 7), with less than 28% training data, Models Genesis achieves the performance equivalent to learning from scratch using 50% training data, in which Models Genesis recovers the annotation equivalent of 44% fewer labels 715. Therefore, nearly 44% of annotation efforts can be reduced using Models Genesis compared with learning from scratch.

Overall, at least 30% of annotation efforts have been reduced by Models Genesis, in comparison with learning a 3D model from scratch in five target tasks. With such annotation-efficient 3D transfer learning paradigm, computer-aided diagnosis of rare diseases, which are severely underrepresented owing to the difficulty of collecting a sizeable amount labeled data, could be eventually actualized.

Figure 8A:
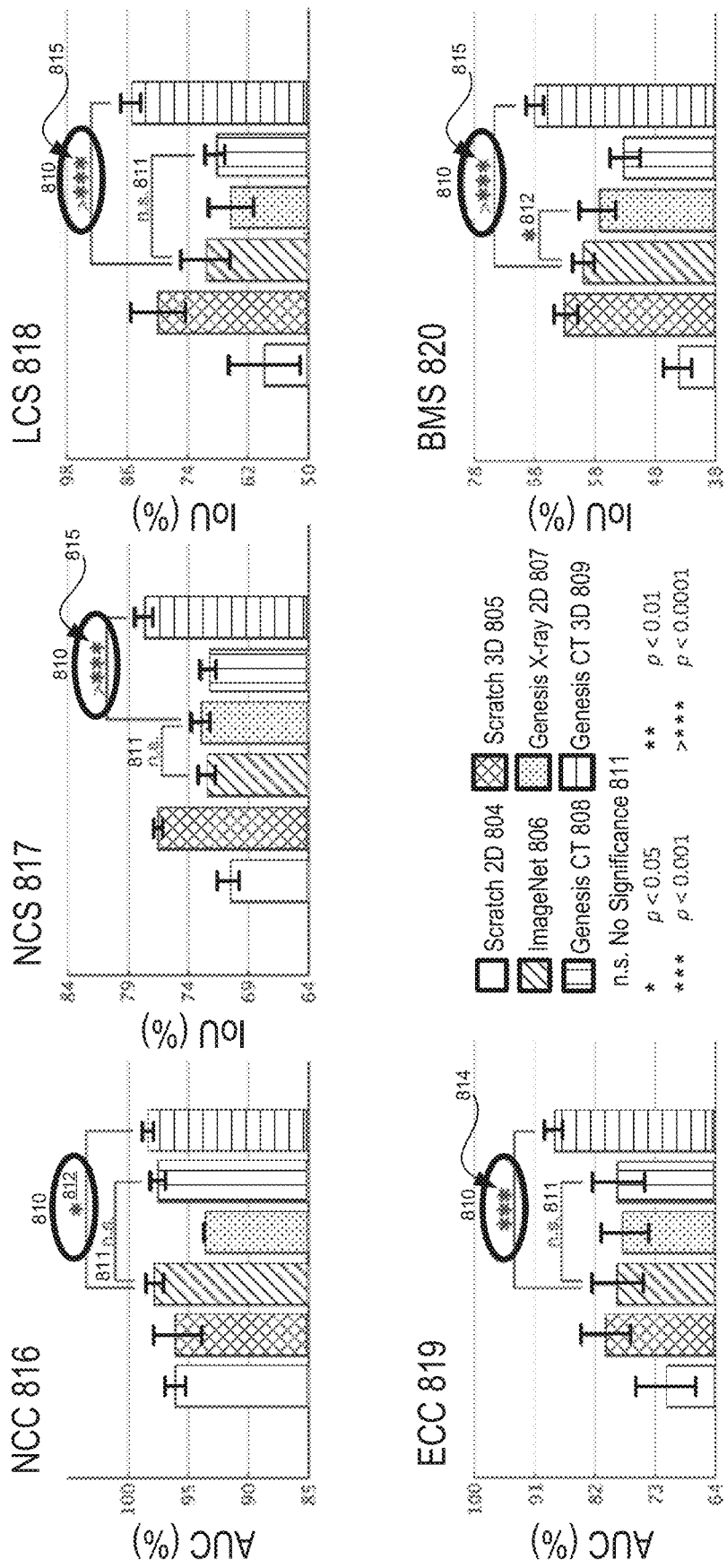
FIG. 8A illustrates that when solving problems in volumetric medical modalities, such as CT and MRI images, 3D volume-based approaches consistently offer superior performance than 2D slice-based approaches empowered by transfer learning, in accordance with described embodiments.

FIG. 8A illustrates that when solving problems in volumetric medical modalities, such as CT and MRI images, 3D volume-based approaches consistently offer superior performance than 2D slice-based approaches empowered by transfer learning.

The statistical analyses (emphasized via the dark black ellipses at element 810) conducted between the highest performance achieved by 3D and 2D solutions. 3D models Trained from scratch do not necessarily outperform their 2D counterparts (see NCC). However, training the same 3D models from the Genesis Chest CT model outperforms all their 2D counterparts, including fine-tuning Models ImageNet as well as fine-tuning our Genesis Chest X-ray and Genesis Chest CT 2D models. The statistical analyses thus confirms the effectiveness of the Genesis Chest CT model in unlocking the power of 3D models. In addition, statistical analyses are further provided between the highest and the second highest performances achieved by 2D models, finding that Models Genesis (2D) offer equivalent performances (n.s.) 811 to Models ImageNet 806 in four out of the five applications.

Notably, the five distinct charts for NCC at element 816, NCS at element 817, LCS at element 818, ECC at element 819, and BMS at element 820 show that Models Genesis outperforms prior known techniques in four out of five instances, notwithstanding Models Genesis operating without the benefit of expert annotation or manual labeling. This performance of Models Genesis CT 3D processing 309 includes superior results when compared with any of Scratch 2D processing 804, ImageNet processing 806, Scratch 3D processing 805, Genesis X-ray 2D processing 807, and Genesis CT processing 808.

Models Genesis consistently tops any 2D/2.5D approaches: The power of 3D models in processing volumetric data is thus presented, which in particular attains improved results with more efficient use of medical images lacking manual labeling or having limited annotation. Besides adopting 3D models, another common strategy to handle limited data in volumetric medical imaging is to reformat 3D data into a 2D image representation followed by fine-tuning pre-trained Models ImageNet 806.

Such an approach increases the training examples by order of magnitude, but it sacrifices the 3D context. It is interesting to note how the Genesis Chest CT model compares with this de facto standard in 2D. Two different methods were implemented to reformat 3D data into 2D input: the regular 2D representation obtained by extracting adjacent axial slices, and the 2.5D representation composed of axial, coronal, and sagittal slices from volumetric data. Both of these 2D approaches seek to use 2D representation to emulate something three dimensional, in order to fit the paradigm of fine-tuning Models ImageNet.

In the inference, classification and segmentation tasks are evaluated differently in 2D. With respect to classification, the model predicts labels of slices extracted from the center locations because other slices are not guaranteed to include objects. With respect to segmentation, the model predicts segmentation mask slice by slice and form the 3D segmentation volume by simply stacking the 2D segmentation maps.

FIG. 8B depicts Table 4 at element 875 which shows the described 3D approach, initialized by Models Genesis, significantly elevates the classification performance compared with 2.5D and 2D approaches in reducing lung nodule and pulmonary embolism false positives. The entries in bold highlight the best results achieved by different approaches. For the 2D slice-based approach, input consisting of three adjacent axial views of the lung nodule or pulmonary embolism and some of their surroundings are extracted. For the 2.5D orthogonal approach, each input is composed of an axial, coronal, and sagittal slice and centered at a lung nodule or pulmonary embolism candidate.

As shown at FIG. 8A, the comparison between 3D and 2D models on five 3D target tasks exposes the difference in performance. Additionally, Table 4 at element 875 of FIG. 8B compares 2D slice-based, 2.5D orthogonal, and 3D volume-based approaches on lung nodule and pulmonary embolism false positive reduction tasks. As evidenced by statistical analyses, the 3D models trained from the Genesis Chest CT model achieve significantly higher average performance and lower standard deviation than 2D models fine-tuned from ImageNet using either 2D or 2.5D image representation.

Nonetheless, the same conclusion does not apply to the models trained from scratch-3D scratch models are outperformed by 2D models in one out of the five target tasks (e.g., refer to NCC in each of FIG. 8A element 816 and FIG. 8B, at Table 4 element 881) and also exhibit an undesirably larger standard deviation. The mixed results of 3D scratch models are attributed to the larger number of model parameters and limited sample size in the target tasks, which together impede the full utilization of 3D context. In fact, the undesirable performance of the 3D scratch models highlights the effectiveness of Genesis Chest CT, which unlocks the power of 3D models for medical imaging.

Stated simply, 3D problems in medical imaging should be solved in 3D directly for optimal results.

Future of the medical ImageNet: In computer vision, at the time this application was written, no self-supervised learning method known to exist outperforms fine-tuning models pre-trained from ImageNet. Therefore, the results in Table 3 (refer to FIG. 6) depicting that (fully) supervised 610 representation learning methods do not necessarily offer higher performances in some 3D target tasks than self-supervised 641 representation learning methods may seem counter-intuitive. This phenomenon is ascribed to the limited amount of supervision used in prior known pre-training techniques or the domain distance (from videos to CT/MRI for I3D). In 2009, when ImageNet had not yet been established, it was challenging to empower a deep model with generic image representation using a small or even medium size of labeled data. The same situation now persists in 3D medical image analysis today. Therefore, despite the outstanding performance of the described Models Genesis, there is no doubt that a large, strongly annotated dataset for medical image analysis, like ImageNet for computer vision is still highly demanded.

Practice and use of the Models Genesis can help to create such a medical ImageNet, because based on a small set of expert annotations, models fine-tuned from Models Genesis will be able to help quickly generate initial rough annotations of wholly unlabeled images for expert review, thus reducing the overall annotation efforts required and accelerating the creation of a large, strongly annotated, medical ImageNet for use by the research community and for use in medical diagnostic technologies.

Stated differently, the Models Genesis techniques as described herein do not serve to replace a large, strongly annotated dataset for medical image analysis, like ImageNet for computer vision, but rather, practice of the described Models Genesis techniques can actually help to create a natively 3D strongly annotated dataset for medical image analysis.

Same-domain vs. cross-domain transfer learning: Same-domain transfer learning is preferred when possible because a relatively smaller domain gap makes the learned image representation more beneficial for target tasks. Same-domain transfer learning strikes as a preferred choice in terms of performance; however, most of the existing medical datasets, with less than a hundred cases, are usually too small for deep models to learn reliable image representation. Therefore, certain embodiments may combine publicly available datasets from similar domains to train modality-oriented models, including the Genesis CT, Genesis MRI, Genesis X-ray, and Genesis Ultrasound models, as well as organ-oriented models, including the Genesis Brain, Genesis Lung, Genesis Heart, and Genesis Liver models. Retrieving a large number of unlabeled images (e.g., from a PACS system, etc) requires the retrieved images to be de-identified. Organizing the de-identified images in a way suitable for deep learning is tedious and laborious. Therefore, large quantities of unlabeled datasets may not be readily available to many target domains. Evidenced by the results in Table 3 (BMS), the Models Genesis techniques have a great potential for cross-domain transfer learning; particularly, utilizing distortion-based approaches (such as non-linear and local-shuffling) to take advantage of relative intensity values (in all modalities) to learn shapes and appearances of various organs.

Data augmentation which is suitable as a transformation: A self-supervised learning framework is specifically proposed to learn image representation by discriminating and restoring images undergoing different transformations. Although, one may argue that the image transformations methodologies set forth herein are interchangeable with existing data augmentation techniques, the reality is not so simple, and thus, in an effort to make the distinction between these two concepts clearer, the following clarifications are further provided.

Notably, it is necessary to assess whether a specific augmentation is practical and feasible for the image restoration task when designing image transformations. Simply introducing data augmentation may problematically make a task ambiguous and thus, lead to degenerate learning. To this end, image transformations were therefore chosen based on two principles.

Firstly, the transformed sub-volume should not be found in the original CT scan. However, it is possible to find a transformed sub-volume that has undergone such augmentations as rotation, flip, zoom in/out, or translation, as an alternative sub-volume in the original CT scan. In this scenario, without additional spatial information, the model would not be able to "recover" the original sub-volume by seeing the transformed one. As a result, only the augmentations that can be applied to sub-volumes at the pixel level rather than the spatial level are elected according to the described embodiments.

Secondly, a transformation should be applicable for specific image properties. The augmentations that manipulate RGB channels, such as color shift and channel dropping, have little effect on CT/MRI images without the availability of color information. Instead, brightness and contrast are promoted into monotonic color curves, resulting in a novel non-linear transformation, explicitly enabling the model to learn intensity distribution from medical images.

After filtering out using the above two principles, the remaining data augmentation techniques are not as many as expected. The disclosed methodologies endeavor to produce learning perspective driven transformations rather than inviting any types of data augmentation into the described framework. A similar phenomenon is also known, in which carefully designed augmentations are superior to autonomously discovered augmentations. This suggests a criterion of transformations driven by learning perspectives, in capturing a compelling, robust representation for 3D transfer learning in medical imaging.

Algorithms that autonomously search for transformations: Two principles are followed when designing suitable image transformations for the self-supervised learning framework.

Potentially, "automated data augmentation" can be considered as an efficient alternative because this line of research seeks to strip researchers from the burden of finding good parameterizations and compositions of transformations manually. Specifically, existing automated augmentation strategies reinforce models to learn an optimal set of augmentation policies by calculating the reward between predictions and image labels. For instance, methodologies may include means for learning how to parameterize and composite the transformations for automated data augmentation, while preserving class labels or null class for all data points. Alternative means include a fast kernel alignment metric for augmentation selection. Such a technique requires image labels for computing the kernel target alignment (as the reward) between the feature kernel and the label kernel. Still further, means for reinforcement learning may be applied to form an algorithm that autonomously searches for preferred augmentation policies, magnitude, and probability for specific classification tasks, wherein the resultant accuracy of predictions and labels is treated as the reward signal to train the recurrent network controller. Additional techniques include the use of uncertainty-based sampling to select the most effective augmentation, but it is based on the highest loss that is computed between predictions and labels.

While the rewards are well defined in each of the above approaches, unfortunately, there is no available metric to determine the power of image representation directly; hence, no reward is readily established for representation learning.

Rather than constrain the representation directly, the disclosed methodology establishes an image restoration task enabled to let the model learn generic image representation from 3D medical images. To achieve this, the definition of a good representation is thus modified into the following: (1) A good representation is one that can be obtained robustly from a transformed input, and that will be useful for restoring the corresponding original input.

Consequently, mean square error (MSE) between the model's input and output is defined as the objective function in the disclosed framework. However, if MSE is adopted as the reward function, the existing automated augmentation strategies will end up selecting identical-mapping. This is because restoring images without any transformation is expected to give a lower error than restoring those with transformations. Evidenced by the charts set forth at FIG. 4, identical-mapping results in a poor image representation. To summarize, the key challenge when employing automated augmentation strategies into the disclosed framework is how to define a proper reward for restoring images, and fundamentally, for learning image representation.

Figure 8C:
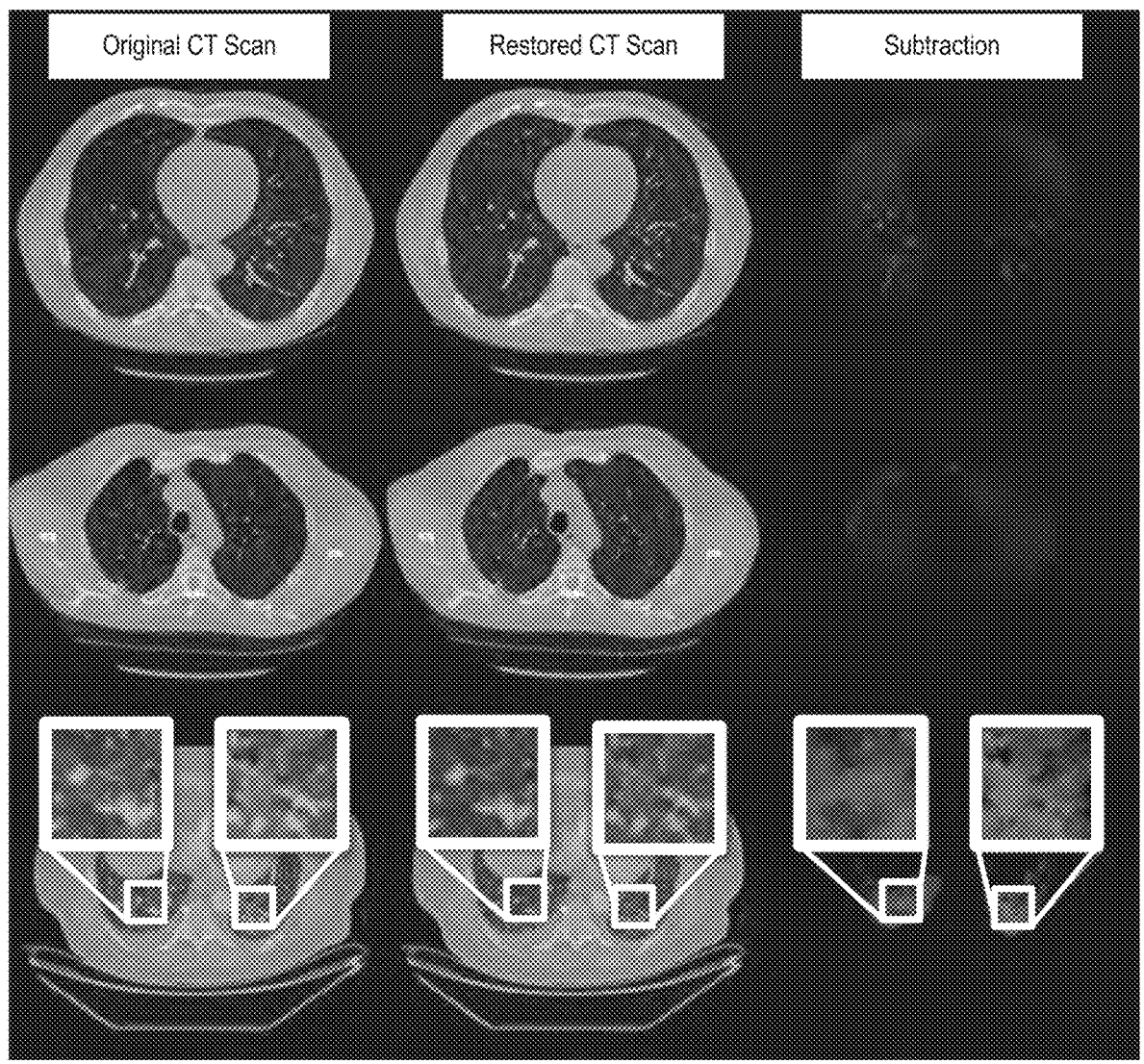
FIG. 8C provides examples of image restoration using Genesis Chest CT, in accordance with described embodiments.

FIG. 8C provides examples of image restoration using Genesis Chest CT, in accordance with described embodiments.

As shown here, unseen CT images (Column 1) are passed to the pre-trained model, obtaining the restored images (Column 2). The difference between input and output has been shown in Column 3. In most of the normal cases, such as those in Rows 1 through 2, Genesis Chest CT performs a fairly reasonable identical-mapping. Meanwhile, for some cases that contain opacity in the lung, as illustrated in Row 3, Genesis Chest CT tends to restore a clearer lung. As a result, the diffuse region is revealed in the difference map automatically. Refer to the zoomed in the region for a better visualization and comparison.

Assessing restoration quality and its relationship to model transferability: The results of transfer learning results discussed above suggest that image restoration is a promising task to learn generic 3D image representation. This also means that image restoration quality has an implicit correlation with model transferability to some extent.

To assess restoration quality, Mean Square Error (MSE) loss is computed with other commonly used loss functions for image restoration, such as Mean Absolute Error (MAE) and Structural Similarity Index (SSIM). All of these calculations are means by which to compute the distance between input and output images, while SSIM concentrates more on the restoration quality in terms of structural similarity than MSE and MAE. Since the publicly available 3D SSIM loss was implemented in PyTorch, to make the comparisons fair, all five target tasks are adapted into PyTorch as well.

Figure 8D:
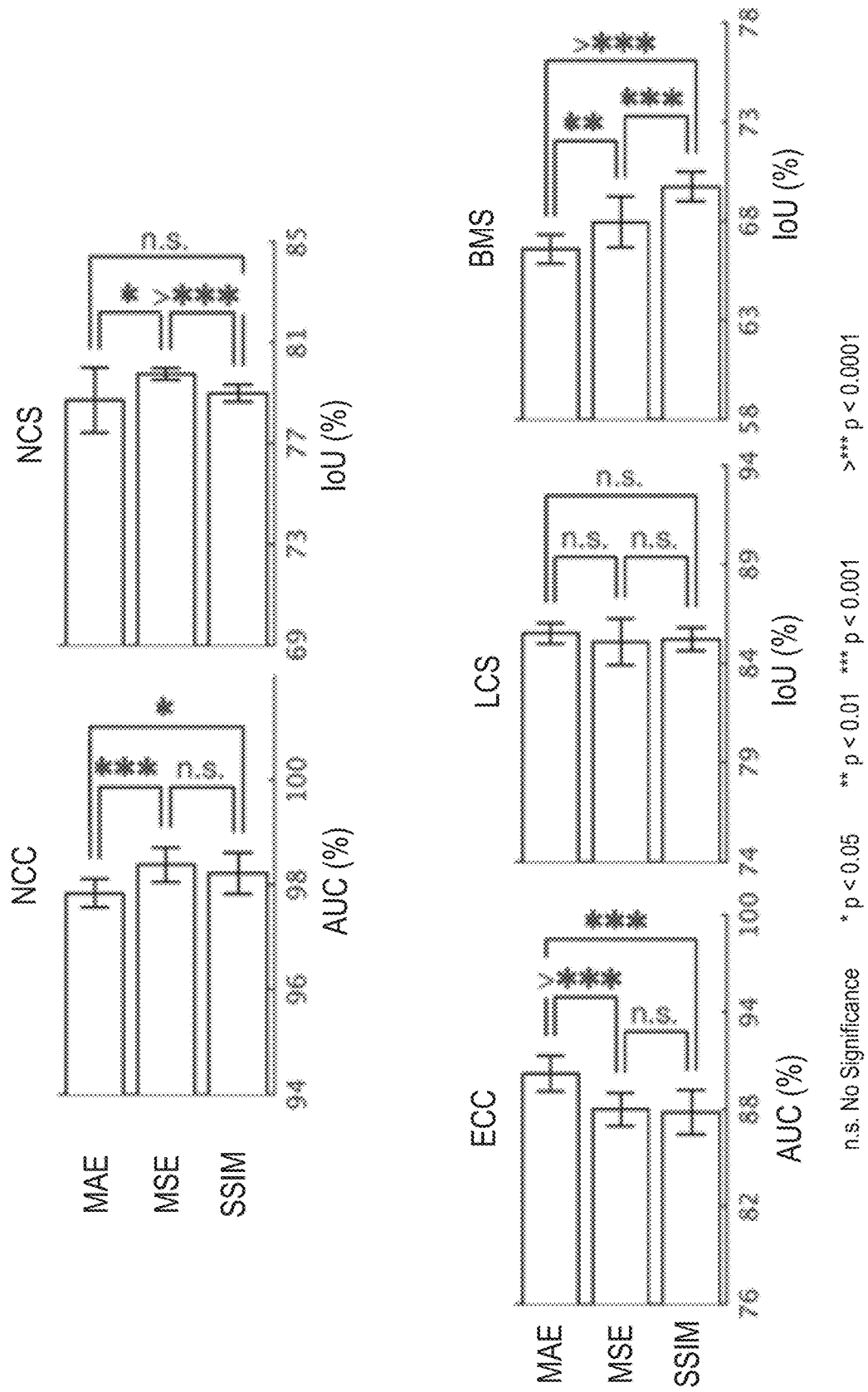
FIG. 8D compares compare three different losses for the task of image restoration, according to the disclosed embodiments.

FIG. 8D compares compare three different losses for the task of image restoration, according to the disclosed embodiments. There is no evidence that the three losses have a decisive impact on the transfer learning results of five target tasks. Note that for this ablation study, all the proxy and target tasks are implemented in PyTorch.

More particularly, the chart shows mixed performances of the five target tasks among the three alternative loss functions. As discussed above, the ideal loss function for representation learning is one that can explicitly determine the power of image representation. However, the three losses explored in this section are implicit, based on the premise that the image restoration quality can indicate a good representation. Further studies with restoration quality assessment and its relationship to model transferability are therefore needed.

Use of Models Genesis for the autonomous detection of infected regions from images: As discussed above, Genesis Chest CT was pre-trained using 623 CT images in the LUNA 2016 dataset. To assess the image restoration quality, the rest of the 265 CT images from the dataset were utilized. Specifically, the original CT images were passed to the pre-trained Genesis Chest CT. To visualize the modifications, the difference maps are further plotted by subtracting the input and output. Since the input images involve no image transformation, most of the restored CT scans (see Rows 1 and 2 of FIG. 8C) can preserve the texture and structures of the input images, only encountering few changes thanks to the identical-mapping training scheme and the skip connections between encoder and decoder. Nonetheless, some failed cases are observed (see Row 3 of FIG. 8C), especially when the input CT image contains diffuse disease, which appears as an opacity in the lung. Genesis Chest CT happens to "remove" those opaque regions and restore a much clearer lung.

This may be due to the fact that the majority of cropped sub-volumes are normal and are being used as ground truth, which empowers the pre-trained model with capabilities of detecting and restoring "novelties" in the CT scans. More specifically, these novelties include abnormal intensity distribution injected by non-linear transformation, atypical texture and boundary injected by local-shuffling, and discontinuity injected by both inner-cutout and the outer-cutout. Based on the surrounding anatomical structure, the model predicts the opaque area to be air, therefore restoring darker intensity values.

This behavior is certainly a "mistake" in terms of image restoration, but it can also be thought of as an attempt to detect diffuse diseases in the lung, which is challenging to annotate due to their unclear boundary. By training an image restoration task, the diseased area will be revealed by simple subtraction of the input and output. More importantly, this suggested detection approach requires zero human annotation, neither image-level label nor pixel-level contour, contrasting from the existing weakly supervised disease detection approaches.

It is for these reasons that the use of deep neural networks in conjunction with transfer learning has become integral to many applications, especially medical imaging applications. This immense popularity of transfer learning is attributed to the learned image representation, which offers convergence speedups and performance gains for most target tasks, in particular, with limited annotated data. In the following section, supervised and self-supervised representation learning are further described.

Supervised representation learning: ImageNet contains more than fourteen million images that have been manually annotated to indicate which objects are present in each image; and more than one million of the images have actually been annotated with the bounding boxes of the objects in the image. Pre-training a model on ImageNet and then fine-tuning the pre-trained model on different medical imaging tasks has seen the most practical adoption in the medical image analysis. To classify the common thoracic diseases from ChestX-ray14 dataset, conventional methods follow the paradigm of "fine-tuning Models ImageNet" by adopting different architectures, such as along with their pre-trained weights. Other representative medical applications include identifying skin cancer from dermatologist level photographs, offering early detection of Alzheimer's Disease, and performing effective detection of pulmonary embolism.

Despite the remarkable transferability of Models ImageNet, pre-trained 2D models offer little benefits towards 3D medical imaging tasks in the most prominent medical modalities (e.g., CT and MRI). To fit this paradigm, 3D imaging tasks have to be reformulated and solved in 2D or 2.5D, thus losing rich 3D anatomical information and inevitably compromising the performance. Annotating 3D medical images at a similar scale with ImageNet requires a significant research effort and budget.

It is currently not feasible to create annotated datasets comparable to this size for every 3D medical application. Consequently, for lung cancer risk malignancy estimation attempts have been made to incorporate 3D spatial information by using Inflated 3D (I3D) methods, trained from the Kinetics dataset, as the feature extractor. Evidenced by Table 3 (refer again to FIG. 6), such prior techniques are not the most favorable choice owing to the large domain gap between the temporal video and medical volume.

This limitation has led to the development of the model zoo in NiftyNet. However, they were trained with small datasets for specific applications (e.g., brain parcellation and organ segmentation), and were never intended as source models for transfer learning. Experimental results shown in Table 3 indicate that NiftyNet models offer limited benefits to the five target medical applications via transfer learning. Other known techniques have pre-trained a 3D residual network by jointly segmenting the objects annotated in a collection of eight medical datasets, resulting in MedicalNet for 3D transfer learning. In Table 3, the pre-trained MedicalNet on five target tasks are examined in comparison with the Models Genesis techniques as described herein.

Prior known pre-trained model techniques require massive, high-quality annotated datasets. However, seldom are there perfectly-sized and systematically-labeled datasets available by which to pre-train a deep model in medical imaging, given that both data and annotations are expensive to acquire. Practice of the disclosed embodiments overcome the above limitations via self-supervised learning, which allows models to learn image representation from abundant unlabeled medical image data with zero human annotation effort.

Self-supervised representation learning: Research into learning image representation from unlabeled data has recently experienced a surge in computer vision, but it is a relatively new trend in modern medical imaging. A key challenge for self-supervised learning is identifying a suitable self-supervision task, that is to say, the generation of input and output instance pairs from the data.

Two of the preliminary studies include predicting the distance and 3D coordinates of two patches randomly sampled from the same brain, identifying whether two scans belong to the same person, and predicting the level of vertebral bodies. Nevertheless, these two works are incapable of learning representation from "self-supervision" because they demand auxiliary information and specialized data collection such as paired and registered images.

By utilizing only the original pixel/voxel information shipped with data, several self-supervised learning schemes have been conducted for different medical applications, such as colorization as a proxy task, wherein color colonoscopy images are converted to gray-scale and then recovered using a conditional Generative Adversarial Network (GAN), or pre-training a stack of denoising auto-encoders, in which the self-supervision was created by mapping the patches with the injected noise to the original patches, or image restoration as a proxy task, where small regions were shuffled within images and then models were allowed to learn to restore the original ones, or a 3D representation learning proxy task that operated by recovering the rearranged and rotated Rubik's cube.

However, each of the above techniques, in both computer vision and medical imaging, are highly specific to the individual target tasks, and therefore, the generalizability and robustness of the learned image representation are not suitable to use across multiple target tasks.

It is therefore provided through the described embodiments the ability to create a collection of generic source models, which are referred to throughout this paper as "Models Genesis," which may be built directly from unlabeled 3D imaging data through the novel unified self-supervised method, for generating powerful application-specific target models through transfer learning.

Moreover, the strong empirical results, surpasses state-of-the-art performance in most of the applications. Through practice of the disclosed Models Genesis techniques, it is therefore feasible to extend the created Models Genesis to application-specific modality-oriented models, such as Genesis MRI and Genesis Ultrasound, as well as organ-oriented models, such as Genesis Brain and Genesis Heart.

Figure 9:
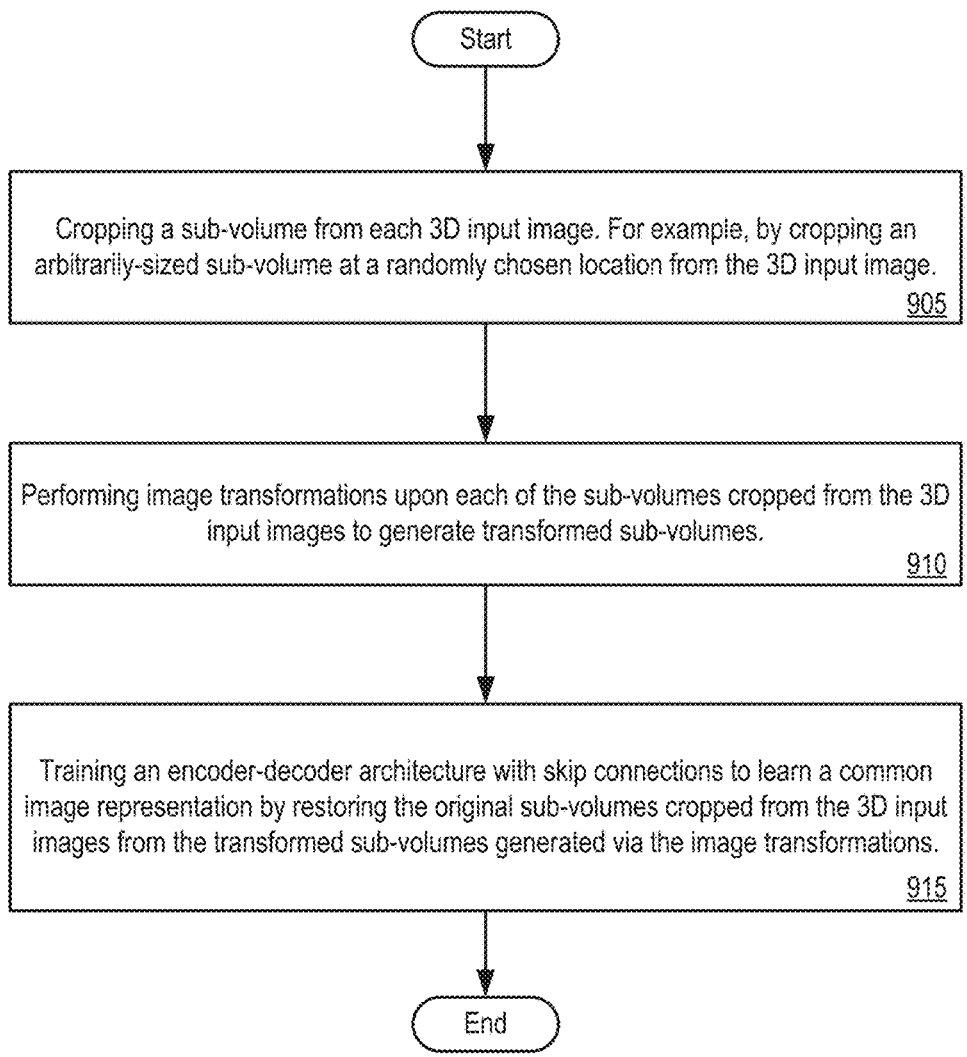
FIG. 9 depicts a flow diagram illustrating a method for learning general-purpose image representations by recovering original sub-volumes of 3D input images from transformed 3D images, in accordance with disclosed embodiments.

FIG. 9 depicts a flow diagram illustrating a method 900 for learning general-purpose image representations by recovering original sub-volumes of 3D input images from transformed 3D images, in accordance with disclosed embodiments. Method 900 may be performed by processing logic that may include hardware (e.g., circuitry, dedicated logic, programmable logic, microcode, etc.), software (e.g., instructions run on a processing device) to perform various operations such as designing, defining, retrieving, parsing, persisting, exposing, loading, executing, operating, receiving, generating, storing, maintaining, creating, returning, presenting, interfacing, communicating, transmitting, querying, processing, providing, determining, triggering, displaying, updating, sending, etc., in pursuance of the systems and methods as described herein. For example, the system 1001 (see FIG. 10) and the machine 1101 (see FIG. 11) and the other supporting systems and components as described herein may implement the described methodologies. Some of the blocks and/or operations listed below are optional in accordance with certain embodiments. The numbering of the blocks presented is for the sake of clarity and is not intended to prescribe an order of operations in which the various blocks must occur.

With reference to the method 900 depicted at FIG. 9, there is a method performed by a system specially configured to learn general-purpose image representations by recovering original sub-volumes of 3D input images from transformed 3D images. Such a system may be configured with at least a processor and a memory to execute specialized instructions which cause the system to perform the following operations:

At block 905, processing logic crops a sub-volume from each 3D input image.

At block 910, processing logic performs image transformations upon each of the sub-volumes cropped from the 3D input images to generate transformed sub-volumes.

At block 915, processing logic trains an encoder-decoder architecture with skip connections to learn a common image representation by restoring the original sub-volumes cropped from the 3D input images from the transformed sub-volumes generated via the image transformations.

According to another embodiment of method 900, training the encoder-decoder architecture to learn the common image representation includes recovering anatomical patterns from the transformed sub-volumes.

According to another embodiment of method 900, cropping the sub-volume from each 3D input image includes cropping an arbitrarily-sized sub-volume at a randomly chosen location from the 3D input image.

According to another embodiment of method 900, cropping the sub-volume from each 3D input image includes cropping the sub-volume from an unlabeled and un-annotated volumetric (3D) Computed Tomography (CT) scan and training the encoder-decoder architecture includes providing as input to the encoder-decoder architecture, the transformed sub-volumes.

According to another embodiment of method 900, performing multiple transformations includes performing at most three of the four transformations selected from the group including: (i) a non-linear image transformation, (ii) a local-shuffling image transformation, (iii) an outer-cutout image transformation, and (iv) an inner-cutout image transformation; and in which the image transformations produce the transformed sub-volumes.

According to another embodiment of method 900, each of the outer-cutout and inner-cutout transformations are mutually exclusive, prohibiting both from being performed against any single cropped sub-volume.

According to another embodiment of method 900, performing the image transformations upon each of the sub-volumes further includes creating, for each cropped sub-volume: an identity mapping sub-volume transformation; and multiple combined transformations formed through a combination of at most three of the four transformations selected from the group including: (i) a non-linear image transformation, (ii) a local-shuffling image transformation, (iii) an outer-cutout image transformation, and (iv) an inner-cutout image transformation.

According to another embodiment of method 900, training the encoder-decoder architecture to learn the common image representation by restoring the original sub-volumes from the transformed sub-volumes includes computing a reconstruction loss (MSE) between a model prediction and a ground truth corresponding to the original sub-volumes prior to having undergone any image transformations.

According to another embodiment, method 900 further includes: fine-tuning the trained encoder architecture for target classification tasks and fine-tuning the trained encoder-decoder architecture for target segmentation tasks.

According to a particular embodiment, there is a non-transitory computer readable storage medium having instructions stored thereupon that, when executed by a system having at least a processor and a memory therein, the instructions cause the system to perform operations for learning general-purpose image representations by recovering original sub-volumes of 3D input images from transformed 3D images. According to such an embodiment, executing the instructions causes the system to perform at least the following operations: cropping a sub-volume from each 3D input image; performing image transformations upon each of the sub-volumes cropped from the 3D input images to generate transformed sub-volumes; and training an encoder-decoder architecture with skip connections to learn a common image representation by restoring the original sub-volumes cropped from the 3D input images from the transformed sub-volumes generated via the image transformations.

Performance of the above instructions provides a pre-trained 3D generic model based on the trained encoder-decoder architecture having learned the common image representation, with the generic model being capable of identifying anatomical patterns in never before seen 3D medical images having no labeling and no annotation. The pre-trained generic models result in improved performance for many specific target tasks based on the implementation needs of the users.

Figure 10:
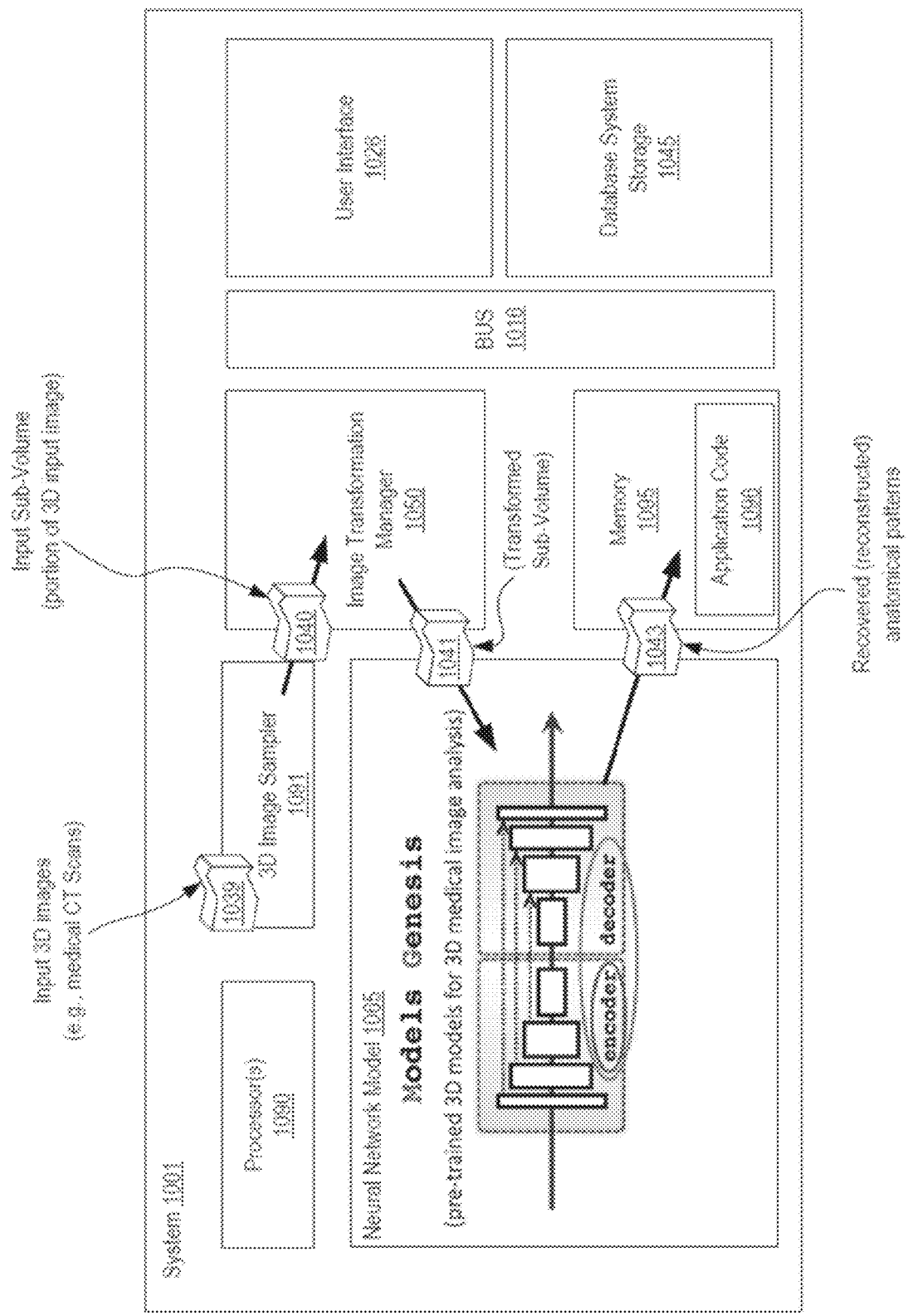
FIG. 10 shows a diagrammatic representation of a system within which embodiments may operate, be installed, integrated, or configured, in accordance with described embodiments.

FIG. 10 shows a diagrammatic representation of a system 1001 within which embodiments may operate, be installed, integrated, or configured. In accordance with one embodiment, there is a system 1001 having at least a processor 1090 and a memory 1095 therein to execute implementing application code 1096. Such a system 1001 may communicatively interface with and cooperatively execute with the benefit of remote systems, such as a user device sending instructions and data, a user device to receive pre-trained Models Genesis as output from the system 1001, or systems within a networked or within a client-server environment, etc.

According to the depicted embodiment, the system 1001, includes the processor 1090 and the memory 1095 to execute instructions at the system 1001. The system 1001 as depicted here is specifically customized and configured to learn general-purpose image representations by recovering original sub-volumes 1043 of 3D input images 1039 from transformed 3D images 1041. According to a particular embodiment, system 1001 is further configured to execute instructions via the processor for cropping a sub-volume 1010 from each 3D input image, for instance, via the 3D image sampler 1091. Such a system 1001 is further configured to execute instructions via the processor for performing image transformations upon each of the sub-volumes cropped (see element 1040) from the 3D input images to generate transformed sub-volumes 1041. The image transformation manager 1050 performs the image transformations upon the cropped sub-volumes. Such a system is further configured to execute instructions via the processor for training an encoder-decoder architecture with skip connections to learn a common image representation by restoring the original sub-volumes cropped from the 3D input images from the transformed sub-volumes generated via the image transformations. For example, the neural network model (NNM) 1065 may apply its encoder and decoder to generate a pre-trained 3D model for 3D medical image analysis.

The model output manager 1085 may further transmit output back to a user device or other requestor, for example, via the user interface 1026, including sending a disease classification 1043 output to a user device or other requestor, or such information may alternatively be stored within the database system storage 1045 of the system 1001.

According to another embodiment of the system 1001, a user interface 1026 communicably interfaces with a user client device remote from the system and communicatively interfaces with the system via a public Internet.

Bus 1016 interfaces the various components of the system 1001 amongst each other, with any other peripheral(s) of the system 1001, and with external components such as external network elements, other machines, client devices, cloud computing services, etc. Communications may further include communicating with external devices via a network interface over a LAN, WAN, or the public Internet.

Figure 11:
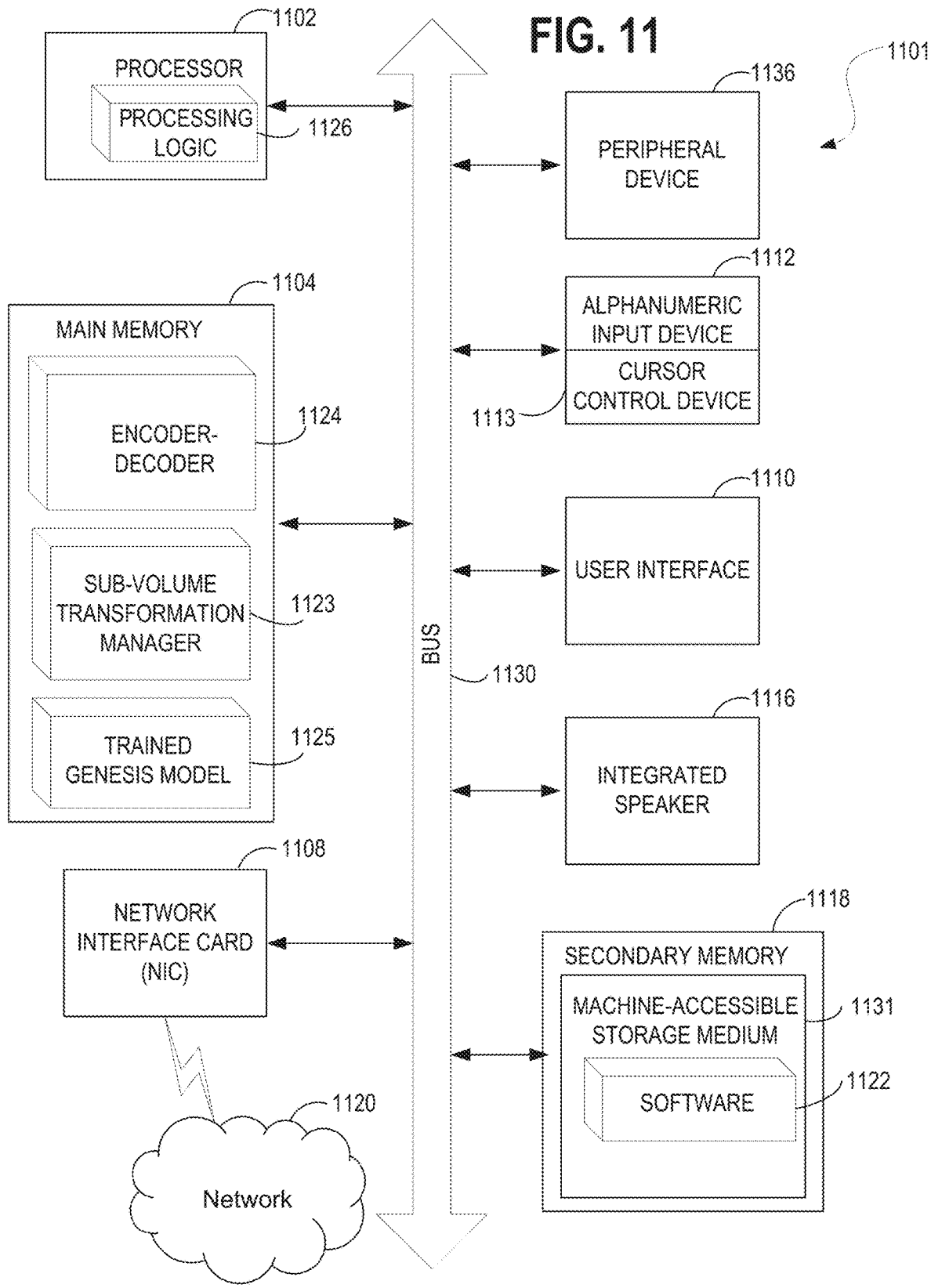
FIG. 11 illustrates a diagrammatic representation of a machine in the exemplary form of a computer system, in accordance with one embodiment.

FIG. 11 illustrates a diagrammatic representation of a machine 1101 in the exemplary form of a computer system, in accordance with one embodiment, within which a set of instructions, for causing the machine/computer system 1101 to perform any one or more of the methodologies discussed herein, may be executed. In alternative embodiments, the machine may be connected (e.g., networked) to other machines in a Local Area Network (LAN), an intranet, an extranet, or the public Internet. The machine may operate in the capacity of a server or a client machine in a client-server network environment, as a peer machine in a peer-to-peer (or distributed) network environment, as a server or series of servers within an on-demand service environment. Certain embodiments of the machine may be in the form of a personal computer (PC), a tablet PC, a set-top box (STB), a Personal Digital Assistant (PDA), a cellular telephone, a web appliance, a server, a network router, switch or bridge, computing system, or any machine capable of executing a set of instructions (sequential or otherwise) that specify and mandate the specifically configured actions to be taken by that machine pursuant to stored instructions. Further, while only a single machine is illustrated, the term "machine" shall also be taken to include any collection of machines (e.g., computers) that individually or jointly execute a set (or multiple sets) of instructions to perform any one or more of the methodologies discussed herein.

The exemplary computer system 1101 includes a processor 1102, a main memory 1104 (e.g., read-only memory (ROM), flash memory, dynamic random access memory (DRAM) such as synchronous DRAM (SDRAM) or Rambus DRAM (RDRAM), etc., static memory such as flash memory, static random access memory (SRAM), volatile but high-data rate RAM, etc.), and a secondary memory 1118 (e.g., a persistent storage device including hard disk drives and a persistent database and/or a multi-tenant database implementation), which communicate with each other via a bus 1130. Main memory 1104 includes an encoder-decoder 1124 (e.g., such as an encoder-decoder implemented via a neural network model) for performing self-learning operations on transformed 3D image sub-volumes, such as the sub-volumes of an image modified and transformed by the sub-volume transformation manager 1123, so as to pre-train and provide a Models Genesis 1125 for use with processing medical imaging in support of the methodologies and techniques described herein. Main memory 1104 and its sub-elements are further operable in conjunction with processing logic 1126 and processor 1102 to perform the methodologies discussed herein.

Processor 1102 represents one or more specialized and specifically configured processing devices such as a microprocessor, central processing unit, or the like. More particularly, the processor 1102 may be a complex instruction set computing (CISC) microprocessor, reduced instruction set computing (RISC) microprocessor, very long instruction word (VLIW) microprocessor, processor implementing other instruction sets, or processors implementing a combination of instruction sets. Processor 1102 may also be one or more special-purpose processing devices such as an application-specific integrated circuit (ASIC), a field programmable gate array (FPGA), a digital signal processor (DSP), network processor, or the like. Processor 1102 is configured to execute the processing logic 1126 for performing the operations and functionality which is discussed herein.

The computer system 1101 may further include a network interface card 1108. The computer system 1101 also may include a user interface 1110 (such as a video display unit, a liquid crystal display, etc.), an alphanumeric input device 1112 (e.g., a keyboard), a cursor control device 1113 (e.g., a mouse), and a signal generation device 1116 (e.g., an integrated speaker). The computer system 1101 may further include peripheral device 1136 (e.g., wireless or wired communication devices, memory devices, storage devices, audio processing devices, video processing devices, etc.).

The secondary memory 1118 may include a non-transitory machine-readable storage medium or a non-transitory computer readable storage medium or a non-transitory machine-accessible storage medium 1131 on which is stored one or more sets of instructions (e.g., software 1122) embodying any one or more of the methodologies or functions described herein. The software 1122 may also reside, completely or at least partially, within the main memory 1104 and/or within the processor 1102 during execution thereof by the computer system 1101, the main memory 1104 and the processor 1102 also constituting machine-readable storage media. The software 1122 may further be transmitted or received over a network 1120 via the network interface card 1108.

Figure 12A:
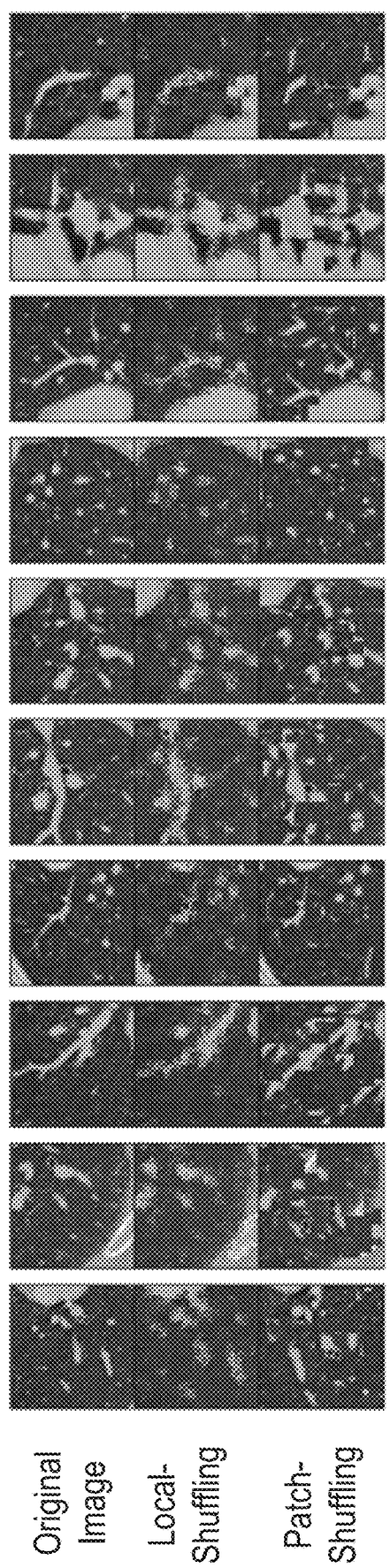
FIG. 12A illustrates a direct comparison between global patch shuffling and the local pixel shuffling technique, in which ten example images have undergone local-shuffling and patch-shuffling independently.

FIG. 12A illustrates a direct comparison between global patch shuffling and the local pixel shuffling technique, in which ten example images have undergone local-shuffling and patch-shuffling independently.

As seen, the overall anatomical structure such as individual organs, blood vessels, lymph nodes, and other soft tissue structures are preserved in the transformed image through local-shuffling.

Figure 12B:
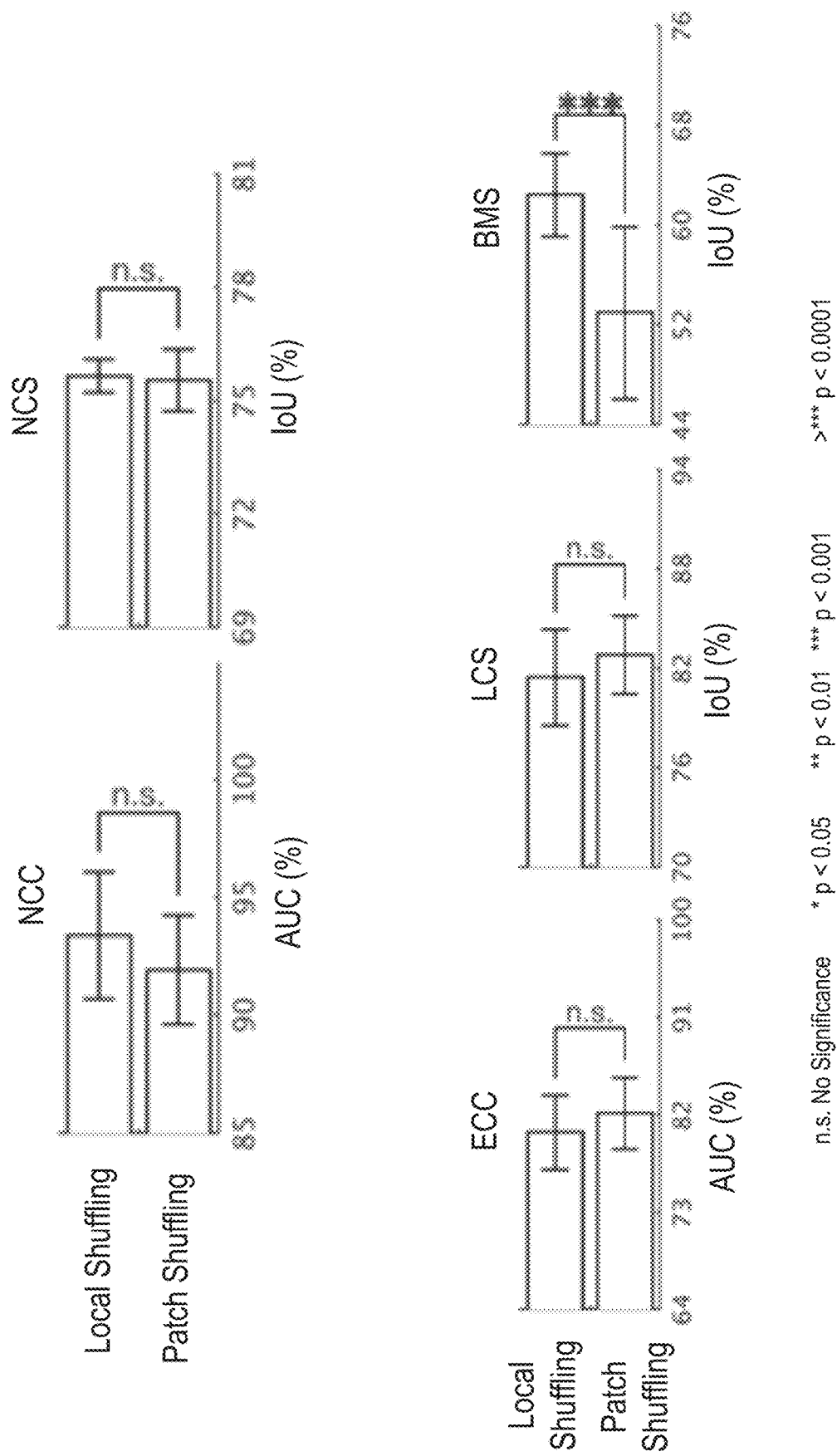
FIG. 12B presents the performance on five target tasks, showing that models pre-trained by the local-shuffling technique noticeably outperform those pre-trained by the patch-shuffling technique for cross-domain transfer learning (BMS)

FIG. 12B presents the performance on five target tasks, showing that models pre-trained by the local-shuffling technique noticeably outperform those pre-trained by the patch-shuffling technique for cross-domain transfer learning (BMS).

Implementation details of revised baselines: This work is among the first effort to create a comprehensive benchmark for existing self-supervised learning methods for 3D medical image analysis. The described techniques extend the six most representative self-supervised learning methods into their 3D versions, including De-noising, In-painting, Jigsaw, and patch-shuffling. These methods were originally introduced for the purpose of 2D imaging. On the other hand, the most recent 3D self-supervised method learns representation by playing a Rubik's cube, re-implemented here for the unique use case and customized to support the ability of generating self-taught generic models without requiring manual labeling of input images. All of the models are pre-trained using the LUNA 2016 dataset with the same sub-volumes extracted from CT scans as the disclosed models. The detailed implementations of the baselines are elaborated in the following sections.

Extended 3D De-noising: With the use of the disclosed 3D De-noising technique, which is inspired by its 2D counterpart, the model is trained to restore the original sub-volume from its transformed one with additive Gaussian noise (e.g., randomly sampling $\sigma \in [0,0.1]$). To correctly restore the original sub-volume, models are required to learn Gabor-like edge detectors when denoising transformed sub-volumes. Following the proposed image restoration training scheme, the auto-encoder network is replaced with a 3D U-Net, wherein the input is a 64×64×32 sub-volume that has undergone Gaussian noise and the output is the restored sub-volume. The L2 distance between input and output is used as the loss function.

Extended 3D In-painting: With the use of the disclosed 3D In-painting technique, which is inspired by its 2D counterpart, the model is trained to in-paint arbitrary cutout regions based on the rest of the sub-volume. A qualitative illustration of the image in-painting task is shown in the right panel of FIG. 13A. To correctly predict missing regions, networks are required to learn local continuities of organs in medical images via interpolation. Unlike the original in-painting, the adversarial loss and discriminator are excluded from the implementation of the 3D version because our primary goal is to empower models with generic representation, rather than generating sharper and realistic sub-volumes. The generator is a 3D U-Net, consisting of an encoder and a decoder. The input of the encoder is a 64×64×32 sub-volume that needs to be in-painted. Their decoder works differently than our inner-cutout because it predicts the missing region only, and therefore, the loss is just computed on the cutout region.

Extended 3D Jigsaw: With the use of the disclosed 3D Jigsaw technique, which is inspired by its 2D counterpart, puzzles are created by sampling a 3×3×3 grid of 3D patches. Then, these patches are shuffled according to an arbitrary permutation, selected from a set of predefined permutations. This set with size P=100 is chosen out of the (3×3×3) !possible permutations, by following the Hamming distance based algorithm, and each permutation is assigned an index. As a result, the problem is cast as a P-way classification task, i.e., the model is trained to recognize the applied permutation index, allowing us to solve the 3D puzzles efficiently. We build the classification model by taking the encoder of 3D U-Net and appending a sequence of fc layers. In the implementation, the cross-entropy loss of the list of extracted puzzles is minimized.

Extended 3D Patch-shuffling: With the use of the disclosed 3D Patch-shuffling technique, which is inspired by its 2D counterpart, the model learns image representation by restoring the image context. Given a sub-volume, two isolated small 3D patches are randomly selected and their context swapped. The length, width, and height of the 3D patch is set to be proportional to those in the entire sub-volume by 25% to 50%. Repeating this process for T=10 times can generate the transformed sub-volume (see examples in FIG. 12A). The model is trained to restore the original sub-volume, where L2 distance between input and output is used as the loss function.

To process volumetric input and ensure a fair comparison with other baselines, their U-Net is replaced with 3D U-Net architecture, where the encoder and decoder serve as analysis and restoration parts, respectively.

Extended 3D DeepCluster: With the use of the disclosed 3D DeepCluster technique, which is inspired by its 2D counterpart, deep features having been iteratively clustered are then extracted sub-volumes by k-means and use the subsequent assignments as supervision to update the weights of the model. Through clustering, the model can obtain useful general-purpose visual features, requiring little domain knowledge and no specific signal from the inputs. An original AlexNet/VGG architecture was therefore replaced with the encoder of 3D U-Net to process 3D input sub-volumes. The number of clusters that works best for 2D tasks may not be a good choice for 3D tasks. To ensure a fair comparison, this hyper-parameter was extensively tuned in {10; 20; 40; 80; 160; 320} and finally set to 260 from the narrowed down search space of {240; 260; 280}. Unlike ImageNet models for 2D imaging tasks, there is no available pre-trained 3D feature extractor for medical imaging tasks; therefore, the model weights were initially randomized at the beginning.

For the disclosed Models Genesis, the first generic 3D pre-trained models, could potentially be used as the 3D feature extractor and co-trained with 3D DeepCluster.

Rubik's cube: The Rubik's cube technique was implemented which consists of cube rearrangement and cube rotation. Like playing a Rubik's cube, this proxy task enforces models to learn translational and rotational invariant features from raw 3D data. Given a sub-volume, the 3D data was partitioned into a 2×2×2 grid of cubes. In addition to predicting orders (3D Jigsaw), this proxy task permutes the cubes with random rotations, forcing models to predict the orientation. Following the original paper, the directions for cube rotation were then limited (e.g., only allowing 180 horizontal and vertical rotations, to reduce the complexity of the task. The eight cubes are then fed into a Siamese network with eight branches sharing the same weight to extract features. The feature maps from the last fully-connected or convolution layer of all branches are concatenated and given as input to the fully-connected layer of separate tasks (e.g., cube ordering and orienting), which are supervised by permutation loss and rotation loss, respectively, with equal weights.

Figure 13A:
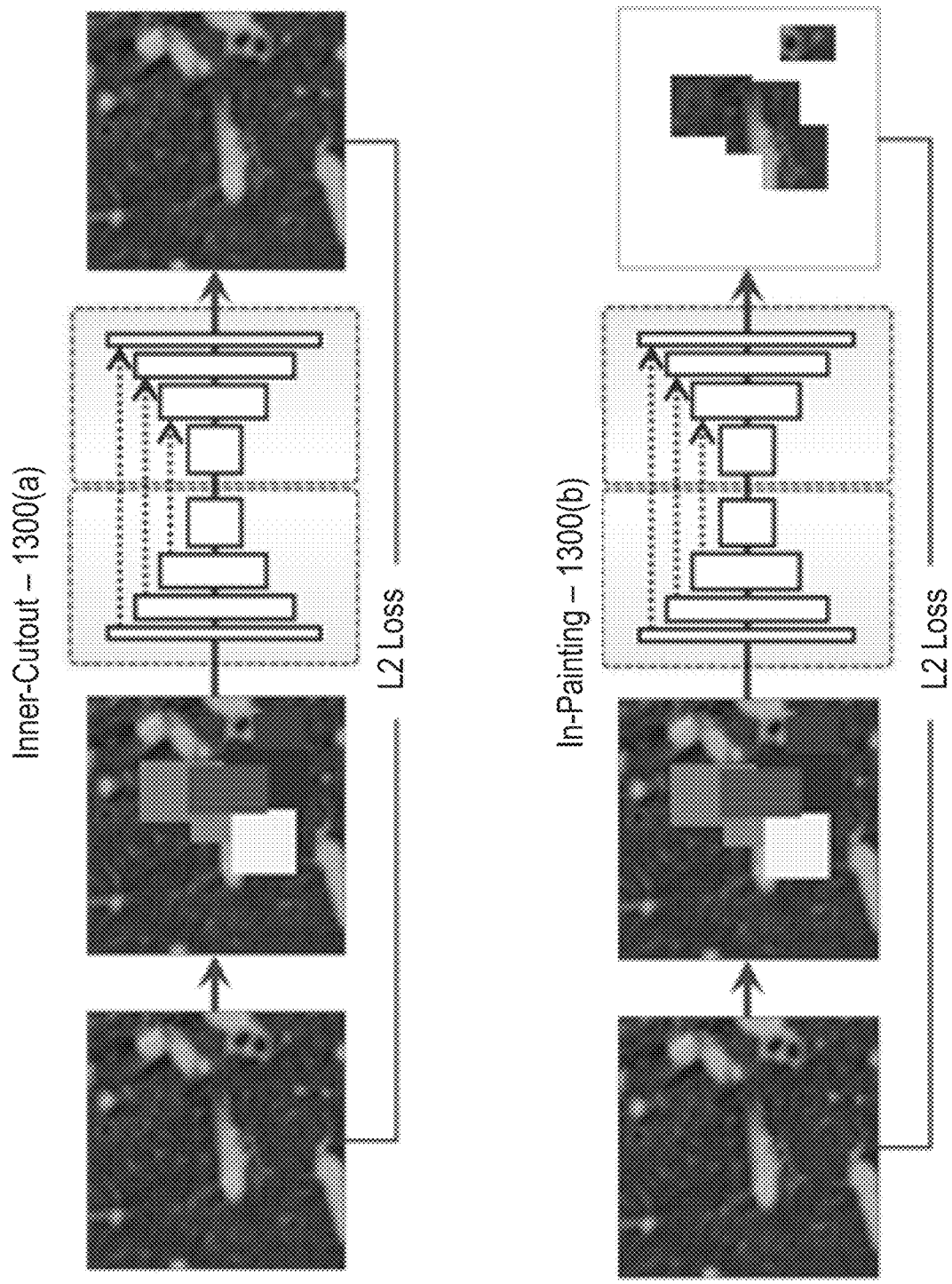
FIG. 13A illustrates a direct comparison between image in-painting and the disclosed inner-cutout technique, in accordance with described embodiments.

FIG. 13A illustrates a direct comparison between image in-painting and the disclosed inner-cutout technique, in accordance with described embodiments.

Notably, the inner-cutout at 1300(*a*) contrasts with the in-painting technique 1300(*b*), in which the model in the former scheme computes loss on the entire image and the model in the latter scheme computes loss only for the cutout area.

Figure 13B:
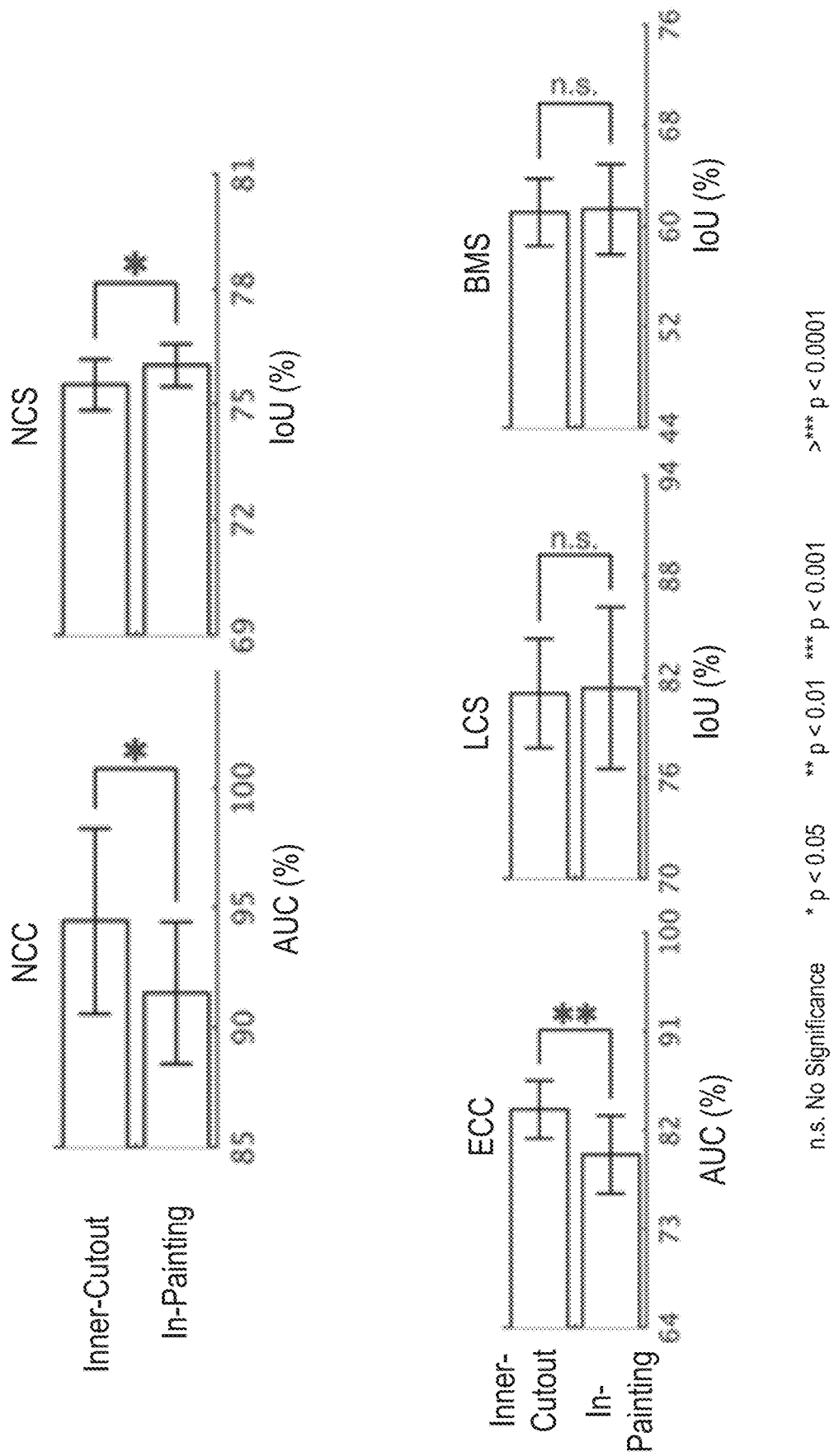
FIG. 13B presents the performance on five target tasks, showing that inner-cutout is better suited for target classification tasks (e.g., NCC and ECC), while in-painting is more helpful for target segmentation tasks (e.g., NCS, LCS, and BMS)

FIG. 13B presents the performance on five target tasks, showing that inner-cutout is better suited for target classification tasks (e.g., NCC and ECC), while in-painting is more helpful for target segmentation tasks (e.g., NCS, LCS, and BMS).

Configurations of publicly available models: For publicly available models, their proxy tasks were not re-trained. Rather implementation of the disclosed techniques simply endeavored to find the best hyper-parameters for each of them in target tasks. The disclosed Models Genesis were compared in a user perspective, which might seem to be unfair in a research perspective because many variables are asymmetric among the competitors, such as programming platform, model architecture, number of parameters, etc. However, the goal was to experiment with existing ready-to-use pre-trained models under different medical tasks; therefore, it was presumed that all of the publicly available models and their configurations have been carefully composed to the optimal setting.

NiftyNet: The effectiveness of fine-tuning from NiftyNet was examined in five target tasks. NiftyNet was not initially designed for transfer learning but is one of the few publicly available supervised pre-trained 3D models. The NiftyNet model has been considered as the baseline in these experiments because it has also been pre-trained on the chest region in CT modality and applied an encoder-decoder architecture that is similar to work leading to the disclosed techniques. The pre-trained weights of the dense V-Net architecture provided by NiftyNet were directly adopted such that they carry a smaller number of parameters than the disclosed 3D U-Net (e.g., 2.60M vs. 16.32M). For target classification tasks, the dense V-Net encoder was utilized by appending a sequence of fc layers; for target segmentation tasks, the entire dense VNet was utilized. Since NiftyNet is developed in Tensorflow, all five target tasks are re-implemented using their build-in configuration. For each target task, hyper-parameters (e.g., learning rate and optimizer) were tuned and applied extensive data augmentations (e.g., rotation and scaling).

Inflated 3D: The Inflated 3D (I3D) model pre-trained from Flow streams in the Kinetics dataset was downloaded and then fine-tuned on each of the five target tasks. The input sub-volume is copied into two channels to align with the required input shape. For target classification tasks, the pre-trained I3D was taken and a sequence of randomly initialized fully-connected layers was appended. For target segmentation tasks, the pre-trained I3D was taken as the encoder and expand a decoder to predict the segmentation map, resulting in a U-Net like architecture. The decoder is the same as that implemented in our 3D U-Net, consisting of up-sampling layers followed by a sequence of convolutional layers, batch normalization, and ReLU activation. Besides, four skip connections are built between the encoder and decoder, in which feature maps before each pooling layer in the encoder are concatenated with same-scale feature maps in the decoder. All of the layers in the model are trainable during transfer learning. Adam method with a learning rate of 1e-4 is used for optimization MedicalNet: The MedicalNet models that have been pre-trained on eight publicly available 3D segmentation datasets were downloaded. ResNet-50 and ResNet-101 backbones were chosen because they have the most compelling backbones for target segmentation and classification tasks, respectively. Like I3D, a decoder was appended at the end of the pre-trained encoder, randomly initialize its weights, and the encoder was then linked with the decoder using skip connections. Owing to the 3D ResNet backbones, the resultant segmentation network for MedicalNet is much heavier than our 3D U-Net. To be consistent with the original programming platform of MedicalNet, all five target tasks were re-implemented in PyTorch, using the same data separation and augmentation. The highest results achieved by any of the two backbones in are then reported in Table 3 as discussed above (refer to FIG. 6).

Ablation experiments—Local pixel shuffling vs. global patch shuffling: Above, the results of patch-shuffling are reported as a baseline in Table 3 (refer to FIG. 6) and the local-shuffling technique is reported at FIG. 4. To emphasize the value of preserving local and global structural consistency in the proxy task, an explicit comparison between the two counterparts is further provided at FIG. 13B, arriving at three findings, namely:

Firstly, global patch-shuffling preserves local information while distorting global structure; local pixel shuffling maintains global structure but loses local details.

Secondly, for same-domain transfer learning (e.g., pre-training and fine-tuning in CT images), global-shuffling and local-shuffling reveal no significant difference in terms of target task performance. Note that local-shuffling is preferable when recognizing small objects in target tasks (e.g., pulmonary nodule and embolism), whereas patch-shuffling is beneficial for large objects (e.g., brain tumor and liver).

Thirdly, for cross-domain transfer learning (e.g., pre-training in CT and fine-tuning in MRI images), models pre-trained by the described local-shuffling technique noticeably outperforms those pre-trained by patch-shuffling.

Compute loss on cutouts vs. entire images: The results of the ablation study for in-painting and inner-cutout on five target tasks are presented in FIG. 13B. All the hyper-parameters were set the same except for one factor: where to compute MSE loss, only cutout areas or the entire image. In general, there is a marginal difference in target segmentation tasks, but inner-cutout is superior to in-painting in target classification tasks. These results are in line with the supporting hypothesis behind the disclosed embodiments. As described above with respect to the experiments, a model must distinguish original versus transformed parts within the image, preserving the context if it is original and, otherwise, in-painting the context. Seemingly, in-painting that only computes loss on cutouts can fail to learn comprehensive representation as it is unable to leverage advancements from both ends.

Figure 13C:
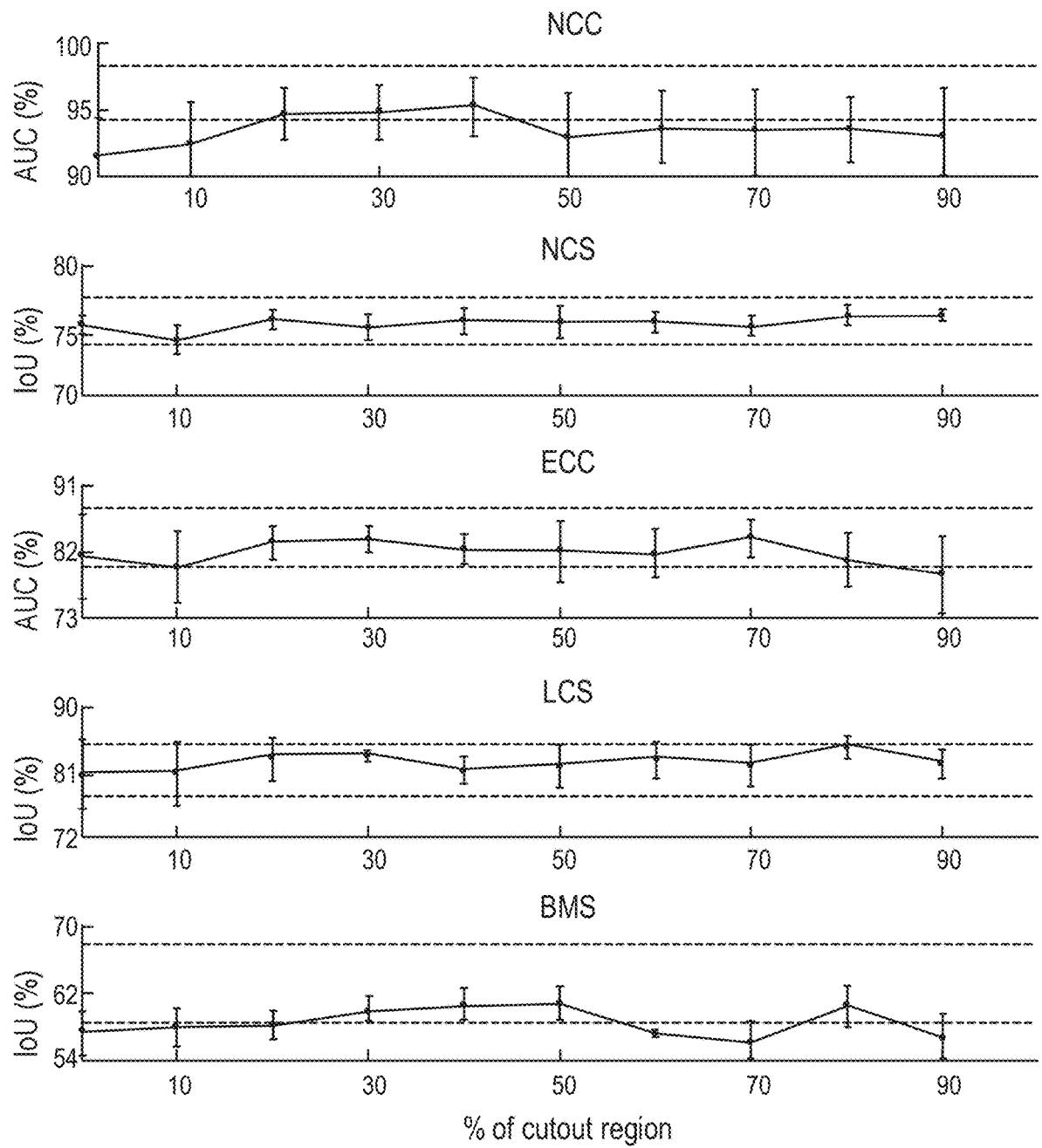
FIG. 13C depicts results from an extensive search for the optimal size of cutout regions spanning from 0% to 90%, incremented by 10%, according to described embodiments.

FIG. 13C depicts results from an extensive search for the optimal size of cutout regions spanning from 0% to 90%, incremented by 10%, according to described embodiments.

As shown here, the points plotted within the shaded area denote no significant difference (p>0:05) from the pinnacle from the curve. The horizontal top and middle dotted lines refer to the performances achieved by Models Genesis and achieved by learning from scratch, respectively. This ablation study reveals that cutting 20% to 40% of regions out could produce the most robust performance of target tasks. As a result, in our implementation, a cutout around 25% of the regions from each sub-volume is ultimately recommended, but not required.

Masked area size in outer-cutout: When applying cutout transformations to the disclosed self-supervised learning framework, one hyper-parameter is utilized to evaluate the size of cutout regions. Intuitively, it can influence the difficulty of the image restoration task. To explore the impact of this parameter on the performance of target tasks, an ablation study was conducted to extensively search for the optimal value, spanning from 0% to 90%, incremented by intervals of 10%. FIG. 13C shows the performance of all five target tasks under different settings, suggesting that outer-cutout is robust to hyper-parameter changes to some extent. This finding is also consistent with that recommended in the original in-painting technique, in which a number of smaller possibly overlapping masks are removed, covering up to ¼ of the image. Altogether, a cutout of less than ¼ of the entire sub-volume was utilized in both outer cutout and inner cutout implementations.

While the subject matter disclosed herein has been described by way of example and in terms of the specific embodiments, it is to be understood that the claimed embodiments are not limited to the explicitly enumerated embodiments disclosed. To the contrary, the disclosure is intended to cover various modifications and similar arrangements as are apparent to those skilled in the art. Therefore, the scope of the appended claims is to be accorded the broadest interpretation so as to encompass all such modifications and similar arrangements. It is to be understood that the above description is intended to be illustrative, and not restrictive. Many other embodiments will be apparent to those of skill in the art upon reading and understanding the above description. The scope of the disclosed subject matter is therefore to be determined in reference to the appended claims, along with the full scope of equivalents to which such claims are entitled.

What is claimed is:

1. A system comprising:
a memory to store instructions;
a processor to execute the instructions stored in the memory;
wherein the system is specially configured to generate self-taught generic models without requiring manual labeling of input images, by performing the following operations:
execute instructions via the processor for cropping a sub-volume from each 3D input image;
performing image transformations upon each of the sub-volumes cropped from the 3D input images to generate transformed sub-volumes; and
training an encoder-decoder architecture with skip connections to learn a common image representation by restoring the original sub-volumes cropped from the 3D input images from the transformed sub-volumes generated via the image transformations.

2. The system of claim 1, wherein training the encoder-decoder architecture to learn the common image representation comprises recovering anatomical patterns from the transformed sub-volumes.

3. The system of claim 1, wherein cropping the sub-volume from each 3D input image comprises cropping an arbitrarily-sized sub-volume at a randomly chosen location from the 3D input image.

4. The system of claim 3:
wherein cropping the sub-volume from each 3D input image comprises cropping the sub-volume from an unlabeled and un-annotated volumetric (3D) Computed Tomography (CT) scan; and
wherein training the encoder-decoder architecture comprises providing as input to the encoder-decoder architecture, the transformed sub-volumes.

5. The system of claim 1:
wherein performing multiple transformations comprises performing at most three of the four transformations selected from the group comprising: (i) a non-linear image transformation, (ii) a local-shuffling image transformation, (iii) an outer-cutout image transformation, and (iv) an inner-cutout image transformation; and
wherein the image transformations produce the transformed sub-volumes.

6. The system of claim 5:
wherein each of the outer-cutout and inner-cutout transformations are mutually exclusive, prohibiting both from being performed against any single cropped sub-volume.

7. The system of claim 1, wherein performing the image transformations upon each of the sub-volumes further comprises creating, for each cropped sub-volume:
an identity mapping sub-volume transformation; and
multiple combined transformations formed through a combination of at most three of the four transformations selected from the group comprising: (i) a non-linear image transformation, (ii) a local-shuffling image transformation, (iii) an outer-cutout image transformation, and (iv) an inner-cutout image transformation.

8. The system of claim 1, wherein training the encoder-decoder architecture to learn the common image representation by restoring the original sub-volumes from the transformed sub-volumes comprises computing a reconstruction loss (MSE) between a model prediction and a ground truth corresponding to the original sub-volumes prior to having undergone any image transformations.

9. The system of claim 1, further comprising:
fine-tuning the trained encoder-decoder architecture for target segmentation tasks.

10. The system of claim 1, further comprising:
fine-tuning the trained encoder architecture for target classification tasks.

11. Non-transitory computer-readable storage media having instructions stored thereupon that, when executed by a system having at least a processor and a memory therein, the instructions cause the system to generate self-taught generic models without requiring manual labeling of input images, by performing operations including:
cropping a sub-volume from each 3D input image;
performing image transformations upon each of the sub-volumes cropped from the 3D input images to generate transformed sub-volumes; and
training an encoder-decoder architecture with skip connections to learn a common image representation by restoring the original sub-volumes cropped from the 3D input images from the transformed sub-volumes generated via the image transformations.

12. The non-transitory computer readable storage media of claim 11:
   wherein training the encoder-decoder architecture to learn the common image representation comprises recovering anatomical patterns from the transformed sub-volumes;
   wherein cropping the sub-volume from each 3D input image comprises cropping an arbitrarily-sized sub-volume at a randomly chosen location from the 3D input image;
   wherein cropping the sub-volume from each 3D input image comprises cropping the sub-volume from an unlabeled and un-annotated volumetric (3D) Computed Tomography (CT) scan; and
   wherein training the encoder-decoder architecture comprises providing as input to the encoder-decoder architecture, the transformed sub-volumes.

13. The non-transitory computer readable storage media of claim 11:
   wherein performing multiple transformations comprises performing at most three of the four transformations selected from the group comprising: (i) a non-linear image transformation, (ii) a local-shuffling image transformation, (iii) an outer-cutout image transformation, and (iv) an inner-cutout image transformation; and
   wherein the image transformations produce the transformed sub-volumes.

14. The non-transitory computer readable storage media of claim 13:
   wherein each of the outer-cutout and inner-cutout transformations are mutually exclusive, prohibiting both from being performed against any single cropped sub-volume.

15. The non-transitory computer readable storage media of claim 11, wherein performing the image transformations upon each of the sub-volumes further comprises creating, for each cropped sub-volume:
   an identity mapping sub-volume transformation; and
   multiple combined transformations formed through a combination of at most three of the four transformations selected from the group comprising: (i) a non-linear image transformation, (ii) a local-shuffling image transformation, (iii) an outer-cutout image transformation, and (iv) an inner-cutout image transformation.

16. The non-transitory computer readable storage media of claim 11, wherein training the encoder-decoder architecture to learn the common image representation by restoring the original sub-volumes from the transformed sub-volumes comprises computing a reconstruction loss (MSE) between a model prediction and a ground truth corresponding to the original sub-volumes prior to having undergone any image transformations.

17. The non-transitory computer readable storage media of claim 11, wherein the instructions cause the system to performing operations further including:
   fine-tuning the trained encoder-decoder architecture for target segmentation tasks.

18. The non-transitory computer readable storage media of claim 11, wherein the instructions cause the system to performing operations further including:
   fine-tuning the trained encoder architecture for target classification tasks.

19. A method performed by a system having at least a processor and a memory therein to execute instructions for generating self-taught generic models without requiring manual labeling of input images, wherein the method comprises:
   cropping a sub-volume from each 3D input image;
   performing image transformations upon each of the sub-volumes cropped from the 3D input images to generate transformed sub-volumes; and
   training an encoder-decoder architecture with skip connections to learn a common image representation by restoring the original sub-volumes cropped from the 3D input images from the transformed sub-volumes generated via the image transformations.

20. The method of claim 19:
   wherein training the encoder-decoder architecture to learn the common image representation comprises recovering anatomical patterns from the transformed sub-volumes;
   wherein cropping the sub-volume from each 3D input image comprises cropping an arbitrarily-sized sub-volume at a randomly chosen location from the 3D input image;
   wherein cropping the sub-volume from each 3D input image comprises cropping the sub-volume from an unlabeled and un-annotated volumetric (3D) Computed Tomography (CT) scan; and
   wherein training the encoder-decoder architecture comprises providing as input to the encoder-decoder architecture, the transformed sub-volumes.

* * * * *